United States Patent
Sabbadini

(10) Patent No.: US 7,862,812 B2
(45) Date of Patent: *Jan. 4, 2011

(54) METHODS FOR DECREASING IMMUNE RESPONSE AND TREATING IMMUNE CONDITIONS

(75) Inventor: Roger A. Sabbadini, Lakeside, CA (US)

(73) Assignee: Lpath, Inc., San Diego, CA (US)

( * ) Notice: Subject to any disclaimer, the term of this patent is extended or adjusted under 35 U.S.C. 154(b) by 56 days.

This patent is subject to a terminal disclaimer.

(21) Appl. No.: 11/784,417

(22) Filed: Apr. 6, 2007

(65) Prior Publication Data

US 2007/0280933 A1 Dec. 6, 2007

Related U.S. Application Data

(63) Continuation-in-part of application No. 11/588,973, filed on Oct. 27, 2006.

(60) Provisional application No. 60/810,185, filed on May 31, 2006, provisional application No. 60/835,569, filed on Aug. 4, 2006.

(51) Int. Cl.
*A61K 39/395* (2006.01)

(52) U.S. Cl. .................................. 424/130.1; 530/387.1

(58) Field of Classification Search ........................ None
See application file for complete search history.

(56) References Cited

U.S. PATENT DOCUMENTS

| | | | |
|---|---|---|---|
| 3,773,919 A | 11/1973 | Boswell et al. |
| 3,940,382 A | 2/1976 | Umezawa et al. |
| 3,953,293 A | 4/1976 | Horii et al. |
| 3,953,422 A | 4/1976 | Pfeiffer |
| 3,959,255 A | 5/1976 | Chazan et al. |
| 3,962,429 A | 6/1976 | Furuno et al. |
| 3,974,137 A | 8/1976 | Schreiber et al. |
| 3,978,214 A | 8/1976 | Mallams et al. |
| 3,981,861 A | 9/1976 | Chazan et al. |
| 3,984,393 A | 10/1976 | Magerlein |
| 3,984,395 A | 10/1976 | Daniels et al. |
| 3,988,316 A | 10/1976 | Weinstein et al. |
| 3,996,205 A | 12/1976 | Magerlein |
| 3,997,524 A | 12/1976 | Nagabhushan |
| 4,002,608 A | 1/1977 | Wright et al. |
| 4,003,922 A | 1/1977 | Kavadias et al. |
| 4,009,328 A | 2/1977 | Mallams et al. |
| 4,011,390 A | 3/1977 | Weinstein et al. |
| 4,012,576 A | 3/1977 | Kawaguchi et al. |
| 4,020,269 A | 4/1977 | Hiraga et al. |
| 4,024,332 A | 5/1977 | Fenner et al. |
| 4,031,210 A | 6/1977 | Chazan et al. |
| 4,032,404 A | 6/1977 | Tomita et al. |
| 4,038,478 A | 7/1977 | Magerlein |
| 4,044,123 A | 8/1977 | Daniels et al. |
| 4,049,498 A | 9/1977 | Weinstein et al. |
| 4,051,315 A | 9/1977 | Godfrey et al. |
| 4,064,339 A | 12/1977 | Coussediere et al. |
| 4,065,615 A | 12/1977 | Horii et al. |
| 4,066,752 A | 1/1978 | Mallams et al. |
| 4,085,208 A | 4/1978 | Mallams et al. |
| 4,101,556 A | 7/1978 | Kavadias et al. |
| 4,107,435 A | 8/1978 | Ross |
| 4,117,221 A | 9/1978 | Daniels |
| 4,120,955 A | 10/1978 | Umezawa et al. |
| 4,125,707 A | 11/1978 | Arcamone et al. |
| 4,136,254 A | 1/1979 | Nagabhushan et al. |
| 4,140,849 A | 2/1979 | Umezawa et al. |
| 4,146,617 A | 3/1979 | Chazan et al. |
| 4,150,949 A | 4/1979 | Smith |
| 4,166,114 A | 8/1979 | Igarashi |
| 4,169,198 A | 9/1979 | Martin et al. |
| 4,170,642 A | 10/1979 | Umezawa et al. |
| 4,170,643 A | 10/1979 | Gero et al. |
| 4,176,178 A | 11/1979 | Martin et al. |
| 4,178,437 A | 12/1979 | Thomas |
| 4,179,337 A | 12/1979 | Davis et al. |

(Continued)

FOREIGN PATENT DOCUMENTS

| | | |
|---|---|---|
| CA | 2019559 C | 12/1990 |
| EP | 0154734 A1 | 9/1985 |
| EP | 0173648 | 3/1986 |
| EP | 0173663 | 3/1986 |
| EP | 0183070 A2 | 6/1986 |
| EP | 0244234 A2 | 11/1987 |
| EP | 0344955 A2 | 12/1989 |
| EP | 0125023 B1 | 6/1991 |
| EP | 0519596 A1 | 5/1992 |
| EP | 0120694 B1 | 7/1993 |

(Continued)

OTHER PUBLICATIONS

Abe et al., "Novel Antitumor Antibiotics, Saptomycins D and E," J. Antibiot. (Tokyo) 44(8):908-911 (1991).

(Continued)

*Primary Examiner*—Larry R. Helms
*Assistant Examiner*—Meera Natarajan
(74) *Attorney, Agent, or Firm*—BioTechnology Law Group; Daniel M. Chambers

(57) ABSTRACT

The present invention relates to compositions and methods for decreasing an immune response in an animal comprising administering to said animal an agent that binds a bioactive lipid and reduces the effective concentration of said bioactive lipid. Also provided are methods for treating diseases or conditions, including autoimmune disorders, which are characterized by an aberrant, excessive or undesired immune response. The methods of the invention utilize agents that bind bioactive lipids and are capable of decreasing the effective concentration of the bioactive lipid. In some embodiments, the agent is a monoclonal antibody that is reactive against sphingosine-1-phosphate (S1P) or lysophosphatidic acid (LPA).

13 Claims, No Drawings

U.S. PATENT DOCUMENTS

| | | |
|---|---|---|
| 4,181,797 A | 1/1980 | Naito et al. |
| 4,183,920 A | 1/1980 | Kurath et al. |
| 4,187,296 A | 2/1980 | Tadanier et al. |
| 4,187,297 A | 2/1980 | Martin et al. |
| 4,187,298 A | 2/1980 | Martin et al. |
| 4,187,299 A | 2/1980 | Post |
| 4,187,372 A | 2/1980 | Carney et al. |
| 4,189,569 A | 2/1980 | Carney et al. |
| 4,192,867 A | 3/1980 | Martin et al. |
| 4,195,170 A | 3/1980 | Umezawa et al. |
| 4,196,197 A | 4/1980 | Tadanier et al. |
| 4,199,570 A | 4/1980 | Igarashi et al. |
| 4,200,628 A | 4/1980 | Igarashi et al. |
| 4,201,774 A | 5/1980 | Igarashi et al. |
| 4,205,070 A | 5/1980 | Tadanier et al. |
| 4,207,314 A | 6/1980 | Collum |
| 4,207,415 A | 6/1980 | Carney et al. |
| 4,208,407 A | 6/1980 | Carney et al. |
| 4,208,531 A | 6/1980 | Canas-Rodriquez |
| 4,209,511 A | 6/1980 | Oka et al. |
| 4,212,859 A | 7/1980 | Daniels et al. |
| 4,213,971 A | 7/1980 | McAlpine |
| 4,213,972 A | 7/1980 | Martin |
| 4,213,974 A | 7/1980 | Martin |
| 4,214,074 A | 7/1980 | Richardson et al. |
| 4,214,075 A | 7/1980 | Tadanier et al. |
| 4,214,076 A | 7/1980 | McAlpine |
| 4,214,078 A | 7/1980 | Goldstein et al. |
| 4,214,079 A | 7/1980 | Martin |
| 4,214,080 A | 7/1980 | Carney |
| 4,216,210 A | 8/1980 | Carney et al. |
| 4,217,446 A | 8/1980 | Moore |
| 4,219,642 A | 8/1980 | Collum et al. |
| 4,219,643 A | 8/1980 | Seely |
| 4,219,644 A | 8/1980 | Goldstein et al. |
| 4,220,756 A | 9/1980 | Kloss et al. |
| 4,223,022 A | 9/1980 | Rosenkrantz et al. |
| 4,223,024 A | 9/1980 | McAlpine et al. |
| 4,226,978 A | 10/1980 | Boguslaski et al. |
| 4,230,847 A | 10/1980 | Nagabhushan et al. |
| 4,242,331 A | 12/1980 | Gasc et al. |
| 4,248,865 A | 2/1981 | Igarashi et al. |
| 4,250,170 A | 2/1981 | Kawaguchi et al. |
| 4,250,304 A | 2/1981 | Martin et al. |
| 4,251,511 A | 2/1981 | Whaley et al. |
| 4,251,516 A | 2/1981 | Martin et al. |
| 4,252,972 A | 2/1981 | Tadanier et al. |
| 4,255,421 A | 3/1981 | Watanabe et al. |
| 4,273,923 A | 6/1981 | Igarashi et al. |
| 4,275,149 A | 6/1981 | Litman et al. |
| 4,279,997 A | 7/1981 | Oka et al. |
| 4,283,528 A | 8/1981 | Daniels et al. |
| RE30,750 E | 9/1981 | Diack et al. |
| 4,288,547 A | 9/1981 | Yamamoto |
| 4,297,485 A | 10/1981 | Umezawa et al. |
| 4,297,486 A | 10/1981 | Fujii et al. |
| 4,301,144 A | 11/1981 | Iwashita et al. |
| 4,312,859 A | 1/1982 | Petersen et al. |
| 4,317,904 A | 3/1982 | Martin et al. |
| 4,318,980 A | 3/1982 | Boguslaski et al. |
| 4,319,022 A | 3/1982 | Martin et al. |
| 4,330,673 A | 5/1982 | Rosenbrook, Jr. |
| RE30,985 E | 6/1982 | Cartaya |
| 4,336,369 A | 6/1982 | Petersen et al. |
| 4,337,336 A | 6/1982 | Umezawa et al. |
| 4,347,354 A | 8/1982 | Cron et al. |
| 4,349,667 A | 9/1982 | Fujii et al. |
| 4,365,020 A | 12/1982 | Gado et al. |
| 4,369,251 A | 1/1983 | Jarai et al. |
| 4,376,110 A | 3/1983 | David et al. |
| 4,380,625 A | 4/1983 | Stadler et al. |
| 4,387,219 A | 6/1983 | Yamamoto et al. |
| 4,418,193 A | 11/1983 | McAlpine et al. |
| 4,424,343 A | 1/1984 | Cron et al. |
| 4,424,344 A | 1/1984 | Kirst et al. |
| 4,424,345 A | 1/1984 | Kirst et al. |
| 4,438,107 A | 3/1984 | Watanabe et al. |
| 4,438,260 A | 3/1984 | Petersen et al. |
| 4,455,419 A | 6/1984 | Umezawa et al. |
| 4,468,512 A | 8/1984 | Kirst et al. |
| 4,468,513 A | 8/1984 | Kirst et al. |
| 4,485,045 A | 11/1984 | Regen |
| 4,486,418 A | 12/1984 | Watanabe et al. |
| 4,493,831 A | 1/1985 | Takaya et al. |
| 4,496,689 A | 1/1985 | Mitra |
| 4,503,046 A | 3/1985 | Loibner et al. |
| 4,544,545 A | 10/1985 | Ryan et al. |
| 4,554,269 A | 11/1985 | Takaya et al. |
| 4,560,655 A | 12/1985 | Baker |
| 4,568,649 A | 2/1986 | Bertoglio-Matte |
| 4,617,293 A | 10/1986 | Wahlig et al. |
| 4,626,513 A | 12/1986 | Burton et al. |
| 4,640,835 A | 2/1987 | Shimizu et al. |
| 4,645,760 A | 2/1987 | Pierson |
| 4,647,656 A | 3/1987 | Watanabe et al. |
| 4,656,160 A | 4/1987 | Takaya et al. |
| 4,657,866 A | 4/1987 | Kumar |
| 4,658,830 A | 4/1987 | Sarnoff |
| 4,670,417 A | 6/1987 | Iwasaki et al. |
| 4,676,980 A | 6/1987 | Segal et al. |
| 4,737,456 A | 4/1988 | Weng et al. |
| 4,767,704 A | 8/1988 | Cleveland et al. |
| 4,791,192 A | 12/1988 | Nakagawa et al. |
| 4,816,397 A | 3/1989 | Boss et al. |
| 4,816,450 A | 3/1989 | Bell et al. |
| 4,816,567 A | 3/1989 | Cabilly et al. |
| 4,855,287 A | 8/1989 | Watanabe et al. |
| 4,873,225 A | 10/1989 | Umezawa et al. |
| 4,895,724 A | 1/1990 | Cardinal et al. |
| 4,902,790 A | 2/1990 | Mangia et al. |
| 4,927,762 A | 5/1990 | Darfler |
| 4,937,232 A | 6/1990 | Bell et al. |
| 4,946,778 A | 8/1990 | Ladner et al. |
| 4,985,549 A | 1/1991 | Giobbio et al. |
| 5,010,175 A | 4/1991 | Rutter et al. |
| 5,013,556 A | 5/1991 | Woodle et al. |
| 5,079,263 A | 1/1992 | Zeeck et al. |
| 5,122,469 A | 6/1992 | Mather et al. |
| 5,137,919 A | 8/1992 | Igarashi et al. |
| 5,151,360 A | 9/1992 | Handa et al. |
| 5,204,244 A | 4/1993 | Fell et al. |
| 5,225,539 A | 7/1993 | Winter |
| 5,229,275 A | 7/1993 | Goroff |
| 5,248,824 A | 9/1993 | Igrashi et al. |
| 5,260,203 A | 11/1993 | Ladner et al. |
| 5,260,288 A | 11/1993 | Igarashi et al. |
| 5,270,163 A | 12/1993 | Gold et al. |
| 5,288,514 A | 2/1994 | Ellman |
| 5,314,695 A | 5/1994 | Brown |
| 5,331,014 A | 7/1994 | Kimura et al. |
| 5,369,030 A | 11/1994 | Hannun et al. |
| 5,391,800 A | 2/1995 | Igarashi et al. |
| 5,430,160 A | 7/1995 | Holton |
| 5,442,047 A | 8/1995 | Tann et al. |
| 5,444,087 A | 8/1995 | Patel et al. |
| 5,455,030 A | 10/1995 | Ladner et al. |
| 5,488,038 A | 1/1996 | Kondo et al. |
| 5,506,337 A | 4/1996 | Summerton et al. |
| 5,518,889 A | 5/1996 | Ladner et al. |
| 5,519,134 A | 5/1996 | Acevedo et al. |
| 5,525,735 A | 6/1996 | Gallop et al. |
| 5,530,101 A | 6/1996 | Queen et al. |
| 5,534,615 A | 7/1996 | Baker et al. |
| 5,534,621 A | 7/1996 | Ladner et al. |

| | | | | | | |
|---|---|---|---|---|---|---|
| 5,539,083 | A | 7/1996 | Cook et al. | 6,407,213 B1 | 6/2002 | Carter et al. |
| 5,545,807 | A | 8/1996 | Surani et al. | 6,423,527 B1 | 7/2002 | Saba et al. |
| 5,549,974 | A | 8/1996 | Holmes | 6,479,284 B1 | 11/2002 | Marasco et al. |
| 5,565,332 | A | 10/1996 | Hoogenboom et al. | 6,500,931 B1 | 12/2002 | Tempest et al. |
| 5,567,610 | A | 10/1996 | Borrebaeck et al. | 6,534,322 B1 | 3/2003 | Sabbadini |
| 5,569,588 | A | 10/1996 | Ashby et al. | 6,534,323 B1 | 3/2003 | Sabbadini |
| 5,573,905 | A | 11/1996 | Lerner et al. | 6,548,640 B1 | 4/2003 | Winter |
| 5,585,089 | A | 12/1996 | Queen et al. | 6,571,638 B2 | 6/2003 | Hines et al. |
| 5,585,476 | A | 12/1996 | MacLennan et al. | 6,610,835 B1 | 8/2003 | Liotta et al. |
| 5,589,369 | A | 12/1996 | Seidman et al. | 6,613,322 B2 | 9/2003 | Tabas et al. |
| 5,591,669 | A | 1/1997 | Krimpenfort et al. | 6,639,055 B1 | 10/2003 | Carter et al. |
| 5,593,853 | A | 1/1997 | Chen et al. | 6,649,362 B2 | 11/2003 | Gamble et al. |
| 5,618,795 | A | 4/1997 | Kondo et al. | 6,858,383 B2 | 2/2005 | Sabbadini |
| 5,621,085 | A | 4/1997 | Dall'Asta et al. | 6,881,546 B2 | 4/2005 | Sabbadini |
| 5,624,821 | A | 4/1997 | Winter et al. | 7,060,808 B1 | 6/2006 | Goldstein et al. |
| 5,627,171 | A | 5/1997 | Park et al. | 7,087,409 B2 | 8/2006 | Barbas, III et al. |
| 5,631,394 | A | 5/1997 | Wei et al. | 7,169,390 B2 | 1/2007 | Sabbadini |
| 5,656,735 | A | 8/1997 | Dall'Asta et al. | 2001/0041688 A1 | 11/2001 | Waeber et al. |
| 5,663,404 | A | 9/1997 | Igarashi et al. | 2002/0150582 A1 | 10/2002 | Friedrichs et al. |
| 5,677,189 | A | 10/1997 | Igarashi et al. | 2003/0096022 A1 | 5/2003 | Sabbadini |
| 5,677,288 | A | 10/1997 | Marangos | 2003/0125533 A1 | 7/2003 | Kossida et al. |
| 5,677,337 | A | 10/1997 | Wei et al. | 2003/0219782 A1 | 11/2003 | Saba et al. |
| 5,693,761 | A | 12/1997 | Queen et al. | 2003/0229208 A1 | 12/2003 | Queen et al. |
| 5,693,762 | A | 12/1997 | Queen et al. | 2005/0226862 A1 | 10/2005 | Sabbadini |
| 5,702,892 | A | 12/1997 | Mulligan-Kehoe | 2007/0148168 A1* | 6/2007 | Sabbadini et al. ........ 424/133.1 |
| 5,714,350 | A | 2/1998 | Co et al. | | | |
| 5,763,587 | A | 6/1998 | Mangia | | FOREIGN PATENT DOCUMENTS | |
| 5,770,429 | A | 6/1998 | Lonberg et al. | EP | 0194276 B1 | 8/1993 |
| 5,777,085 | A | 7/1998 | Co et al. | EP | 0239400 B1 | 8/1994 |
| 5,814,488 | A | 9/1998 | Zhao et al. | JP | 09-110722 | 4/1987 |
| 5,821,047 | A | 10/1998 | Garrard et al. | JP | 2000-293181 A | 10/2000 |
| 5,834,597 | A | 11/1998 | Tso et al. | WO | WO 86/01533 A1 | 3/1986 |
| 5,840,867 | A | 11/1998 | Toole et al. | WO | WO 87/00195 A1 | 1/1987 |
| 5,851,782 | A | 12/1998 | Hannun et al. | WO | WO 90/03430 A1 | 4/1990 |
| 5,861,155 | A | 1/1999 | Lin | WO | WO 91/19735 A1 | 12/1991 |
| 5,869,620 | A | 2/1999 | Whitlow et al. | WO | WO 91/19813 A1 | 12/1991 |
| 5,876,747 | A | 3/1999 | Stracher et al. | WO | WO 92/00091 A1 | 1/1992 |
| 5,877,167 | A | 3/1999 | Igarashi et al. | WO | WO 93/11161 A1 | 6/1993 |
| 5,882,644 | A | 3/1999 | Chang et al. | WO | WO 93/20242 A1 | 10/1993 |
| 5,912,144 | A | 6/1999 | Au-Young et al. | WO | WO 94/16731 A1 | 8/1994 |
| 5,919,687 | A | 7/1999 | Chatterjee | WO | WO 96/27011 A1 | 9/1996 |
| 5,929,039 | A | 7/1999 | Woodcock et al. | WO | WO 96/32478 A1 | 10/1996 |
| 5,932,448 | A | 8/1999 | Tso et al. | WO | WO 97/00271 A1 | 1/1997 |
| 5,989,803 | A | 11/1999 | Tabas et al. | WO | WO 97/44019 | 11/1997 |
| 6,013,256 | A | 1/2000 | Light et al. | WO | WO 98/03529 | 1/1998 |
| 6,025,165 | A | 2/2000 | Whitlow et al. | WO | WO 98/28445 | 7/1998 |
| 6,027,725 | A | 2/2000 | Whitlow et al. | WO | WO 98/40349 | 9/1998 |
| 6,031,071 | A | 2/2000 | Mandeville et al. | WO | WO 98/52547 A1 | 11/1998 |
| 6,046,037 | A | 4/2000 | Hiatt et al. | WO | WO 98/57179 | 12/1998 |
| 6,051,598 | A | 4/2000 | Shayman et al. | WO | WO 99/07855 | 2/1999 |
| 6,057,126 | A | 5/2000 | Munroe et al. | WO | WO 99/12890 | 3/1999 |
| 6,075,181 | A | 6/2000 | Kucherlapati et al. | WO | WO 99/16888 | 4/1999 |
| 6,080,321 | A | 6/2000 | Spickermann | WO | WO 99/33972 | 7/1999 |
| 6,098,631 | A | 8/2000 | Holoshitz et al. | WO | WO 99/38983 | 8/1999 |
| 6,114,598 | A | 9/2000 | Kucherlapati et al. | WO | WO 99/41265 | 8/1999 |
| 6,121,246 | A | 9/2000 | Isner | WO | WO 99/41266 | 8/1999 |
| 6,129,914 | A | 10/2000 | Weiner et al. | WO | WO 99/46277 | 9/1999 |
| 6,130,067 | A | 10/2000 | Tsui | WO | WO 99/61581 | 12/1999 |
| 6,130,235 | A | 10/2000 | Mavunkel et al. | WO | WO 00/00593 | 1/2000 |
| 6,140,060 | A | 10/2000 | Chun et al. | WO | WO 00/21919 | 4/2000 |
| 6,150,584 | A | 11/2000 | Kucherlapati et al. | WO | WO 00/40262 | 7/2000 |
| 6,162,963 | A | 12/2000 | Kucherlapati et al. | WO | WO 00/52173 | 9/2000 |
| 6,180,370 | B1 | 1/2001 | Queen et al. | WO | WO 00/56135 | 9/2000 |
| 6,187,562 | B1 | 2/2001 | Duckworth et al. | WO | WO 00/58448 | 10/2000 |
| 6,210,671 | B1 | 4/2001 | Co | WO | WO 00/58491 | 10/2000 |
| 6,210,976 | B1 | 4/2001 | Sabbadini | WO | WO 00/59517 | 10/2000 |
| 6,284,798 | B1 | 9/2001 | Amtmann et al. | WO | WO 00/70028 | 11/2000 |
| 6,306,911 | B1 | 10/2001 | Wachter et al. | WO | WO 00/72833 | 12/2000 |
| 6,310,191 | B1 | 10/2001 | Collins et al. | WO | WO 01/04108 | 1/2001 |
| 6,323,201 | B1 | 11/2001 | Carson et al. | WO | WO 01/04139 | 1/2001 |
| 6,329,511 | B1 | 12/2001 | Vasquez et al. | WO | WO 01/07418 | 2/2001 |
| 6,350,861 | B1 | 2/2002 | Co et al. | WO | WO 01/31029 | 5/2001 |
| 6,352,844 | B1 | 3/2002 | Maurer et al. | | | |

| | | |
|---|---|---|
| WO | WO 01/37836 A1 | 5/2001 |
| WO | WO 01/38295 | 5/2001 |
| WO | WO 01/55410 | 8/2001 |
| WO | WO 01/57057 | 8/2001 |
| WO | WO 01/60990 | 8/2001 |
| WO | WO 01/71045 | 9/2001 |
| WO | WO 01/72701 | 10/2001 |
| WO | WO 01/80903 | 11/2001 |
| WO | WO 01/85953 | 11/2001 |
| WO | WO 02/17899 A2 | 3/2002 |
| WO | WO 02/051439 A2 | 7/2002 |
| WO | WO 03/097028 A1 | 11/2003 |
| WO | WO 2006/105062 A2 | 10/2006 |

OTHER PUBLICATIONS

Abe et al., "Novel Antitumor Antibiotics, Saptomycins. I. Taxonomy of the Producing Organism, Fermentation, HPLC Analysis and Biological Activities" J. Antibiot. (Tokyo) 46(10):1530-1535 (1993).

Abe et al., "Novel Antitumor Antibiotics Saptomycins. II. Isolation, Physico-chemical Properties and Structure Elucidation" J. Antibiot. (Tokyo) 46(10):1536-1549 (1993).

Adam et al., "A Novel Cytoplasmic Domain of the p55 Tumor Necrosis Factor Receptor Initiates the Neutral Sphingomyelinase Pathway," J. Bio. Chem. 271(24):14617-14622 (1996).

Adzick et al., "Cells, matrix, growth factors, and the surgeon. The biology of scarless fetal wound repair," Ann. Surg. 220(1):10-18 (1994).

Akiyama et al., "Intraocular Injection of an Aptamer that Binds PDGF-B: A Potential Treatment for Proliferative Retinopathies," J. Cell. Physiol. 207(2):407-412 (2006).

Alemany et al., "Stimulation of Sphingosine-1-Phosphate Formation by the P2Y2 Receptor in HL-60 Cells: Ca2+ Requirement and Implication in Receptor-Mediated Ca2+ Mobilization, but not MAP Kinase Activation," Mol. Pharm. 58(3):491-497 (2000).

Allen, "Myocardial protection: is there a role for gene therapy?," Ann. Thorac. Surg. 68(5):1924-1928 (1999).

Allende et al., "Sphingosine-1-Phosphate Receptors and the Development of the Vascular System," Biochim. Biophys. Acta 1582(1-3):222-227 (2002).

Ambati et al., "Age-Related Macular Degeneration: Etiology, Pathogenesis, and Therapeutic Strategies," Surv. Ophthalmol. 48(3):257-293 (2003).

Amin et al., "Growth Factor Localization in Choroidal Neovascular Membranes of Age-Related Macular Degeneration," Investigat. Ophthalmol. Vis.Sci. 35(8):3178-3188 (1994).

Andrews et al., "Platelet-Derived Growth Factor Plays a Key Role in Proliferative Vitreoretinopathy," Investigat. Ophthalmol. Vis.Sci. 40(11):2683-2689 (1999).

Annabi et al., "Matrix Metalloproteinase Regulation of Sphingosine-1-Phosphate-Induced Angiogenic Properties of Bone Marrow Stromal Cells," Exp. Hematol. 31(7):640-649 (2003).

Antman et al., "Abciximab Facilitates the Rate and Extent of Thrombolysis: Results of the Thrombolysis In Myocardial Infarction (TIMI) 14 Trial," Circulation 99(21):2720-2732.

Argraves et al., "Sphingosine-1-Phosphate Signaling Promotes Critical Migratory Events in Vasculogenesis," J. Bio. Chem. 279(48):50580-50590 (2004).

Armulik et al, "Endothelial-Pericyte Interactions," Circ. Res. 97(6):512-523 (2005).

Asahara et al., "Tie2 Receptor Ligands, Angiopoietin-1 and Angiopoietin-2, Modulate VEGF-Induced Postnatal Neovascularization," Circ. Res. 83(3):233-240 (1998).

Awad et al., "Selective Sphingosine-1-Phosphate 1 Receptor Activation reduces Ischemia-Reperfusion Injury in Mouse Kidney," Am. J. Physiol. Renal Physiol. 290(6):F1516-F1524 (2006).

Baker et al., "Direct Quantitative Analysis of Lysophosphatidic Acid Molecular Species by Stable Isotope Dilution Electrospray Ionization Liquid Chromatography-Mass Spectrometry," Anal. Biochem. 292(2):287-295 (2001).

Barnes et al., "Methods for Growth of Cultured Cells in Serum-Free Medium," Anal. Biochem. 102(2):255-270 (1980).

Baroni et al., "Stimulatory Autoantibodies to the PDGF Receptor in Systemic Sclerosis," New Engl. J. Med. 354(25):2667-2676 (2006).

Baudhuin et al., "S1P3-Mediated Akt Activation and Cross-Talk with Platelet-Derived Growth Factor Receptor (PDGFR)," FASEB J. 18(2):341-343 (2004).

Becerril et al., "Growth Factor Levels and ROP," Ophthalmology 112 (12):2238 (2005).

Beeler et al., "The *Saccharomyces cerevisiae* TSC10-YBR265w Gene Encoding 3-Ketosphinganine Reductase Is Identified in a Screen for Temperature-sensitive Suppressors of the Ca2+-sensitive csg2DELTA Mutant" J. Biol. Chem. 273(46):30688-30694 (1998).

Benjamin et al., "A Plasticity Window for Blood Vessel Remodeling is Defined by Pericyte Coverage of the Preformed Endothelial and is Regulated by PDGF-B and VEGF," Development 125(9):1591-1598 (1998).

Berge et al., "Pharmaceutical Salts," J. Pharm. Sci. 66(1):1-19 (1977).

Bergers et al., "The Role of Pericytes in Blood Vessel Formation and Maintenance," Neuro. Oncol. 7(4):452-464 (2005).

Bohler et al., "FTY720 Exerts Differential Effects on CD4+ and CD8+ T-Lymphocyte Subpopulations Expressing Chemokine and Adhesion Receptors," Nephrol. Dial. Transplant. 19(3):702-713 (2004).

Bohler et al, "Novel Mediators of FTY720 in Human Lymphocytes," Transplantation 79(4):492-495 (2005).

Boulton et al., "Intravitreal Growth Factors in Proliferative Diabetic Retinopathy: Correlation with Neovascular Activity and Glycaemic Management," Br. J. Ophthalmol. 81(3):228-233 (1997).

Boushey et al., "Basic Mechanisms of Asthma," Environ. Health Perspect. 103(Suppl 6):229-233 (1995).

Brennan et al., "Preparation of bispecific antibodies by chemical recombination of monoclonal immunoglobulin G1 fragments," Science 229(4708):81-83 (1985).

Brenner et al., "Fas- or Ceramide-induced Apoptosis Is Mediated by a Rac1-regulated Activation of Jun N-terminal Kinase-p38 Kinases and GADD153," J. Biol. Chem. 272(35):22173-22181 (1997).

Brill et al., "Altromycins, Novel Pluramycin-like Antibiotics. II. Isolation and Elucidation of Structure," J. Antibiot. (Tokyo) 43(3):229-237 (1990).

Brindley, "Lipid Phosphate Phosphatases and Related Proteins: Signaling Functions in Development, Cell Division, and Cancer," J. Cell. Biochem. 92(5):900-912 (2004).

Brown et al., "Ranibizumab versus Verteporfin for Neovascular Age-Related Macular Degeneration," New Engl. J. Med. 355(14):1432-1444 (2006).

Buchschacher et al., "Development of Lentiviral Vectors for Gene Therapy for Human Diseases," Blood 95(8):2499-2504 (2000).

Budde et al., "First Human Trial of FTY720, A Novel Immunomodulator, in Stable Renal Transplant Patients," J. Am. Soc. Nephrol. 13(4):1073-1083 (2002).

Bugg et al., "Drugs by Design," Sci. Am. 269(6):92-98 (1993).

Butrus et al., "Increased Numbers of Mast Cells in Pterygia," Am. J. Ophthalmol. 119(2):236-237 (1995).

Bylsma et al., "Treatment of Age-Related Macular Degeneration," Clin. Exp. Optom. 88(5):322-334 (2005).

Calder et al., "Increased CD4+ Expression and Decreased IL-10 in the Anterior Chamber in Idiopathic Uveits," Invest. Ophthalmol. Vis. Sci. 40(9):2019-2024 (1999).

Carter et al., "High Level *Escherichia coli* Expression and Production of a Bivalent Humanized Antibody Fragment," Bio/Technology 10(2):163-167 (1992).

Cassidy et al., "Platelet Derived Growth Factor and Fibroblast Growth Factor Basic Levels in the Vitreous of Patients with Vitreoretinal Disirders," Br. J. Ophthalmol. 82(2):181-185 (1998).

Chae et al., "Requirement for Sphingosine-1-Phosphate Receptor-1 in Tumor Angiogenesis Demonstrated by In Vivo RNA Interference," J. Clin. Invest. 114(8):1082-1089 (2004).

Champe et al., "Monoclonal Antibodies That Block the Activity of Leukocyte Function-associated Antigen 1 Recognize Three Discrete Epitopes in the Inserted Domain of CD11a," J. Biol. Chem. 270(3):1388-1394 (1995).

Chen et al., "Analogous' Organic Synthesis of Small-Compound Libraries: Validation of Combinatorial Chemistry in Small-Molecule Synthesis," J. Amer. Chem. Soc. 116(6):2661-2662 (1994).

Chen et al., "Production and Appliction of LPA Polyclonal Antibodies," Bioorg. Medic. Chem. Lett. 10(15):1691-1693 (2000).

Chen et al., "Specific Receptor Subtype Mediation of LPA-Induced Dual Effects in Cardiac Fibroblasts," FEBS Lett. 580(19):4737-4745 (2006).

Chiba et al., "FTY720, a Novel Immunosuppressant, Induces Sequestration of Circulating Mature Lymphocytes by Acceleration of Lymphocyte Homing in Rats. I. FTY720 Selectively Decreases the Number of Circulating Mature Lymphocytes by Acceleration of Lymphocyte Homing," J. Immunol. 160(10):5037-5044 (1998).

Chmura et al. "Down-Regulation of Ceramide Production Abrogates Ionizing Radiation-Induced Cytochrome c Release and Apoptosis," Mol. Pharmcol. 57(4):792-796 (2000).

Chothia et al., "Domain Association in Immunoglobulin Molecules: The Packing of Variable Domains," J. Mol. Biol. 186(3):651-663 (1985).

Chothia et al., "Canonical Structures for the Hypervariable Regions of Immunoglobulins," J. Mol. Biol. 196(4):901-917 (1987).

Chun et al, "Lysophospholipid Receptors as Potential Drug Targets in Tissue Transplantation and Autoimmune Diseases," Curr. Pharm. Des. 12(2):161-171 (2006).

Cinamon et al., "Sphingosine 1-Phosphate Receptor 1 Promotes B Cell Localization in the Splenic Marginal Zone," Nat. Immunol. 5(7):713-720 (2004).

Ciulla et al., "Presumed Ocular Histoplasmosis Syndrome: Update on Epidemiology, Pathogenesis, and Photodynamic, Antiangiogenic, and Surgical Therapies," Curr. Opin. Ophthalmol. 12(6):442-449 (2001).

Condrescu et al., "Inhibition of Sodium-Calcium Exchange by Ceramide and Sphingosine," J. Biol. Chem. 276(6):4046-4054 (2001).

Cousins et al., "Monocyte Activation in Patients with Age-Related Macular Degeneration," Arch Ophthal. 122(7):1013-1018 (2004).

Cunningham et al., "High-resolution epitope mapping of hGH-receptor interactions by alanine-scanning mutagenesis," Science 244(4908):1081-1085 (1989).

Cuvillier et al., "Sphingosine-1-Phosphate Antagonizes Apoptosis of Human Leukemia Cells by Inhibiting Release of Cytochrome C and SMAC-Diablo From Mitochondria," Blood 98(9):2828-2836 (2001).

Cyster, "Chemokines, Sphingosine-1-Phosphate, and Cell Migration in Secondary Lymphoid Organs," Annu. Rev. Immunol. 23:127-159 (2005).

Dantas et al., "Sphingosine-1-Phosphate and Control of Vascular Tone," Am. J. Physiol. Heart Circ. Physiol. 284(6):H2045-H2052 (2003).

Danthinne et al., "Production of First Generation Adenovirus Vectors: A Review," Gene Ther. 7(20):1707-1714 (2000).

Dart, "Corneal Toxicity: The Epithelium and Stroma in Iatrogenic and Factitous Disease," Eye 17(8):886-892 (2003).

Davaille et al., "Antiproliferative Properties of Sphingosine 1-Phosphate in Human Hepatic Myofibroblasts," J. Biol. Chem. 275(44):34268-34633 (2000).

Dawson, "Activity of SC33428, a Novel Bishydrazone-Bridged Derivative of 4-Demethoxydaunorubicin, against Experimental Tumors in Mice," Cancer Res. 43(6):2880-2883 (1983).

Deguchi et al., "The S1P Receptor Modulator FTY720 Prevents the Development of Experimental Colitis in Mice," Oncol. Rep. 16(4):699-703 (2006).

Denk et al., "Effect of Growth Factors on the Activation of Human Tenon's Capsule Fibroblasts," Curr. Eye Res. 27(1):35-44 (2003).

Desmouliere et al., "Transforming Growth Factor β1 Induces α Smooth Muscle Actin Expression in Granulation Tissue Myofibroblasts and in Quiescent and Growing Cultured Fibroblasts," J. Cell Biol. 122(1):103-111 (1993).

Deutschman et al., "Predicting Obstructive Coronary Artery Disease with Serum Sphingosine-1-Phosphate," Am. Heart J. 146(1):62-68 (2003).

Di Girolamo et al., "UVB-Mediated Induction of Cytokines and Growth Factors in Pterygium Epithelial Cells Involves Cell Surface Receptors and Intracellular Signaling," Invest. Ophthalmol. Vis. Sci. 47(6):2430-2437 (2006).

Doherty et al., "Site-Specific PEGylation of Engineered Cysteine Analogues of Recombinant Human Granulocyte-Macrophage Colony-Stimulating Factor," Bioconjug. Chem. 16(5):1291-1298 (2005).

Dougherty et al., "Corneoscleral Melt after Pterygium Surgery Using A Single Intraoperative Application of Mitomycin-C," Cornea 15(5):537-540 (1996).

Ecker et al. "Rational Screening of Oligonucleotide Combinatorial Libraries for Drug Discovery," Nucl. Acids Res. 21(8):1853 (1993).

Egan et al., "Fortimicins A and B, New Aminoglycoside Antibiotics. III. Structural Identification," J. Antibiot. (Tokyo) 30(7):552-563 (1977).

Eichler et al., "Generation and Utilization of Synthetic Combinatorial Libraries," Mol. Med. Today 1(4):174-180 (1995).

Eichler et al., "Antineovascular Agents in the Treat of Eye Diseases," Curr. Pharm. Des. 12(21):2645-2660 (2006).

Eljarrat-Binstock et al., "Iontophoresis: A Non-Invasive Ocular Drug Delivery," J. Control. Release 110(3):479-489 (2006).

Ellington et al. "In Vitro Selection of RNA Molecules that Bind Specific Ligands," Nature 346(6287):818-822 (1990).

English et al., "Induction of Endothelial Cell Chemotaxis by Sphingosine-1-Phosphate and Stabilization of Endothelial Monolayer Barrier Function by Lysophosphatidic Acid, Potential Mediators of Hematopoietic Angiogenesis," J. Hematother. Stem Cell Res. 8(6):627-634 (1999).

English et al., "Sphingosine 1-Phosphate Released from Platelets during Clotting Accounts for the Potent Endothelial Cell Chemotactic Activity of Blood Serum and Provides a Novel Link between Hemostasis and Angiogenesis," FASEB J. 14 (14):2255-2265 (2000).

Eppstein et al., "Biological activity of liposome-encapsulated murine interferon y is mediated by a cell membrane receptor," Proc. Natl. Acad. Sci. USA 82(11):3688-3692 (1985).

Erber et al., "Combined Inhibition of VEGF- and PDGF-Signaling Enforces Tumor Vessel Regression by Interfering with Pericytemediated Endothelial Cell Survival Mechanisms," FASEB J. 18(2):338-340 (2004).

Espinosa-Heidmann et al., "Macrophage Depletion Diminishes Lesion Size and Severity in Experimental Choroidal Neovascularization," Invest. Ophthalmol. Vis. Sci. 44(8):3586-3592 (2003).

Felinski et al., "Glucocorticoid Regulation of Endothelial Cell Tight Junction Gene Expression: Novel Treatments for Diabetic Retinopathy," Curr. Eye Res. 30(11):949-957 (2005).

Fini, "Keratocyte and Fibroblast Phenotypes in the Repairing Cornea," Prog. Retin. Eye Res. 18(4):529-551 (1999).

Fitzgerald et al., "3,4-Dihydroxybenzylamine: An Improved Dopamine Analog Cytotoxic for Melanoma Cells in part through Oxidation Products Inhibitory to DNA pPolymerase," J. Invest. Dermatol. 80(2):119-123 (1983).

Folger et al., "Transforming Growth Factor-b—Stimulated Connective Tissue Growth Factor Expression during Corneal Myofibroblast Differentiation," Invest. Ophthalmol. Vis. Sci. 42(11):2534-2541 (2001).

Fontana et al., "Trabeculectomy with Mitomycin C: Outcomes and Risk Factors For Failure in Phakic Open-Angle Glaucoma," Ophthalmology 113(6):930-936 (2006).

Foote et al., "Antibody Framework Residues Affecting the Conformation of the Hypervariable Loops," J. Mol. Biol. 224(2):487-499 (1992).

Forrester, "Macrophages Eyed in Macular Degeneration," Nat. Med. 9 (11):1350-1351 (2003).

French et al., "Discovery and Evaluation of Inhibitors of Human Sphingosine Kinase," Cancer Res. 63(18): 5962-5969 (2003).

Fujino et al., "Amelioration of Experimental Autoimmune Encephalomyelitis in Lewis Rats by FTY720 Treatment," J. Pharmacol. Exp. Ther. 305(1):70-77 (2003).

Fujiwara et al., "Production of a New Aminoglycoside Antibiotic by a Mutant of *Bacillus circulans*," J. Antibiot. (Tokyo) 33(8):836-841 (1980).

Fujiwara et al., "Identification of Residues Responsible for Ligand Recognition and Regioisomeric Selectivity of Lysophosphatidic Acid Receptors Expressed in Mammalian Cells," J. Biol. Chem. 280(41):35038-35050 (2005).

Ganguly, "Ziracin, A Novel Oligosaccharide Antibiotic," J. Antibiot. (Tokyo) 53(10):1038-1044 (2000).

Gao et al., "The Wt1+-R394W Mouse Displays Glomerulosclerosis and Early-Onset Renal Failure Characteristic of Human Denys-Drash Syndrome," Mol. Cell. Biol. 24(22):9899-9910 (2004).

Gardell et al., "Emerging medicinal roles for lysophospholipid signaling," Trends Mol. Med. 12(2):65-75 (2006).

Gariano et al., "Retinal Angiogenesis in Development and Disease," Nature 438(7070):960-966 (2005).

Gavilondo et al., "Antibody Engineering at the Millennium," BioTechniques, 29(1):128-145 (2000).

Gerhardt et al., "Endothelial-Pericyte Interactions in Angiogenesis," Cell Tissue Res. 314(1):15-23 (2003).

Goetzl et al., "An IgM-kappa rat monoclonal antibody specific for the type 1 sphingosine 1-phosphate G protein-coupled receptor with antagonist and agonist activities," Immonol. Lett. 93(1):63-69 (2004).

Goetzl et al., "Regulation of immunity by lysosphingolipids and their G protein-coupled receptors," J. Clin. Invest. 114(11):1531-1537 (2004).

Gorin et al., "The Genetics of Age-Related Macular Degeneration," Mol. Vis. 5:29-34 (1999).

Gragoudas et al., "Pegaptanib for Neovascular Age-Related Macular Degeneration," New Eng. J. Med. 351(27):2805-2816 (2004).

Graham et al., "Characteristics of a Human Cell Line Transformed by DNA from Human Adenovirus Type 5," J. Gen Virol. 36(1):59-72 (1977).

Grines et al., "A Comparison of Immediate Angioplasty with Thrombolytic Therapy for Acute Myocardial Infarction," New Eng. J. Med. 328(10):673-679 (1993).

Grosskreutz et al., "Vascular Endothelial Growth Factor-Induced Migration of Vascular Smooth Muscle Cells in Vitro," Microvasc. Res. 58(2):128-136 (1999).

Grossniklaus et al., "Clinicopathologic Features of Surgically Excised Choroidal Neovascular Membranes," Ophthalmology 101(6):1099-1111 (1994).

Grossniklaus et al., "Macrophage and Retinal Pigment Epithelium Expression of Angiogenic Cytokines in Choroidal Neovascularization," Mol. Vis. 8:119-126 (2002).

Gruber et al., "Efficient tumor cell lysis mediated by a bispecific single chain antibody expressed in *Escherichia coli*," J. Immunol. 152(11):5368-5374 (1994).

Gryziewicz, "Regulatory Aspects of Drug Approval for Macular Degeneration," Adv. Drug Deliv. Rev. 57:2092-2098 (2005).

Gu et al., "In Vitro Activity of Dactimicin, a Novel Pseudodisaccharide Aminoglycoside, Compared with Activities of other Aminoglycosides," Antimicrob. Agents Chemother. 33(11):1998-2003 (1989).

Guillon et al., "Disruption of the Gene for Met-tRNA(fMet) Formyltransferase Severely Impairs Growth of *Escherichia coli*," J. Bacteriol. 174(13):4294-4301 (1992).

Guo et al., "Platelet-Derived Growth Factor-B Enhances Glioma Angiogenesis by Stimulating Vascular Endothelial Growth Factor Expression in Tumor Endothelia and by Promoting Pericyte Recruitment," Am. J. Pathol. 162(4):1083-1093 (2003).

Guss et al., "Structure of the IgG-binding regions of streptococcal protein G," EMBO J. 5(7):1567-1575 (1986).

Hageman et al., "A Common Haplotype in the Complement Regulatory Gene Factor H (HF1_CFH) Predisposes Individuals to Age-Related Macular Degeneration," Proc. Natl. Acad. Sci. USA 102(20):7227-7232 (2005).

Haimovitz-Friedman et al., "Ionizing Radiation Acts on Cellular Membranes to Generate Ceramide and Initiate Apoptosis," J. Exp. Med. 180(2):525-535 (1994).

Hajjar et al., "Prospects for Gene Therapy for Heart Failure," Circ. Res. 86(6):616-621 (2000).

Ham et al., "Media and Grown Requirements," Methods Enzmol. 58:44-93 (1979).

Hama et al., "Lysophosphatidic Acid and Autotaxin Stimulate Cell Motility of Neoplastic and Non-neoplastic Cells through LPA," J. Biol. Chem. 279(17):17634-17639 (2004).

Hammer et al., "Glucocorticoids Mediate Differential Anti-Apoptotic Effects in Human Fibroblasts and Keratinocytes via Sphingosine-1-Phosphate Formation," J. Cell. Biochem. 91(4):840-851 (2004).

Hanessian et al., "Aminoglycoside Antibiotics: Oxidative Degradations Leading to Novel Biochemical Probes and Synthetic Intermediates," J. Antibiot. (Tokyo) 28(10):835-837 (1975).

Hanselman et al., "A cDNA-Dependent Scintillation Proximity Assay for Quantifying Apolipoprotein A-I," J. Lipid Res. 38(11):2365-2373 (1997).

Harada et al., "The Role of Cytokines and Trophic Factors in Epiretinal Membranes: Involvement of Signal Transduction in Glial Cells," Prog. Retin. Eye Res. 25(2):149-164 (2006).

Harris et al., "Effect of Pegylation on Pharmaceuticals," Nat. Rev. Drug Disc. 2(3):214-221 (2003).

Hashimoto et al., "Lysophosphatidic Acid (LPA) Induces Plasma Exudation and Histamine Release in Mice via LPA Receptors," J. Pharmacol. Sci. 100(1):82-87 (2006).

Hayashi et al., "Phenotypic Modulation of Vascular Smooth Muscle Cells Induced by Unsaturated Lysophosphatidic Acids," Circ. Res. 89(3):251-258 (2001).

Hegde et al., "CD4+ T-Cell—Mediated Mechanisms of Corneal Allograft Rejection: Role of Fas-Induced Apoptosis," Transplantation 79(1):23-31 (2005).

Heim et al., "Engineering Green Fluorescent Protein for Improved Brightness, Longer Wavelengths and Fluorescence Resonance Energy Transfer," Curr. Biol. 6(2):178-182 (1996).

Heymans et al., "Loss or Inhibition of uPA or MMP-9 Attenuates LV Remodeling and Dysfunction after Acute Pressure Overload in Mice," Am. J. Pathol. 166(1):15-25 (2005).

Hla, "Physiological and Pathological Actions of Sphingosine 1-Phosphate," Semin. Cell Dev. Biol. 15(5):513-520 (2004).

Hobbs Dewitt et al., "'Diversomers': An Approach to Nonpeptide, Nonoligomeric Chemical Diversity," Proc. Nat. Acad. Sci. USA 90(15):6909-6913 (1993).

Hochlowski et al., "Phenelfamycins, A Novel Complex of Elfamycin-Type Antibiotics. II. Isolation and Structure Determination," J. Antibiot. (Tokyo) 41(10):1300-1315 (1988).

Hollinger et al., ""Diabodies:" Small bivalent and bispecific antibody fragments," Proc. Natl. Acad. Sci. USA 90(14):6444-6448 (1993).

Holmes et al., "Scar Remodeling and Transmural Deformation after Infarction in the Pig," Circulation 90(1):411-420 (1994).

Hoogenboom et al., "By-passing immunisation. Human antibodies from synthetic repertoires of germline VH gene segments rearranged in vitro," J. Mol. Biol. 227(2):381-388 (1991).

Horkko et al. "Antiphospholipid Antibodies are Directed against Epitopes of Oxidized Phospholipids. Recognition of Cardiolipin by Monoclonal Antibodies to Epitopes of Oxidized low density Lipoprotein," J. Clin. Invest. 98(3):815-825 (1996).

Hotta et al., "The Novel Enzymatic 3'-N-Acetylation of Arbekacin by an Aminoglycoside 3-N-Acetyltransferase of Streptomyces Origin and the Resulting Activity," J. Antibiot. (Tokyo) 51(8):735-742 (1998).

Hueber et al., "Basic Fibroblast Growth Factor mRNA, bFGF Peptide and FGF Receptor in Epiretinal Membranes of Intraocular Proliferative Disorders (PVR and PDR)," Int. Ophthalmol. 20(6):345-350 (1996).

Hughes et al., "Characterization of Smooth Muscle Cell and Pericyte Differentiation in the Rat Retina In Vivo," Investigat. Ophthalmol. Vis. Sci. 45(8):2795-2806 (2004).

Hwang et al., "Hepatic uptake and degradation of unilamellar sphingomyelin-cholesterol liposomes: A kinetic study," Proc. Natl. Acad. Sci. USA 77(7):4030-4034 (1980).

Igarashi et al., "Sphingosine 1-Phosphate and Isoform-specific Activation of Phosphoinositide 3-Kinase Beta," J. Biol. Chem. 276(39):36281-36288 (2001).

Igarashi et al., "VEGF Induces S1P1 Receptors in Endothelial Cells: Implications for Cross-Talk between Sphingolipid and Growth Factor Receptors," Proc. Natl. Acad. Sci. USA. 100(19):10664-10669 (2003).

Ikeda et al., "Biological Activities of novel Lipid Mediator Sphingosine 1-Phosphate in Rat Hepatic Stellate Cells," Am J. Physiol. Gastrointest. Liver Physiol. 279(2):G304-G310 (2000).

Ing et al., "Ten-year Postoperative Results of Penetrating Keratoplasty," Ophthalmology 105(10):1855-1865 (1998).

Inouye et al., "A Novel Aminoglycoside Antibiotic, Substance SF-2052," J. Antibiot. (Tokyo) 32(12):1354-1356 (1979).

Ishibashi et al., "Pericytes of Newly Formed Vessels in Experimental Subretinal Neovascularization," Arch. Ophthalmol. 113(2):227-231 (1995).

Isobe et al., "Early Detection of Rejection and Assessment of Cyclosporine Therapy by 111In Antimyosin Imaging in Mouse Heart Allografts," Circulation 84(3):1246-1255 (1991).

Jackson et al., "Phenelfamycins, a Novel Complex of Elfamycin-type Antibiotics. I. Discovery, Taxonomy and Fermentation," J. Antibiot. (Tokyo) 41(10):1293-1299 (1988).

Jackson et al., "Altromycins, Novel Pluramycin-like Antibiotics. I. Taxonomy of the Producing Organism, Fermentation and Antibacterial Activity," J. Antibiot. (Tokyo). 43(3):223-228 (1990).

Jakobovits et al., "Germ-line transmission and expression of a human-derived yeast artificial-chromosome," Nature 362(6417):255-258(1993).

Jakobovits et al., "Analysis of homozygous mutant chimeric mice:Deletion of the immunoglobulin heavy-chain joining region blocks B-cell development and antibody production," Proc. Natl. Acad. Sci. USA 90(6):2551-2555 (1993).

Janda, "Tagged Versus Untagged Libraries: Methods for the Generation and Screening of Combinatorial Chemical Libraries," Proc. Natl. Acad. Sci. USA 91(23):10779-10785 (1994).

Janeway et al., Immunobiology, Fifth Edition, Garland Publishing (2001) (Electronic Table of Contents Only).

Jerdan et al., "Proliferative Vitreoretinopathy Membranes," Ophthalmology 96(6):801-810 (1989).

Jester et al., "Modulation of Cultured Corneal Keratocyte Phenotype by Growth Factors-Cytokines Control in Vitro Contractility and Extracellular Matrix Contraction," Exp. Eye Res. 77(5):581-592 (2003).

Johnson et al., "A Potential Role for Immune Complex Pathogenesis in Drusen Formation," Exp. Eye Res. 70(4):441-449 (2000) 43(3):223-228 (1990).

Jolly et al., "Transactivation of Sphingosine-1—Phosphate Receptors by Fc RI Triggering Is Required for Normal Mast Cell Degranulation and Chemotaxis," J. Exp. Med. 199(7):959-970 (2004).

Jolly et al, "Expression of SphK1 Impairs Degranulation and Motility of RBL-2H3 Mast Cells by Desensitizing S1P Receptors," Blood 105(12):4736-4742 (2005).

Jones et al., "Replacing the complementarity-determining regions in a human antibody with those from a mouse," Nature 321(6069):522-525 (1986).

Jones et al., "Pathological CNS Autoimmune Disease Triggered by Traumatic Spinal Cord Injury: Implications for Autoimmune Vaccine Therapy," J. Neurosci. 22(7):2690-2700 (2002).

Joosten et al., "Antibody Response Against Perlecan and Collagen Types IV and VI in Chronic Renal Allograft Rejection in the Rat," Am. J. Pathol. 160(4):1301-1310 (2002).

Jordan et al., "The Role of Neutrophils in Myocardial Ischemia—Reperfusion Injury," Cardiovasc. Res. 43(4):860-878 (1999).

Joussen et al., "Suppression of Fas-FasL-Induced Endothelial Cell Apoptosis Prevents Diabetic Blood—Retinal Barrier Breakdown in a Model of Streptozotocin-Induced Diabetes," FASEB J. 17(1):76-78 (2003).

Kabat, "Antibody Diversity Versus Antibody Complementarity," Pharmacol. Rev. 34(1):23-38 (1982).

Kang et al., "Serum Bioactive Lysophospholipids Prevent TRAIL-Induced Apoptosis Via PI3K-Akt-Dependent cFLIP Expression and Bad Phosphorylation," Cell Death Differ. 11(12):1287-1298 (2004).

Kappos et al., "Oral Fingolimod (FTY720) for Relapsing Multiple Sclerosis," New Eng. J. Med. 355(11):1124-1140 (2006).

Kaur et al., "Ocular Preparations: The Formulation Approach," Drug Dev. Ind. Pharm. 28(5):473-493 (2002).

Kawasaki et al., "Conjunctival Inflammation in the Chronic Phase of Stevens-Johnson Syndrome," Br. J. Ophthalmol. 84(10):1191-1193 (2000).

Kent et al., "Choroidal Neovascularization: A Wound Healing Perspective," Mol.Vis. 9:747-755 (2003).

Khachigan, "Early growth response-1 in cardiovascular pathobiology," Circ. Res. 98(2):186-191 (2006).

Kim et al., "Identification of Sphingomyelin Turnover as an Effector Mechanism for the Action of Tumor Necrosis Factor alpha and gamma-Interferon. Specific role in cell differentiation," J. Biol. Chem. 266(1):484-489 (1991).

Kimura et al., "Reciprocal Regulation between Nitric Oxide and Vascular Endothelial Growth Factor in Angiogenesis," Acta Biochim. Pol. 50(1):49-59 (2003).

Kinumaki et al., "Macrolide Antibiotics M-4365 produced by Micromonospora. II. Chemical Structures," J. Antibiot. (Tokyo) 30(6):450-454 (1977).

Kinzler et al., "Whole Genome PCR: Application to the Identification of Sequences bound by Gene Regulatory Protein," Nucl. Acids Res. 17(10):3645-3653 (1989).

Klein et al., "Complement Factor H Polymorphism in Age-Related Macular Degeneration," Science 308(5720):385-389 (2005).

Kohler et al., "Continuous Cultures of Fused Cells Secreting Antibody of Predefined Specificity," Nature 256(5517):495-497 (1975).

Kostelny et al., "Formation of a bispecific antibody by the use of leucine zippers," J. Immunol. 148(5):1547-1553 (1992).

Kozbor et al., "A human hybrid myeloma for production of human monoclonal antibodies," J. Immunol. 133(6):3001-3005 (1984).

Krag et al., "Excimer Laser Treatment of Pterygium," Acta Ophthalmol. (Copenh) 70(4):530-533 (1992).

Kria et al., "Growth Factors in Cultured Pterygium Fibroblasts: Immunohistochemical and ELISA analysis," Graefes Arch. Clin. Exp. Ophthalmol. 236(9):702-708 (1998).

Krown et al. "TNFα receptor Expression in Rat Cardiac Myocytes: TNFα Inhibition of L-type Ca2+ Current and Ca2+ Transients," FEBS Lett. 376(1-2):24-30 (1995).

Kugelman et al., "Letter: The Preparation of Garamine, a Novel Pseudodisaccharide from Sisomycin," J. Antibiot. (Tokyo) 26(7):394-395 (1973).

Kurian et al., "Retroviral vectors," J. Clin. Mol. Pathol. 53(4):173-176 (2000).

Kwon et al., "Sphingosine 1-Phosphate Protects Human Umbilical Vein Endothelial Cells from Serum-deprived Apoptosis by Nitric Oxide Production," J. Biol. Chem. 6(14):10627-10633 (2001).

La Cour et al., "Age-Related Macular Degeneration: Epidemiology and Optimal Treatment," Drugs Aging 19(2):101-133 (2002).

La Heij et al., "Basic Fibroblast Growth Factor, Glutamine Synthetase, and Interleukin-6 in Vitreous Fluid From Eyes With Retinal Detachment Complicated by Proliferative Vitreoretinopathy," Am. J. Ophthalmol. 134(3):367-375 (2002).

Lagerqvist et al., "Lower Threshold for Adenosine-Induced Chest Pain in Patients with Angina and Normal Coronary Angiograms," British Heart J. 68(9):282-285 (1992).

Lam et al., "Production and Isolation of Two Novel Esperamicins in a Chemically defined Medium," J. Antibiot. (Tokyo) 48(12):1497-1501 (1995).

Lamontagne et al., "Antagonism of Sphingosine-1-Phosphate Receptors by FTY720 Inhibits Angiogenesis and Tumor Vascularization," Cancer Res. 66(1):221-231 (2006).

Lee et al., "Sphingosine 1-Phosphate Induces Angiogenesis: Its Angiogenic Action and Signaling Mechanism in Human Umbilical Vein Endothelial Cells," Biochem. Biophys. Res. Comm. 264(3):743-750 (1999).

Lee et al., "Vascular Endothelial Cell Adherens Junction Assembly and Morphogenesis Induced by Sphingosine-1-Phosphate," Cell 99(3):301-312 (1999).

Lee et al., "Akt-Mediated Phosphorylation of the G Protein-Coupled Receptor EDG-1Is Required for Endothelial Cell Chemotaxis," Mol. Cell 8(3):693-704 (2001).

Lee et al., "Lysophosphatidic Acid Is a Major Regulator of Growth-Regulated Oncogene-alpha in Ovarian Cancer," Cancer Res. 66(5):2740-2748 (2006).

Levade et al., "Sphingolipid Mediators in Cardiovascular Cell Biology and Pathology," Circ. Res. 89(11):957-968 (2001).

Li et al., "Nonviral Gene Therapy: Promises and Challenges," Gene Ther. 7(1):31-34 (2000).

Liang et al., "Parallel Synthesis ans Screening of a Solid Phase Carbohydrate Library," Science 274(5292):1520-1522 (1996).

Liliom et al., "Growth Factor-Like Phospholipids Generated after Corneal Injury," Am. J. Physiol. 274(4):C1065-C1074 (1998).

Limaye et al., "Sphingosine Kinase-1 Enhances Endothelial Cell Survival through a PECAM-1—Dependent Activation of Pl-3K-Akt and Regulation of Bcl-2 Family Members," Blood 105(8):3169-3177 (2005).

Lindahl et al., "Pericyte Loss and Microaneurysm Formation in PDGF-B-Deficient Mice," Science 277(5323):242-245 (1997).

Lindmark et al., "Binding of immunoglobulins to protein A and immunoglobulin levels in mammalian sera," J. Immunol. Meth. 62(1):1-13 (1983).

Lingen, "Role of Leukocytes and Endothelial Cells in the Development of Angiogenesis in Inflammation and Wound Healing," Arch. Pathol. Lab Med. 125(1):67-71 (2001).

Liu et al., "A Review of Treatments for Macular Degeneration: A Synopsis of Currently Approved Treatments and Ongoing Clinical Trials," Curr. Opin. Ophthalmol.15(3):221-226 (2004).

Long et al., "The Functional PDGFB Receptor—S1P1 Receptor Signaling Complex is Involved in Regulating Migration of Mouse Embryonic Fibroblasts in Response to Platelet Derived Growth Factor," Prostaglandins. Other Lipid Med. 80(1-2):74-80 (2006).

Lowe et al., "Sphingosine Differentially Inhibits Activation of the Na+-H+exchange by Phorbol Esters and Growth Factors," J. Biol. Chem. 265(13):7188-7194 (1990).

Luberto et al., "Inhibition of Tumor Necrosis Factor-induced Cell Death in MCF7 by a Novel Inhibitor of Neutral Sphingomyelinase," J. Biol. Chem. 277(43):41128-41139 (2002).

Macaya et al., "Thrombin-Binding DNA Aptamer forms a Unimolecular Quadruplex Structure in Solution," Proc. Natl Acad. Sci. USA 90(8):3745-3749 (1993).

MacDonnell et al., "Depression of Excitability by Sphingosine 1-Phosphate in Rat Ventricular Myocytes," Am. J. Physiol.Heart Circ. Physiol. 275(6):H2291-H2299 (1998).

Marchini et al., "4-Demethoxy-3'-Deamino-3'-Aziridinyl-4'-Methylsulphonyl-Daunorubicin (PNU-159548), a Novel Anticancer Agent Active Against Tumor Cell Lines with Different Resistance Mechanisms," Cancer Res. 61(5):1991-1995 (2001).

Marcovich et al., "Angiogenesis in Pterygium: Morphometric and Immunohistochemical Study," Curr. Eye Res. 25(1):17-22 (2002).

Marks et al., "By-passing Immunization Human Antibodies from V-gene Libraries Displayed on Phage," J. Mol. Biol. 222(3):581-597 (1991).

Martin et al., "Irreversible Coupling of Immunoglobulin Fragments to Preformed Vesicles: An Improved Method for Liposome Targeting,"J. Biol. Chem. 257(1):286-288 (1982).

Martin et al., "Iontophoresis of Lysophosphatidic Acid into Rabbit Cornea Induces HSV-1 Reactivation: Evidence that Neuronal Signaling Changes after Infection," Mol. Vis. 5:36-42 (1999).

Massberg et al.,"Fingolimod and Sphingosine-1-Phosphate—Modifiers of Lymphocyte Migration," New Eng. J. Med. 355(11):1088-1091 (2006).

Mather, "Establishment and Characterization of Two Distinct Mouse Testicular Epithelial Cell Lines," Biol. Reprod. 23(1):243-252 (1980).

Matsuhashi et al., "In Vitro and In Vivo Antibacterial Activities of Dactimicin, a Novel Pseudodisaccharide Aminoglycoside, Compared with those of other Aminoglycoside Antibiotics," Antimicrob. Agents Chemother. 27(4):589-594 (1985).

Matsumoto et al., "Synthesis of Novel 13-Methyl-13-Dihydroanthracyclines," Chem. Pharm. Bull. (Tokyo) 34(11):4613-4619 (1986).

Matsunaga et al., "Bacterial Uptake of Habekacin, a Novel Aminoglycoside Antibiotic," J. Antibiot. (Tokyo) 37(5):596-601 (1984).

Matsuura et al., "Effect of FTY720, A Novel Immunosuppressant, on Adjuvant- and Collagen-Induced Arthritis in Rats," Int. J. Immunopharmacol. 22(4):323-331 (2000).

McCormick, "Anti-TGF-β Treatment Prevents Skin and Lung Fibrosis in Murine Sclerodermatous Graft-Versus-Host Disease: A Model for Human Scleroderma," J. Immunol. 163(10):5693-5699 (1999).

McDonough et al. "Control of Cardiac Ca2+ levels: Inhibitory Actions of Sphingosine on Ca2+ Transients and L-type Ca2+ Channel Conductance," Circ. Res. 75(6):981-989 (1994).

Meldrum et al., "Increased Myocardial Tumor Necrosis Factor—in a Crystalloid-Perfused Model of Cardiac Ischemia-Reperfusion Injury," Ann. Thorac. Surg. 65(2):439-443 (1998).

Merrifield, "Solid Phase Peptide Synthesis. I. The Synthesis of a Tetrapeptidem," J. Am. Chem. Soc. 85(14):2149-2154 (1964).

Miller et al., "Clinical Pharmacology and Toxicity of 4'-O-Tetrahydropyranyladriamycin," Cancer Res. 47(5):1461-1465 (1987).

Milstien et al., "Targeting Sphingosine-1-Phosphate: A Novel Avenue for Cancer Therapeutics," Cancer Cell 9(3):148-150 (2006).

Monahan et al., "AAV Vectors: is Clinical Success on the Horizon?," Gene Ther. 7(1):24-30 (2000).

Moolenaar, "Bioactive Lysophospholipids and Their G Protein-Coupled Receptors," Exp. Cell Res. 253(1):230-238 (1999).

Matsuura et al., "Effect of FTY720, A Novel Immunosuppressant, on Adjuvant- and Collagen-Induced Arthritis in Rats," Int. J. Immunopharmacol. 22(4):323-331 (2000).

Moolenaar et al., "The Ins and Outs of Lysophosphatidic Acid Signaling," BioEssays 26(8):870-881 (2004).

Morea et al., "Antibody Modeling: Implications for Engineering and Design," Methods 20(3):267-279 (2000).

Morimoto et al., "Single-step purification of F(ab')2 fragments of mouse monoclonal antibodies (immunoglobulins G1) by hydrophobic interaction high-performance liquid chromatography using TSKgel Phenyl-5PW," J. Biochem. Biophys. Methods 24(1-2):107-117 (1992).

Morrison et al., "Chimeric Human Antibody Molecules: Mouse Antigen-Binding Domains with Human Constant Region Domains," Proc. Natl. Acad. Sci. USA 81(21):6851-6855 (1984).

Moulin, "The Clinical Management of Neoropathic Pain," Pain Res. Manag. 11(Suppl A):30A-36A (2006).

Munson et al., "LIGAND: A versatile computerized approach for characterization of ligand-binding systems," Anal. Biochem. 107(1):220-239 (1980).

Murali-Krishna et al., "Counting Antigen-Specific CD8 T Cells: A Reevaluation of Bystander Activation during Viral Infection," Immunity 8(2):177-187 (1998).

Mutsch et al., "Success Criteria and Success Rates in Trabeculectomy with and without Intraoperative Antimetabolites using Intensified Postoperative Care (IPC)," Graefe Arch. Clin. Exp. Ophthalmol. 238(11):884-891 (2000).

Myles et al., "Recent Progress in Ocular Drug Delivery for Posterior Segment Disease: Emphasis on Transscleral Iontophoresis," Adv. Drug Deliv. Rev. 57(14):2063-2079 (2005).

Nagineni et al., "Expression of PDGF and Their Receptors in Human Retinal Pigment Epithelial Cells and Fibroblasts: Regulation by TGF-B" J. Cell. Physiol. 203(1):35-43 (2005).

Netto et al., "Wound Healing in the Cornea," Cornea 24(5):509-522 (2005).

Neuberger et al., "Recombinant antibodies possessing novel effector functions," Nature 312(5995):604-608 (1984).

Newton et al., "Formylation Is Not Essential for Initiation of Protein Synthesis in All Eubacteria," J. Biol. Chem. 274(32):22143-22146 (1999).

Nickenig et al., "Statin-Sensitive Dysregulated AT1 Receptor Function and Density in Hypercholesterolemic Men," Circulation 100(21):2131-2134 (1999).

Norata et al., "High-Density Lipoproteins Induce Transforming Growth Factor-β2 Expression in Endothelial Cells," Circulation 111(21):2805-2811 (2005).

O'Sullivan et al., "Methods for the Preparation of Enzyme-Antibody Conjugates for use in Enzyme Immunoassay," Methods Enzymol. 73(Pt. B):147-166 (1981).

Ogretmen et al., "Biologically active sphingolipids in cancer pathogenesis and treatment," Nat. Rev. Cancer 4(8):604-616 (2004).

Oh et al., "The Potential Angiogenic Role of Macrophages in the Formation of Choroidal Neovascular Membranes," Invest. Ophthalmol. Vis. Sci. 40(9):1891-1898 (1999).

Ohashi et al., "In Vitro and In Vivo Antibacterial Activity of KW1070, a New Aminoglycoside Antibiotic," Antimicrob. Agents Chemother. 17(2):138-143 (1980).

Okachi et al., "Fortimicins A and B, New Aminoglycoside Antibiotics. II. Isolation, Physico—Chemical and Chromatographic Properties," J. Antibiot. (Tokyo) 30(7):541-551 (1977).

Olivera et al., "Sphingosine Kinase Expression Increases Intracellular Sphingosine-1-Phosphate and Promotes Cell Growth and Survival," J. Cell Biol. 147(3):545-558 (1999).

Olivera, "Sphingolipids and the Balancing of Immune Cell Function: Lessons from the Mast Cell," J. Immunol. 174(3):1153-1158 (2005).

Otani et al., "Expressions of Angiopoietins and Tie2 in Human Choroidal Neovascular Membranes," Invest. Ophthalmol. Vis. Sci. 40(9):1912-1920 (1999).

Padmanabhan et al., "The Structure of a-Thrombin Inhibited by a 15-Mer Single-stranded DNA Aptamer," J. Biol. Chem. 268(24):17651-17654 (1993).

Paik et al., "Sphingosine 1-Phosphate Receptor Regulation of N-Cadherin Mediates Vascular Stabilization," Genes Dev. 18(19):2392-2403 (2004).

Palinski et al. "Cloning of Monoclonal Autoantibodies to Epitopes of Oxidized Lipoproteins from Apolipoprotein E-deficient Mice (Demonstration of Epitopes of Oxidized Low Density Lipoprotein in Human Plasma)," J. Clin. Invest, 98(3):800-814 (1996).

Parrill et al., "Identification of Edg1 Receptor Residues That Recognize Sphingosine 1-Phosphate," J. Biol. Chem. 275(50):39379-39384 (2000).

Pauleikhoff, "Neovascular Age-Related Macular Degeneration: Natural History and Treatment Outcomes," Retina 25(8):1065-1084 (2005).

Pelyvas et al., "Synthesis of New Pseudodisaccharide Aminoglycoside Antibiotics from Carbohydrates," J. Antibiot. (Tokyo) 48(7):683-695 (1995).

Perzynski et al., "Effects of Apramycin, A Novel Aminoglycoside Antibiotic on Bacterial Protein Synthesis," Eur. J. Biochem. 99(3):623-628 (1979).

Peters et al., "Selective Lymphocyte Inhibition by FTY720 slows the Progressive Course of Chronic Anti-Thy 1 Glomerulosclersis," Kidney Int. 66(4):1434-1443 (2004).

Phillipson et al., "Lanomycin and Glucolanomycin, Antifungal Agents Produced by *Pycnidiophora dispersa*. II. Structure Elucidation," J. Antibiot. (Tokyo) 45(3):313-319 (1992).

Planck et al., "Expression of Growth Factor mRNA in Rabbit PVR Model Systems," Curr. Eye Res. 11(11):1031-1039 (1992).

Ponder, "Systemic Gene Therapy for Cardiovascular Disease," Trends Cardiovasc. Med. 9(6):158-162 (1999).

Pournaras et al., "Myofibroblasts and Epiretinal Membranes," Klin. Monatsbl. Fur Augenheilkd. 212(5):356-358 (1998) (English Abstract Only).

Presta, "Antibody Engineering," Curr. Opin. Struct. Biol. 2(6):593-596 (1992).

Priebe et al., "3'-Hydroxyesorubicin. Synthesis and Antitumor Activity," J. Antibiot. (Tokyo) 43(7):838-846 (1990).

Pyne et al., "Sphingosine 1-Phosphate Signalling in Mammalian Cells," Biochem. J. 349(Pt. 2):385-402 (2000).

Queen et al., "A Humanized Antibody that Binds to the Interleukin 2 Receptor," Proc. Natl. Acad. Sci. USA 86(24):10029-10033 (1989).

Radeff-Huang et al., "G Protein Mediated Signaling Pathways in Lysophospholipid Induced Cell Proliferation and Survival," J. Cell. Biochem. 92(5):949-966 (2004).

Rao et al., "Expression of Nonphagocytic NADPH Oxidase System in the Ocular Lens," Mol. Vis. 10:112-121 (2004).

Razzaque et al., "Role of Macrophage Migration Inhibitory Factor in Conjunctival Pathology in Ocular Cicatricial Pemphigoid," Invest. Ophthalmol. Vis. Sci. 45(4):1174-1181 (2004).

Reza et al., "Anti-Idiotypic Monoclonal Antibody Recognizes a Consensus Recognition Site for Phosphatidylserine in Phosphatidylserine-Specific Monoclonal Antibody and Protein Kinase C," FEBS Lett. 339(3):229-233 (1994).

Rikitake et al., "Involvement of Endothelial Nitric Oxide in Sphingosine-1-Phosphate-Induced Angiogenesis," Arterioscler. Thromb. Vasc. Biol. 22(1):108-114 (2002).

Robaye et al., "Tumor necrosis factor induces apoptosis (programmed cell death) in normal endothelial cells in vitro," Am. J. Pathol. 138(2):447-453 (1991).

Robbins et al., "Platelet-Derived Growth Factor Ligands and Receptors Immunolocalized in Proliferative Retinal Diseases," Invest. Ophthalmol. Vis. Sci. 35(10):3649-3663 (1994).

Rosen et al., "Sphingosine 1-Phosphate and its Receptors: An Autocrine and Paracrine Network," Nat. Rev. Immunol. 5(7):560-570 (2005).

Rosenfeld et al., "Ranibizumab for Neovascular Age-Related Macular Degeneration," New Eng.J. Med. 355(14):1419-1431 (2006).

Saika et al., "Loss of Tumor Necrosis Factor α Potentiates Transforming Growth Factor B-mediated Pathogenic Tissue Response during Wound Healing," Am. J. Pathol. 168(6):1848-1860 (2006).

Saishin et al., "VEGF-TRAPR1R2 Suppresses Choroidal Neovascularization and VEGF-Induced Breakdown of the Blood-Retinal Barrier," J. Cell. Physiol. 195(2):241-248 (2003).

Saitoh et al., "Boholmycin, A New Aminoglycoside Antibiotic. I. Production, Isolation and Properties," J. Antibiot. (Tokyo) 41(7):855-861 (1988).

Sanchez et al., "Phosphorylation and Action of the Immunomodulator FTY720 Inhibits Vascular Endothelial Cell Growth Factor-induced Vascular Permeability," J. Biol. Chem. 278(47):47281-47290 (2003).

Scherer et al., "Sphingosine-1-phosphate modulates spiral modiolar artery tone: A potential role in vascular-based inner ear pathologies?," Cardiovasc. Res. 70(1):79-87 (2006).

Schnitzer et al., "Segmental Differentiation of Permeability, Protein Glycosylation, and Morphology of Cultured Bovine Lung Vascular Endothelium," Biochem. Biophys. Res. Comm. 199(1):11-19 (1994).

Schottenfeld et al., "Chronic Inflammation: A Common and Important Factor in the Pathogenesis of Neoplasia," CA Cancer J. Clin. 56(2):69-83 (2006).

Schwab et al., "Lymphocyte Sequestration Through S1P Lyase Inhibition and Disruption of S1P Gradients," Science 309(5741):1735-1739 (2005).

Seddon et al., "The Epidemiology of Age-Related Macular Degeneration," Int. Ophthalmol. Clin. 44(4):17-39 (2004).

Sedlakova et al., "FTY720 in Corneal Concordant Xenotransplantation," Transplantation 79(3):297-303 (2005).

Ségui et al., "Involvement of FAN in TNF-induced apoptosis," J. Clin. Invest. 108(1):143-151 (2001).

Sena-Esteves et al., "HSV-1 Amplicon Vectors—Simplicity and Versatility," Mol. Ther. 2(1):9-15 (2000).

Shalaby et al., "Development of Humanized Bispecific Antibodies Reactive with Cytotoxic Lymphocytes and Tumor Cells Overexpressing the HER2 Protooncogene," J. Exp. Med. 175(1):217-225 (1992).

Shaunak et al., "Site-Specific PEGylation of Native Disulfide Bonds in Therapeutic Proteins," Nat. Chem. Biol. 2(6):312-313 (2006).

Simon et al., "Peptoids: A Modular Approach to Drug Discovery," Proc. Natl. Acad. Sci. USA 89(20):9367-9371 (1992).

Simon et al., "Lysophosphatidic Acid Inhibits Adipocyte Differentiation via Lysophosphatidic Acid 1 Receptor-dependent Down-regulation of Peroxisome Proliferator-activated Receptor γ2," J. Biol. Chem. 280(15):14656-14662 (2005).

Sinnaeve et al., "Gene Therapy in the Cardiovascular System: An Update," Cardiovasc. Res. 44(3):498-506 (1999).

Sivalingam et al., "Basic Fibroblast Growth Factor Levels in the Vitreous of Patients with Proliferative Diabetic Retinopathy," Arch. Ophthalmol. 108(6):869-872 (1990).

Smith et al., "Purified Fumonisin B1 Decreases Cardiovascular Function but Does Not Alter Pulmonary Capillary Permeability in Swine," Toxicol. Sci. 56(1):240-249 (2000).

Sotozono et al., "Cytokine Expression in the Alkali-Burned Cornea," Curr. Eye Res. 16(7):670-676 (1997).

Spiegel et al., "Sphingosine-1-Phosphate as a Therapeutic Agent," Leukemia 16(9):1596-1602 (2002).

Spiegel et al. "Sphingosine-1-Phosphate an Enigmatic Signalling Lipid," Nat. Rev. Mol. Cell Biol. 4(5):397-407 (2003).

Squires et al., "Altered Fibroblast Function following Myocardial Infarction," J. Mol. Cell. Cardiol. 39(4):699-707 (2005).

Stavri et al., "Basic Fibroblast Growth Upregulates the Expression of Vascular Endothelial Growth Factor in Vascular Smooth Muscle Cells," Circulation 92(1):11-14 (1995).

Stephan et al., "Gene Therapy for Coronary Disease," Ann. Endocrinol. (Paris) 61(1):85-90 (2000) (English Abstract Only).

Stramer et al., "Molecular Mechanisms Controlling the Fibrotic Repair Phenotype in Cornea: Implications for Surgical Outcomes," Invest. Ophthalmol. Vis. Sci. 44(10):4237-4246 (2003).

Strom et al., "Effect of Ruboxistaurin on Blood-Retinal Barrier Permeability in Relation to Severity of Leakage in Diabetic Macular Edema," Invest. Ophthalmol. Vis. Sci. 46(10): 3855-8 (2005).

Su et al., "Sphingosine 1-Phosphate, a Novel Signaling Molecule, Stimulates DNA Binding Activity of AP-1 in Quiescent Swiss 3T3 Fibroblasts," J. Biol. Chem. 269(23):16512-1651, (1994).

Sun et al., "Angiotensin Converting Enzyme and Myofibroblasts during Tissue Repair in the Rat Heart," J. Mol. Cell. Cardiol. 28(5):851-858 (1996).

Sun et al., "Infarct Scar: A Dynamic Tissue," Cardiovasc. Res. 46(2):250-256 (2000).

Sunada et al., "Acetylation of Aminoglycoside Antibiotics with 6'-Methylamino Group, Istamycin B and Micronomicin, by a Novel Aminoglycoside 6'-Acetyltransferase of Actinomycete Origin," J. Antibiot. (Tokyo) 53(12):1416-1419 (2000).

Suomalainen et al., "Sphingosine-1-Phosphate Inhibits Nuclear Factor κB Activation and Germ Cell Apoptosis in the Human Testis Independently of Its Receptors," Am. J. Pathol. 166(3):773-781 (2005).

Suzuki et al., "Preparation and Some Microbiological Properties of Novel Kanamycin-Glucoside Derivatives," J. Antibiot. (Tokyo) 32(7):753-755 (1979).

Svetlov et al., "EDG receptors and hepatic Pathophysiology of LPA and S1P: EDG-ology of Liver Injury," Biochim. Biophys. Acta 1582(1-3):251-256 (2002).

Takahashi et al., "Production of Novel Antibiotic, Dopsisamine, by a New Subspecies of *Nocardiopsis mutabilis* with Multiple Antibiotic Resistance," J. Antibiot. (Tokyo) 39(2):175-183 (1986).

Tanaka, "Effects of Habekacin, A Novel Aminoglycoside Antibiotic, on Experimental Corneal Ulceration due to *Pseudomonas aeruginosa*," J. Antibiot. (Tokyo) 34(7):892-897 (1981).

Tanaka et al., "Mechanism of Action of Habekacin, A Novel Amino Acid-Containing Aminoglycoside Antibiotic," Antimicrobi. Agents Chemoth. 24(5):797-802 (1983).

Tanimoto et al., "Transactivation of Vascular Endothelial Growth Factor (VEGF) Receptor Flk-1-KDR Is Involved in Sphingosine 1-Phosphate-stimulated Phosphorylation of Akt and Endothelial Nitric-oxide Synthase (eNOS)," J. Biol. Chem. 277(45):42997-43001 (2002).

Tezel et al., "Pathogenesis of Age-Related Macular Degeneration," TRENDS Mol. Med. 10(9):417-420 (2004).

Tomasek et al., "Myofibroblasts and Mechano-Regulation of Connective Tissue Remoldeling," Nat. Rev. Mol. Cell Biol. 3(5):349-363 (2002).

Tonnetti et al., "A Role for Neutral Sphingomyelinase-mediated Ceramide Production in T Cell Receptor-induced Apoptosis and Mitogen-activated Protein Kinase-mediated Signal Transduction," J. Exp. Med. 189(10):1581-1589 (1999).

Torre-Amione et al, "Expression and Functional Significance of Tumor Necrosis Factor Receptors in Human Myocardium," Circulation 92(6):1487-1493 (1995).

Trautmann et al, "Mast Cell Involvement in Normal Human Skin Wound Healing: Expression of Monocyte Chemoattractant Protein-1 is Correlated with Recruitment of Mast Cells which Synthesize Interleukin-4 In Vivo," J. Pathol. 190(1):100-106 (2000).

Trentham et al, "Autoimmunity to Type II Collagen an Experimental Model of Arthritis," J. Exp. Med. 146(3):857-868 (1977).

Treston et al., "Biochemical Characterization of Peptide Alpha-Amidation Enzyme Activities of Human Neuroendocrine Lung Cancer Cell Lines," Cell Growth Differ. 4(11):911-920 (1993).

Trono, "Lentiviral Vectors: Turning a Deadly Foe into a Therapeutic Agent," Gene Ther. 7(1):20-23 (2000).

Tsunakawa et al., "Inosamycin, A Complex of New Aminoglycoside Antibiotics. I. Production, Isolation and Properties," J. Antibiot. (Tokyo) 38(10):1302-1312 (1985).

Tsutsumi et al., "The Critical Role of Ocular-Infiltrating Macrophages in the Development of Choroidal Neovascularization," J. Leukoc. Biol. 74(1):25-32 (2003).

Tuerk et al., "Systematic Evolution of Ligands by Exponential Enrichment: RNA Ligands to Bacteriophage T4 DNA Polymerase," Science 249(4968):505-510 (1990).

Tutt et al., "Trispecific F(ab')3 derivatives that use cooperative signaling via the TCR-CD3 complex and CD2 to activate and redirect resting cytotoxic T cells," J. Immunol. 147(1):60-69 (1991).

Ueno et al., "Accelerated Wound Healing of Alkali-Burned Corneas in MRL Mice Is Associated with a Reduced Inflammatory Signature" Invest. Ophthalmol. Vis. Sci. 46(11):4097-4106 (2005).

Urata et al., "Sphingosine 1-Phosphate Induces A-Smooth Muscle Actin Expression in Lung Fibroblasts via Rho-kinase," Kobe J. Med. Sci. 51(1):17-27 (2005).

Urban et al., "Comparative In-Vitro Activity of SCH 27899, a Novel Everninomicin, and Vancomycin," J. Antimicrob. Chemother. 37(2):361-364 (1996).

Urlaub et al., "Isolation of Chinese hamster cell mutants deficient in dihydrofolate reductase activity," Proc. Natl. Acad. Sci. USA 77(7):4216-4220 (1980).

Usui et al., "Blood Lipid Mediator Sphingosine 1-Phosphate Potently Stimulates Platelet-derived Growth Factor-A and -B Chain Expression through S1P1-Gi-Ras-MAPK-dependent Induction of Krüppel-like Factor 5," J. Biol. Chem. 279(13):12300-12311 (2004).

Vadas et al., "Endothelial Adhesion Molecules in Atherogenesis A Concerto or a Solo?," Circ. Res. 79(6):1216-1217 (1996).

Van Brocklyn et al., "Dual Actions of Sphingosine-1-Phosphate: Extracellular through the Gi-coupled Receptor Edg-1 and Intracellular to Regulate Proliferation and Survival," J. Cell Biol. 142(1):229-240 (1998).

Van Craenenbroeck et al., "Episomal Vectors for Gene Expression in Mammalian Cells" Eur. J. Biochem. 267(18):5665-5678 (2000).

Van Leeuwen et al., "Lysophosphatidic Acid: Mitogen and Motility Factor," Biochem. Soc. Trans. 31(Pt 6):1209-1212 (2003).

Van Meeteren et al., "Autotaxin, a Secreted Lysophospholipase D, Is Essential for Blood Vessel Formation during Development," Mol. Cell Biol. 26(13):5015-5022 (2006).

Van Wijngaarden et al., "Inhibitors of Ocular Neovascularization: Promises and Potential Problems," J. Am. Med. Assoc. 293(12):1509-1513 (2005).

Vekich et al., "Tumorigenic and angiogenic effects of S1P mAb in multiple murine models of cancer," Proceedings of the American Association for Cancer Research Annual Meeting 46:557 (2005) (Abstract Only).

Verma et al., "Chemokines in Acute Anterior Unveitis," Curr. Eye Res. 16 (12):1202-1208 (1997).

Vidinova et al., "Ultrastrukturelle Veränderungen in der Struktur epiretinaler Membranen bei PVR—Anspruch und Wirklichkeit [Alterations in the Structure of the Epiretinal Membranes in PVR—Assumptions and Reality]," Klin Monatsbl. Augenheilkd. 222(7):568-571 (2005) (English Abstract Only).

Vinores et al., "Experimental Models of Growth Factor-Mediated Angiogenesis and Blood-Retinal Barrier Breakdown," Gen. Pharmacol. 35(5):233-239 (2000).

Virag et al., "Myofibroblast and Endothelial Cell Proliferation during Murine Myocardial Infarct Repair," Am. J. Pathol. 163(6):2433-2440 (2003).

Visentin et al., "Validation of an anti-sphingosine-1-phosphate antibody as a potential therapeutic in reducing growth, invasion, and angiogenesis in multiple tumor lineages," Cancer Cell, 9(3):225-238 (2006).

Waitz et al., "Biological Activity of Sch 14342, an Aminoglycoside Antibiotic Coproduced in the Gentamicin Fermentation," Antimicrob. Agents Chemother. 2(6):464 (1972).

Wang et al., "Sphingosine-1-phosphate inhibits motility of human breast cancer cells independently of cell surface receptors," Cancer Res. 59(24):6185-6191 (1999).

Wang et al., "Sphingosine 1-Phosphate Stimulates Cell Migration through a Gi-coupled Cell Surface Receptor," J. Biol. Chem. 274(50):35343-35350 (1999).

Wang et al., "In Vivo Activity and Pharmacokinetics of Ziracin (SCH27899), a New Long-Acting Everninomicin Antibiotic, in a Murine Model of Penicillin-Susceptible or Pneumococcal Pneumonia," Antimicrob. Agents Chemother. 44 (4):1010-1018 (2000).

Weinstein et al., "Antibiotic 6640, A New Micromonospora-Produced Aminoglycoside Antibiotic," J. Antibiot. (Tokyo) 23(11):551-554 (1970).

Wells, "Eek, a XenoMouse: Abgenix, Inc.," Chem. Biol. 7(8):R185-R186 (2000).

Witmer et al., "Vascular EndothelialGrowth Factors and Angiogenesis in Eye Disease," Prog. Retin. Eye Res. 22(1):1-29 (2003).

Wu et al., "Lysophospholipids Enhance Matrix Metalloproteinase-2 Expression in Human Endothelial Cells," Endocrinology 146(8):3387-3400 (2005).

Xia et al., "An oncogenic role of sphingosine kinase," Curr. Biol. 10 (23):1527-1530 (2000).

Yamagami et al., "Early Ocular Chemokine Gene Expression and Leukocyte Infiltration after High-Risk Corneal Transplantation," Mol. Vis. 11:632-640 (2005).

Yamakage et al., "Selective Upregulation of Platelet-Derived Growth Factor α Receptors by Transforming Growth Factor β in Scleroderma Fibroblasts," J. Exp. Med. 175 (5):1227-1234 (1995).

Yamamoto et al., "Vitrectomy for Diabetic Macular Edema: The Role of Posterior Vitreous Detachment and Epimacular Membrane," Am. J. Ophthalmol. 132(3):369-377 (2001).

Yamanaka et al., "Sphingosine Kinase 1 (SPHK1) Is Induced by Transforming Growth Factor-β and Mediates TIMP-1 Up-regulation," J. Biol. Chem. 279(52):53994-54001 (2004).

Yanaga et al., "Tumor necrosis factor α stimulates sphingomyelinase through the 55 kDa receptor in HL-60 cells," FEBS Lett. 314(3):297-300 (1992).

Yasuda et al., "Total Synthesis of 3-0-Demethylsporaricin A," J. Antibiot. (Tokyo) 38(11):1512-1525 (1985).

Yatomi et al., "Sphingosine 1-Phosphate as a Major Bioactive Lysophospholipid that is Released from Platelets and Interacts with Endothelial Cells," Blood 96(10):3431-3438 (2000).

Zager et al., "Altered Ceramide and Sphingosine Expression during the Induction Phase of Ischemic Acute Renal Failure," Kidney Int. 52(1):60-70 (1997).

Zapata et al. "Engineering linear F(ab')2 fragments for efficient production in Escherichia coli and enhanced antiproliferative activity," Protein Eng. 8(10):1057-1062 (1995).

Zarbin, "Current Concepts in the Pathogenesis of Age-Related Macular Degeneration," Arch. Ophthalmol. 122(4):598-614 (2004).

Zhang et al., "Sphingosine-1-phosphate, a novel lipid, involved in cellular proliferation," J. Cell Biol. 114(1):155-167 (1991).

Zhang et al., "Editorial: Signaling, through the Sphingomyelin Pathway," Endocrinology 136(10):4157-4160 (1995).

Zhang et al., "Sphingosine 1-Phosphate Stimulates Fibronectin Matrix Assembly Through a Rho-Dependent Signal Pathway," Blood 93(9):2984-2990 (1999).

Zhang et al., "Significant Prolongation of Orthotopic Corneal-Graft Survival in FTY720-Treated Mice," Transplantation 76(10):1511-1513 (2003).

Zheng et al., "Platelet-derived Growth Factor Receptor Kinase Inhibitor AG1295 and Inhibition of Experimental Proliferative Vitreoretinopathy," Jpn. J. Ophthalmol. 47(2):158-165 (2003).

Zhu et al., "Both Apolipoprotein E and Immune Deficiency Exacerbate Neointimal Hyperplasia After Vascular Injury in Mice," Arterioscler. Thromb. Vasc. Biol. 22(3):450-455 (2002).

Abe et al., "Structural and stereochemical studies of potent inhibitors and glucosylceramide synthase and tumor cell growth," J. Lipid Res. 36(3):611-621 (1995).

Abe et al., "Glycosphingolipid depletion in Fabry disease lymphoblasts with potent inhibitors of glucosylceramide synthase," Kidney Int. 57(2):446-454 (2000).

Abe et al., "Use of Sulfobutyl Ether-Cyclodextrin as a Vehicle for D-threo-1-Phenyl-2-decanoylamino-3-morpholinopropanol-Related Glucosylceramide Synthase Inhibitors," Anal. Biochem. 287(2):344-347 (2000).

Ambati, "Age-related macular degeneration: etiology, pathogenesis, and therapeutic strategies," Surv. Ophthalmol. 48(3):257-293 (2003) (Abstract Only).

An et al., "Identification of cDNAs encoding two G protein-coupled receptors for lysosphingolipids," FEBS Letts. 417(3):279-282 (1997).

An et al., "Characterization of a Novel Subtype of Human G Protein-coupled Receptor for Lysophosphotatidic Acid," J. Biol. Chem. 273(14):7906-7910 (1998).

An et al., "Sphingosine 1-phosphate-induced cell proliferation, survival, and related signaling events mediated by G protein-coupled receptors Edg3 and Edg5," J. Biol. Chem. 275(1):288-296 (2000).

Ancellin et al., "Extracelluar export of sphingosine kinase-1 enzyme: Sphingosine 1 phosphate generation and the induction of angiogenic vascular maturation," J. Biol. Chem. 277(8):6667-6675 (2001).

Andrieu-Abadie et al., "L-carnitine prevents doxorubicin-induced apoptosis of cardiac myocytes: role of inhibition of ceramide generation," FASEB J. 13(12):1501-1510 (1999).

Arenz et al., "Synthese des ersten selektiven irreverilben Inhibitors der neutralen Sphingomyelinase," Angew Chem. 112:1498-1500 (2000) (German); "Synthesis of the First Selective Irreversible Inhibitor of Neutral Sphingomyelinase," Angew. Chem. Int. Ed. 39(8):1440-1442 (2000) (English Equivalent).

Arenz et al., "Manumycin A and its Analogues Are Irreversible Inhibitors of Neutral Sphingomyelinase," Chem. Biochem. 2(2):141-143 (2001).

Arenz et al., "Synthesis and Biochemical Investigation of Scyphostatin Analogues as Inhibitors of Neutral Sphingomyelinase," Bioorg. Medicinal Chem. 9(11):2901-2904 (2001).

Arenz et al., "Synthesis of the First Selective Irreversible Inhibitor of Neutral Sphingomyelinase," Eur. J. Org. Chem. 2001(1):137-140 (2001).

Ariga et al., "Role of Sphingolipid-mediated cell death in neurodegenerative diseases," J. Lip. Res. 39(1):1-16 (1998).

Bajjalieh et al., "Ceramide Kinase," Methods Enzymol. 311:207-215 (1999).

Barbone et al., "Robotic Assay of Sphingomyelinase Activity for High Throughput Screening," Meth. Enzymol. 311:168-176 (1999).

Bawab et al., "Molecular Clonging and Characterization of a Human Mitochondrial Ceramidase," J. Biol. Chem. 275(28):21508-21513 (2000).

Bernardo et al., "Purification and Characterization of Magnesium-dependent Neutral Sphingomyelinase from Bovine Brain," J. Biol. Chem. 275(11):7641-7647 (2000).

Betto et al., "Sphingosylphosphocholine modulates the ryanodine receptor/calcium-release channel of cardiac sarcoplasmic reticulum memberances," Biochem. J. 322(1):327-333 (1997).

Bielawska et al., "(1S,2R)-D-erhthro-2-(N-My-ristoylamino)-1-phenyl-1-propanol as an Inhibitor of Ceramidase," J. Biol. Chem. 271(21):12646-12654 (1996).

Bielawska et al., "Ceramide Is Involved in Triggering of Cardiomyocyte Apoptosis Induced by Ischemia and Reperfusion," Am. J. Pathol. 151(5):1257-1263 (1997).

Boudker et al., "Detection and Characterization of Ceramide-1-phosphate Phosphatase Activity in Rat Liver Plasma Membrane," J. Biol. Chem. 268(29):22150-22155 (1993).

Brady et al., "The metabolism of sphingomyelin. II. Evidence of an enzymatic deficiency in Niemann-Pick disease," Proc. Natl. Acad. Sci. USA 55(2):366-369 (1966).

Brindley et al., "Analysis of Ceramide 1-phosphate and Sphingosine-1-phosphate Phosphatase Activities," Methods Enzymol. 311:233-244 (1999).

Brownlee, "Intracellular signalling: sphingosine-1-phosphate branches out," Current Biol. 11(13):R535-R538 (2001).

Burton et al., "Human antibodies from combinatorial libraries," Adv. Immunol. 57:191-280 (1994).

Byers, "What can randomized control trials tell us about nutrition and cancer prevention?," CA Canc. J. 49(6):353-361 (1999).

Cain et al., "Therapeutic Strategies to Reduce TNF-a Mediated Cardiac Contractile Depression Following Ischemia and Reperfusion," *J. Mol. Cell. Cardiol.* 31(5):931-947 (1999).

Caligan et al., "A High-Performance Liquid Chromatographic Method to Measure Sphingosine 1-Phosphate and Related Compounds from Sphingosine Kinase Assays and Other Biological Samples," *Anal. Biochem.* 281(1):36-44 (2000).

Chan et al., "Ceramide Path in Human Lung Cell Death," *Am. J. Respir. Cell Mol. Biol.* 22(4):460-468 (2000).

Chan et al., "Purification and Characterization of Neutral Sphingomyelinase from *Helicobacter pylori*," *Biochemistry* 39(16):4838-4845 (2000).

Chatterjee, "Sphingolipids in Atherosclerosis and Vascular Biology," *Arterioscler. Throm. Vasc. Biol.* 18(10):1523-1533 (1998).

Chatterjee, "Neutral Sphingomyelinase," *Adv. Lip. Res.* 26:25-48 (1993).

Chatterjee, "Neutral Sphingomyelinase: past, present, and future," *Chem. Phys. Lipids* 102(1):79-96 (1999).

Chatterjee et al., "Molecular Cloning, Characterization, and Expression of a Novel Human Neutral Sphingomyelinase," *J. Biol. Chem.* 274(52):37407-37412 (1999).

Chau et al., "Synthesis of Simple Aryl Neutral Sphingomyelinase Inhibitors," *Am. Chem. Soc.* (2001) (Abstract Only).

Chun, "Lysophospholipid receptors: implications for neural signaling," *Crit. Rev. Neuro.* 13(2):151-168 (1999).

Chun et al., "A Growing Family of Receptor Genes for Lysophosphatidic Acid (LPA) and other Lysophospholipids (LPs)," *Cell Biochem. Biophys.* 30(2):213-242 (1999).

Cordis et al., "HPTLC analysis of sphingomylein, ceramide and sphingosine in ischemic/reperfused rat heart," *J. Pharm. Biomed. Anal.* 16(7):1189-1193 (1998).

Cuvlilier et al., "Suppression of ceramide-mediated programmed cell death by sphingosine-1-phosphate," *Nature* 381(6585):800-803 (1996).

Dickson et al., "Serine Palmitoyltransferase," *Methods Enzymol.* 311:3-9 (1999).

Edsall et al., "N, N-Dimethylsphingosine is a potent competitive inhibitor of sphingosine kinase but not of protein kinase C: modulation of cellular levels of sphingosine 1-phosphate and ceramide," *Biochem.* 37(37):12892-12898 (1998).

Edson et al., "The Amihoglycosides," *Mayo Clin. Proc.* 74(5):519-528 (1999).

Eichler et al., "Peptide, peptidomimetic, and organic synthetic combinatorial libraries," *Med. Res. Rev.* 15(6):481-496 (1995).

Fensome et al., "A Neutral Magnesium-dependent Sphingomyelinase Isoform Associated with Intracellular Membranes and Reversibly Inhibited by Reactive Oxygen Species," *J. Biol. Chem.* 275(2):1128-1136 (2000).

Fujii et al., "Mg2+ binding and catalytic function of sphingomyelinase from *Bacillus cereus*," *J. Biochem* (Tokyo) 124(6):1178-1187 (1998).

Fukushima et al., "A single receptor encoded by $vzg-1/lp_{A1}/edg-2$ couples to G proteins and mediates multiple cellular responses to lysophosphatidic acid," *Proc. Natl. Acad. Sci. USA* 95(11):6151-6156 (1998).

Furneisen et al., "Enzymological properties of the LPP1-encoded lipid phosphatase from *Saccharomyces cerevisiae*" *Biochim. Biophys. Acta* 1484(1):71-82 (2000).

Garcia-Ruiz, "Human placenta sphingomyelinase, an exogenous acidic pH-optimum sphingomyelinase, induces oxidative stress, glutathione depletion, and apoptosis in rat hepatocytes," *Hepatology* 32(1):56-65 (2000).

Gates et al., "Serum amyloid p component: its role in platelet activation stimulated by sphingomyelinase d purified from the venom of the brown recluse spider (*Loxosceles reclusa*)," *Toxicon.* 28(11):1303-1315 (1990).

Gatt et al., "Niemann Pick disease: presence of the magnesium-dependent sphingomyelinase in brain of the infantile form of the disease," *J. Neurochem.* 31(2):547-550 (1978).

Gavrilenko et al., "Nucleotide sequence of phospholipase C and sphingomyelinase genes from *Bacillus cereus* BKM-B164," *Bioorg. Khim.* 19(1):133-138 (1993).

Geeraert et al., "Conversion of dihydroceramide into ceramide: involvement of a desaturase," *Biochem. J.* 327(125):125-132 (1997).

Ghosh et al., "Effects of gentamicin on sphingomyelinase activity in cultured human renal proximal tubular cells," *J. Biol. Chem.* 262(26):12550-12556 (1987).

Ghosh et al., "Identification, partial purification, and localization of a neutral sphingomyelinase in rabbit skeletal muscle: Neutral sphingomyelinase in skeletal muscle," *Mol. Cell. Biochem.* 189(1-2):161-168 (1998).

Gilmore et al., "A *Bacillus cereus* cytolytic determinant, cereolysin AB, which comprises the phospholipase C and sphingomyelinase genes: a nucleotide sequence and genetic linkage," *J. Bacterial.* 171(2):744-753 (1989).

Glickman et al., "Molecular Cloning, Tissue-Specific Expression, and Chromosomal Localization of a Novel Nerve Growth Factor-Regulated G-Protein-Coupled Receptor, nrg-1," *Mol. Cel. Neurosci.* 14(2):141-152 (1999).

Goetzl et al., "Diversity of cellular receptors and functions for the lysophospholipid growth factors lysophosphatidic acid and sphingosine 1-phosphate," *Faseb J.* 12(15):1589-1598 (1998).

Goetzl et al., "Eicosanoids and Other Bioactive Lipids in Cancer, Inflammation, and Radiation Injury, 4. 38: A Subfamily of G Protein-Coupled Cellular Receptors for Lysophospholipids and Lysosphingolipids, Introduction: The Biochemistry and Biology of Lipid Phosphoric Acids," *Adv. Exp. Med. Biol.* 469:259-264 (1999).

Gonda, et al., "The novel sphingosine 1-phosphate receptor AGR16 is coupled via pertussis toxin-sensitive and -insensitive G-proteins to multiple signalling pathways," *Biochem. J.* 337(Part 1):67-75 (1999).

Gonzalez-Zorn et al., "The smcL gene of *Listeria ivanovii* encodes a sphingomyelinase C that mediates bacterial escape from the phagocytic vacuole," *Mol. Microbial.* 33(3):510-523 (1999).

Graler et al., "EDG6, a Novel G-Protein-Coupled Receptor Related to Receptors for Bioactive Lysophospholipids, Is Specifically Expressed in Lymphoid Tissue," *Genomics* 53(2):164-169 (1998).

Granziero et al., "Adoptive immunotherapy prevents prostate cancer in a transgenic animal model," *Eur. J. Immunol.* 29(4):1127-1138 (1999).

Gunther, "Myocardial contractility after infarction and carnitine palmitoyltransferase I inhibition in rats," *Eur. J. Pharma.* 406(1):123-126 (2000).

Hakogi et al., "Stereocontrolled synthesis of a sphingomyelin methylene analogue as a sphingomyelinase inhibitor," *Org. Lett.* 2(17):2627-2629 (2000).

Hanada et al., "Specificity of Inhibitors of Seine Palmitoyltransferase (SPT), a Key Enzyme in Sphingolipid Biosynthesis in Intact Cells: A novel evaluation system using an SPT-defective mammalian cell mutant," *Biochem. Pharmacol.* 59(10):1211-1216 (2000).

Hannun et al., "Functions of Sphingolipids and Sphingolipid Breakdown Products in Cellular Regulation," *Science* 243(4890):500-507 (1989).

Hannun et al.., "The Sphingomyelin Cycle: A Prototypic Sphingolipid Signaling Pathway," *Adv. Lipid Res.* 25:27-41 (1993).

Hannun, "Functions of Ceramide in Coordinating Cellular Responses to Stress," *Science* 274(5294):1855-1859 (1996).

Hannun at al, "Ceramide in the eukaryotic stress response," *Trends Cell Biol.* 10(2):73-80 (2000).

He et al., "A Fluorescence-Based High-Performance Liquid Chromatography Assay to Determine Acid Ceramidase Activity," *Anal. Biochem.* 274(2):264-269 (1999).

Heringdorf et al., "Stimulation of intracellular sphingosine-1-phosphate production by G-protein-coupled sphingosine-1-phosphate receptors," *Eur. J. Pharmacol.* 414(2-3):145-154 (2001).

Hernandez et al., "Rapid Activation of Neutral Sphingomyelinase by Hypoxia-Reoxygenation of Cardiac Myocytes," *Circ. Res.* 86(2):198-204 (2000).

Hetland et al., "Phospholipase C from *Bacillus cereus* has sphingomyelinase activity," *Scand. J. Clin. Lab. Invest.* 42(1):57-61 (1982).

Higuchi et al., "Acidic sphingomyelinase-generated ceramide is needed but not sufficient for TNF-induced apoptosis and nuclear factor-kappa B activation," *J. Immunol.* 157(1):297-304 (1996).

Hinkovska-Glacheva et al., "Activation of a Plasma Membrane-Associated Neutral Sphingomyelinase and Concomitant Ceramide Accumulation During IgG-Dependent Phagocytosis in Human Polymorphonuclear Leukocytes," *Blood* 91(12):4761-4769 (1998).

Hise et al., "Fatty Acyl Chain Composition in the Determination of Renal Membrane Order," *J. Clin. Invest.* 77(3):768-773 (1986).

Hla et al., "An Abundant Transcript Induced in Differentiating Human Endothelial Cells Encodes a Polypeptide with Structural Similarities to G-Protein-coupled Receptors," *J. Biol. Chem.* 265(16):9308-9313 (1990).

Hofmann et al., "Cloning and characterization of the mammalian brain-specific, $Mg^{2+}$-dependent neutral sphingomyelinase," *Proc. Natl. Acad. Sci. USA* 97(11):5895-5900 (2000).

Hofstadler et al., "Multiplexed Screening of Neutral Mass-Tagged RNA Targets against Ligand Libraries with Electrospray Ionization FTICR MS: a Paradigm for High-Throughput Affinity Screening," *Anal. Chem.* 71(16):3436-3440 (1999).

Holopainen et al., "Sphingomyelinase Activity. Associated with Human Plasma Low Density Lipoprotein," *J Biol. Chem.* 275(22):16484-16489 (2000).

Horn et al., "Sphingofungins E and F: Novel Serinepalmitoyl Trans-Ferase Inhibitors From *Paecilomyces variotii*," *J. Antibiot.* (Tokyo) 45(10):1692-1696 (1992).

Hoye et al., "Synthesis (and Alternative Proof of Configuration) of the Scyphostatin C(1')-C(20') Trienoyl Fragment," *Organic Letts.* 2(10):1481-1483 (2000).

Hudson, "Recombinant antibody fragments," *Curr. Op. Biotechnol.* 9(4):395-402 (1999).

Humpf et al., "Acylation of naturally occurring and synthetic 1-deoxysphinganines by ceramide synthase. Formation of N-palmitoyl-aminopentol produces a toxic metabolite of hydrolyzed fumonisin, AP1, and a new category of ceramide synthase inhibitor," *J. Biol. Chem.* 273(30):19060-19064 (1998).

Huwiler et al., "Physiology and pathophysiology of sphingolipid metabolism and signling," *Biochim. Biophys. Acta* 1485(2-3):63-99 (2000).

Igarashi, "Functional Roles of Sphingosine, Sphingosine 1-Phosphate, and Methylsphingosines: In Regard to Membrane Sphingolipid Signaling Pathways," J. Biochem. 122(6):1080-1087 (1997).

Igarashi, "Sphinosine-l-Phosphate as an Intercellular Signaling Molecule," F. Huchinson Cancer Research Center, University of Washington, Seattle, (1998).

Ikezawa et al., "Studies on Sphingomyelinase of *Bacillus cereus*. 1. Purification and Properties," *Biochim. Biophys. Acta* 528(2):247-256 (1978).

Im et al., "Characterization of a novel sphingosine 1-phosphate receptor, Edg-8," *J. Biol. Chem.* 275(19):14281-14286 (2000).

Im et al., "Molecular Cloning and Characterization of a Lysophosphatidic Acid Receptor, Edg-7, Expressed in Prostate," *Mol. Pharmacol.* 57(4):753-759 (2000).

Izuhara et al., "Studies toward the Total Synthesis of Scyphostatin: First Entry to the Highly Functionalized Cyclohexenone Segment," *Organic Lett.* 3(11):1653-1656 (2001).

Jimbo et al., "Development of a New Inhibitor of Glucosylceramide Synthase," *J. Biochem.* 127(3):485-491 (2000).

Johansen et al., "*Bacillus cereus* strain SE-1: nucleotide sequence of the sphingomyelinase C gene," *Nucl. Acids Res.* 16(21):10370 (1998).

Jonghe et al., "Structure-Activity Relationship of Short-Chain Sphingoid Bases As Inhibitors of Sphingosine Kinase", *Bioorg. Medicinal Chem. Lett.* 9(21):3175-3180 (1999).

Kajstura et al., "Apoptotic and Necrotic Myocyte Cell Deaths Are Independent Contributing Variables of Infarct Size in Rats," *Lab. Invest.* 74(1):86-107 (1996).

Kanfer et al., "The Metabolism of Sphingomyelin. I. Purification and properties of a sphingomyelin-cleaving enzyme from rat liver tissue," *J. Biol. Chem.* 241(5):1081-1084 (1966).

Katircioglu et al., "Myocardial preservation in acute coronary artery occlusion with coronary sinus retroperfusion and carnitine," *J. Cardiovasc. Surg.* (Torino) 41(1):45-50 (1999.

Kay et al., "Identification of enzyme inhibitors from phage-displayed combinatorial peptide libraries," *Comb. Chem. High Throughput Screen* 4(7):535-543 (2001).

Kester, "Sphingolipid Metabolites and the Cellular Phenotype," *Trends Glycosci. Glycotechnol.* 9(50):447-460 (1997).

Kihara et al., "Direct Measurement of Changes in Intercellular Calcium Transients During Hypoxia, Ischemia, and Reperfusion of the Intact Mammalian Heart," *Circ. Res.* 65(4):1029-1044 (1989).

Kimura et al., "Two Novel Xenopus Homologs of Mammalian $LP_{A1}$/EDG-2 Function as Lysophosphatidic Acid Receptors in Xenopus Oocytes and Mammalian Cells," *J. Biol. Chem.* 276(18):15208-15215 (2001).

Kita et al., "Reverse hydrolysis reaction of a recombinant alkaline ceramidase of *Pseudomonas aeruginosa*," *Biochim. Biophys. Acta* 1485(2-3):111-120 (2000).

Kohama et al., "Molecular cloning and functional characterization of murine sphingosine kinase," *J. Biol. Chem.* 273(37):23722-23728 (1998).

Kolesnick et al., "Characterization of a Ceramide Kinase Activity from Human Leukemia (HL-60) Cells: Separation From Diacylglycerol Kinase Activity," *J. Biol. Chem.* 265(31):18803-18808 (1990).

Kolesnick, "The thereapeutic potential of modulating the ceramide/sphingomyelin pathway," *J. Clin. Inv.* 110(1):3-8 (2002).

Krown et al., "Tumor necrosis factor alpha-induced apoptosis in cardiac myocytes. Involvement of the sphingolipid signaling cascade in cardiac cell death," *J. Clin. Invest.* 98(12):2854-2865 (1996).

Kubota et al., "Accumulation of ceramide in ischemic human brain of an acute case of cerebral occlusion," *Japan J. Exp. Med.* 59(2):59-64 (1989).

Kubota et al., "Sphingomyelin changes in rat cerebral cortex during focal ischemia," *Neurol. Res.* 18(4):337-341 (1996).

Lanterman et al., "Characterization of sphingosine kinase (SK) activity in *Saccharomyces cerevisiae* and isolation of SK-deficient mutants," *Biochem. J.* 332(Part 2):525-531 (1998).

Lee et al., "Effect of Ischemia on Calcium-Dependent Fluorescence Transients in Rabbit Hearts Containing Indo 1. Correlation with Monophasic Action Potentials and Contraction," *Circ.* 78(4):1047-1059 (1988).

Lee et al., "Cell-cycle-dependent changes in ceramide levels preceding retinoblastoma protein dephosphorylation in G2/M," *Biochem. J.* 334(Part 2):457-461 (1998).

Lee et al., "Improved Inhibitors of Glucosylceramide Synthase," *J. Bio. Chem.* 274(21):14662-14669 (1999).

Lee et al., "Lysophosphatidic acid and sphingosine 1-phosphate stimulate endothelial cell wound healing," *Am. J. Physiol. Cell Physiol.* 278(3):C612-C618 (2000).

Levade, et al., "Sphingomyelinases and Niemann-Pick disease," *J. Clin. Chem. Clin. Biochem.* 24(4):205-220 (1986).

Li et al., "The Human Acid Ceramidase Genes (ASAH): Structure, Chromosomal Location, Mutation Analysis, and Expression," *Genomics* 62(2):223-231 (1999).

Liliom at al, "Sphingosylphosphocholine is a naturally occurring lipid mediator in blood plasma: a possible role in regulating cardiac function via sphingolipid receptors," *Biochem. J.* 355(Part 1):189-197 (2001).

Lin et al., "Identification of neutral and acidic sphingomyelinases in *Helicobacter pylori*," *FEBS Lett.* 423(2):249-253 (1998).

Linn et al., "Regulation of de novo sphingolipid biosynthesis and the toxic consequences of its disruption," *Biochem. Soc.* 29(Part 6):831-835 (2001).

Lister et al., "Interaction of sphingomyelinase with sphingomyelin analogs modified at the G1 and C-3 positions of the sphingosine backbone," *Biochim. Biophys. Acta* 1256(1):25-30 (1995).

Little at al, "Surface display of antibodies," *Biotechn. Adv.* 12(3):539-555 (1994).

Liu et al., "Inhibition of the neutral magnesium-dependent sphingomyelinase by glutathione," *J. Biol. Chem.* 272(26):16281-16287 (1997).

Liu et al., "Purification and Characterization of a Membrane Bound Neutral pH Optimum Magnesium-dependent and Phosphatidylserine-stimulated Sphingomyelinase from Rat Brain," *J. Biol. Chem.* 273(51):34472-34479 (1998).

Liu et al., "Glutathione regulation of neutral sphingomyelinase in tumor necrosis factor-alpha-induced cell death," *J. Biol. Chem.* 273(18):11313-11320 (1998).

Liu at al, "Advances in the signal transduction of ceramide and related sphingolipids," *Crit. Rev. Clin. Lab. Sci.* 36(6):511-573 (1999).

Liu et al., "Molecular Cloning and Functional Characterization of a Novel Mammalian Sphingosine Kinase Type 2 Isoform," *J. Biol. Chem.* 275(26):19513-19520 (2000).

Liu et al., "Sphingomyelinase Assay Using Radiolabeled Substrate," *Meth. Enzymol.* 311:164-167 (2000).

Lochhead at al, "Fluorinated anesthetic exposure "activates" the renal cortical sphingomyelinase cascade," *Kidney Int.* 54(2):373-381 (1998).

Luberto et al., "Sphingomyelin synthase, a potential regulator of intracellular levels of ceramide and diacylglycerol during SV40 transformation. Does sphingomyelin synthase account for the putative phosphatidylcholine-specific phopholipase C?," *J. Biol. Chem.* 273(23):14550-14559 (1998).

Luberto at al, "Sphingolipid Metabolism in the Regulation of Bioactive Molecules," *Lipids* 34(Supp. 1):S5-S11 (1999).

Lynch at al, "Life on the edg," *Trends Pharmacol. Sci.* 20(12):473-475 (1999).

Magnelli et al., "BCL-2 Overexpression Abolishes Early Calcium Waving Preceding Apoptosis in NIH-3T3 Murine," *Biochem. Biophys. Res. Comm.* 204(1):84-90 (1994).

Mandala et al., "Inhibition of Serine Palmitoyl-Transferase Activity by Lipdxamycin," *J. Antibiot.* (Tokyo) 47(3):376-379 (1994).

Mandala et al., "The Discovery of Australifungin, a novel Inhibitor of Sphinganine N-Acyltransferase from *Sporormiella australis*. Producing Organism, Fermentation, Isolation, and Biological Activity," *J. Antibiot.* (Tokyo) 48(5):349-356 (1995).

Mandala et al., "Khafrefungin, a novel inhibitor of sphingolipid synthesis," *J. Biol. Chem.* 272(51):32709-32714 (1997).

Mandala et al., "Viridiofungins, Novel Inhibitors of Sphingolipid Synthesis," *J. Antibiot.* (Tokyo) 50(4):339-343 (1997).

Mandala et al., "Sphingoid base 1-phosphate phosphatase: a key regulator of sphingolipid metabolism and stress response," *Proc. Natl. Acad. Sci. USA* 95(1):150-155 (1998).

Mandala et al., "Isolation and Characterization of Novel Inhibitors of Sphingolipid Synthesis: Australifungin, Viridiofungins, Rustmicin, and Khafrefungin," *Methods Enzymol.* 311:335-348 (1999).

Mandala et al., "Molecular cloning and characterization of a lipid phosphohydrolase that degrades sphingosine-1-phosphate and induces cell death," *Proc. Natl. Acad. Sci. USA* 97(14):7859-7864 (2000).

Mandala et al., "Sphingosine-1-Phosphate Phosphatases," *Prostaglandins & Other Lipid Mediators* 64(1-4):143-156 (2001).

Mao et al., "Molecular cloning and characterization of SCaMPER, a Sphingolipid Ca2+ release-mediating protein from endoplasmic reticulum," *Proc. Natl. Acad. Sci. USA* 93(5):1993-1996.

Mao et al., "Cloning of an Alkaline Ceramidase from *Saccharomyces cerevisiae*: An Enzyme with Reverse (CoA-Independent) Ceramide Synthase Activity," *J. Biol. Chem.* 275(10):6876-6884 (2000).

Mao et al., "Cloning and Characterization of a *Saccharomyces cerevisiae* Alkaliine Ceramidase with Specificity for Dihydroceramide," *J. Biol. Chem.* 275(40):31369-31378 (2000).

Mao et al., "Cloning and Characterization of a Novel Human Alkaline Ceramidase: A Mammalian Enzyme That Hydrolyzes Phytoceramide," *J. Biol. Chem.* 276(28):26577-26588 (2001).

Marks et al., "Methods for Studying Glucosylceramide Synthase," *Methods Enzymol.* 311:50-59 (1999).

Martin et al., "Neutral Magnesium-Dependent Sphingomyelinase from Liver Plasma Membrane: Purification and Inhibition by Ubiquinol," *J. Bioenerg. Biomember.* 33(2):143-153 (2001).

Meacci et al., "Receptor-mediated activation of phospholipase D by sphingosine 1-phosphate in skeletal muscle C2C12 cells: A role for protein kinase C," *FEBS Lett.* 457(2):184-188 (1999).

Meldrum, "Tumor necrosis factor in the heart," *Am. J. Physiol.* 274(3):R577-R595 (1998).

Melendez et al., "Human sphingosine kinase: molecular cloning, functional characterization and tissue distribution," *Gene* 251(1):19-26 (2000).

Meroni et al., "Effect of N-Acetylsphingosine (C2) and the Ceramidase Inhibitor (1S,2R)-D-erythro-2-(n-myristoylamino)-1 phenyl-1-propanol on the Regulation of Sertoli Cell Function," *J. Androl.* 20(5):619-625 (1999).

Merrill et al., "Activities of serine palmitoyltransferase (3-ketosphinganine synthase) in microsomes from different rat tissues," *J. Lipid Res.* 26(5):617-622 (1993).

Michel et al., "Characterization of Ceramide Synthesis. A Dihydroceramide Desaturase Introduces the 4,5-*Trans*-Double Bond of Sphingosine At the Level of Dihydroceramide," *J. Biol. Chem.* 272(36):22432-22437 (1997).

Milstien et al., "Targeting sphingosine-1-phosphate: A novel avenue for cancer therapeutics," *Cancer Cell.* 9(3):148-150 (2006) (Abstract Only).

Mingeot-Leclercq et al., "Aminoglycosides: activity and resistance," *Antimicrob. Agents Chemother.* 43(4):727-737 (1999).

Mingeot-Leclercq et al., "Aminoglycosides: nephrotoxicity," *Antimicrob. Agents Chemother.* 43(5):1003-1012 (1999).

Mitsutake et al., "Purification, Characterization, Molecular Cloning, and Subcellular Distribution of Neutral Ceramidase of Rat Kidney," *J. Biol. Chem.* 276(28):26249-26259 (2001).

Miyake, "Serine palmitoyltransferase is the primary target of a sphingosine-like immunosuppressant, ISP-1/myriocin," *Biochem. Biophys. Res. Commun.* 211(2):396-403 (1995).

Mohan et al., "Evidence that Neutral Sphingomyelinase of Cultured Murine Neuroblastoma Cells is Oriented Externally on the Plasma Membrane," *Biochem. Biophys. Acta* 777(2):339-342 (1984).

Mohler et al., "Soluble Tumor Necrosis Factor (TNF) Receptors Are Effective Therapeutic Agents in Lethal Endotoxemia and Function Simultaneously as Both TNF Carries and TNF Antagonists," *J. Immunol.* 151(3):1548-1561 (1993).

Nakajima et al., "Expression and characterization of Edg-1 receptors in rat cardiomyocytes: Calcium deregulation in response to sphingosine 1-phosphate," *Eur. J. Biochem.* 267(18):5679-5686 (2000).

Nakajima et al., *Biophysical J.* 78:319 A (2000).

Napoli et al., "Ischaemic preconditioning of rat myocardium: effects on postischaemic coronary endothelium hypermaebility and microcirculatory damage," *J. Clin. Bas. Cardiol.* 1(1):37-42 (1998).

Nikolova-Karakashian et al., "Ceramidases," *Meth. Enzymol.* 311:194-201 (1999).

Ohta et al., "A possible role of sphingosine in induction of apoptosis by tumor necrosis factor-a in human neutrophils," *FEBS Lett.* 355(3):267-270 (1994).

Ohta et al., "Induction of apoptosis by sphingosine in human leukemic HL-60 cells: a possible endogenous modulator of apoptotic DNA fragmentation occurring during phorbol ester-induced differentiation," *Cancer Res.* 55(3):691-697 (1995).

Okamoto et al., "EDG1 Is a Functional Sphingosine-1-phosphate Receptor That Is Linked via a $G_{i/o}$ to Multiple Signaling Pathways, Including Phospholipase C Activation, $Ca^{2+}$ Mobilization, Ras-Mitogen-activated Protein Kinase Activation, and Adenylate Cyclase Inhibition," *J. Biol. Chem.* 273(42):27104-27110 (1998).

Okamoto et al., "EDG3 Is a Functional Receptor Specific for Sphingosine 1-Phosphate andSphingosylphosphorylcholine with Signaling Characteristics Distinct from EDG1 and AGR16," *Biochem. Biophys. Res. Commun.* 260(1):203-208 (1999).

Okazaki et al., "Characteristics and partial purification of a novel cytosolic, magnesium-independent, neutral sphingomyelinase activated in the early signal transduction of 1 alpha,25-dihydroxyvitamin D3-induced HL-60 cell differentiation," *J. Biol. Chem.* 269(6):4070-4077 (1994).

Okino et al., "Molecular Cloning, Sequencing, and Expression of the Gene Encoding Alkaline Ceramidase from *Pseudomonas aeruginosa*: Cloning of a Ceramidase Homologue from mycobacterium Tuberculosis," *J. Biol. Chem.* 274(51):36616-36622 (1999).

Olivera et al., "Sphingosine-1-phosphate as second messenger in cell proliferation induced by PDGF and FCS mitogens," *Nature* 365(6446):557-560 (1993).

Olivera et al., "Assaying Sphingosine Kinase Activity," *Methods Enzymol.* 311:215-223 (1999).

Olshefski et al., "Glucosylceramide Synthase Inhibition Enhances Vincristine-Induced Cytotoxicity," *Int. J. Cancer* 93(1):131-138 (2001).

Oral et al., "Sphingosine mediates the immediate negative inotropic effects of tumor necrosis factor-alpha in the adult mammalian cardiac myocyte," *J. Biol. Chem.* 272(8):4836-4842 (1997).

Parrill et al., "Identification of Edg1 Receptor Residues That Recognize Sphingosine 1-Phosphate," *J. Biol. Chem.* 275(50):39379-39384 (2000).

Pitson et al., "Human sphingosine kinase: purification, molecular cloning and characterization of the native and recombinant enzymes," *Biochem J.* 350(Part 2):429-441 (2000).

Pitson et al., "Expression of a catalytically inactive sphingosine kinase mutant blocks agonist-induced sphingosine kinase activation. A dominant-negative sphingosine kinase," *J. Biol. Chem.* 275(43):33945-33950 (2000).

Presta et al., "Humanization of an Anti-Vascular Endothelial Growth Factor Monoclonal Antibody for the Therapy of Solid Tumors and Other Disorders," *Canc. Res.* 57(20):4593-4599 (1997).

Raag et al., "Single-chain Fvs," *FASEB J.* 9(1):73-80 (1995).

Rani et al., "Cell-Cycle Arrest Induced by an Inhibitor of Glucosylceramide Synthase," *J. Biol. Chem.* 270(6):2859-2867 (1995).

Riley et al., "Alteration of tissue and serum sphinganine to sphingosine ratio: an early biomarker of exposure to fumonisin-containing feeds in pigs," *Toxicol. Appl. Pharmacol.* 118(1):105-112 (1993).

Riley et al., "Fermentation, partial purification, and use of serine palmitoyltransferase inhibitors from *Isaria* (=*Cordyceps*) *sinclairii*," *Meth. Enzymol.* 311:348-361 (1999).

Romiti et al., "Characterization of sphingomyelinase activity released by thombin-stimulated platelets," *Mol. Cell. Biochem.* 205(1-2):75-81 (2000).

Runcie at al, "A Short and Efficient Route to Novel Scyphostatin Analogues," *Organic Lett.* 3(21):3237-3239 (2001).

Sabbadini et al., "Sphingosine is endogenous to cardiac and skeletal muscle," *Biochem. Biophys. Res. Comm.* 193(2):752-758 (1993).

Sabbadini et al., "The Mirf trial: predicting the incidence and severity of CAD using serum sphingolipids," *Circ.* 102(18):II699 (2000).

Saint-Joanis et al., "Gene cloning shows the alpha-toxin of *Clostridium perfringens* to contain both sphingomyelinase and lecithinase activities," *Mol. Gen. Genet.* 219(3):453-60 (1989).

Saito et al.; "Absolute Configuration of Scyphostatin," *Organic Letts* 2(4):505-506 (2000).

Sakai et al., "A devise for recording left ventricular contraction and electrocardiogram in nonworking isolated perfused rat heart," *Jpn J. Pharmacol.* 28(2):223-229 (1978).

Sawada et al., "Ordering of ceramide formation, caspase activation, and Bax/Bcl-2 expression during etoposide-induced apoptosis in C6 glioma cells," *Cell Death Differentiation* 7(9):761-7672 (2000).

Sato, "A new role of lipid receptors in vascular and cardiac morphogenesis," *J. Clin. Invest.* 106(8):939-940 (2000).

Sawai et al., "Function of the Cloned Putative Neutral Sphingomyelinase as Lyso-platelet Activating FactorPhospholipase C," *J. Biol. Chem.* 274(53):38131-38139 (1999).

Sawai et al., "Identification of ISC1 (YER019w) as Inositol Phosphosphingolipid Phospholipase C *Saccharomyces cerevisiae*," *J. Biol. Chem.* 275(50):39793-39798 (2000).

Schissel et al., "$Zn^{2+}$-stimulated Sphingomyelinase Is Secreted by Many Cell Types and Is a Product of the Acid Sphingomyelinase Gene," *J. Biol. Chem.* 271(31):18431-18436 (1996).

Sergeyev et al., "Lipid Spectrum of the Myocardium of White Rats Exposed to Hypoxic Hypoxia," *Kosm. Biol. Aviakosm. Med.* (Russian) 15(6):71-74 (1981).

Shayman et al., "Glucosylceramide Synthase: Assay and Properties," *Methods Enzymol.* 311:42-49 (1999).

Shayman et al., "Inhibitors of Glucosylceramide Synthase," *Methods Enzymol.* 311:373-387 (1999).

Shinghal et al., "Ceramide 1-Phosphate Phosphatase Activity in Brain," *J. Neurochem.* 61(6):2279-2285 (1993).

Siehler et al., "Sphingosine 1-Phosphate Activates Nuclear Factor-kappa B through Edg Receptors: Activation Through Edg-3 and Edg-5, but not Edg-1, in Human Embryonic Kidney 293 Cells," *J. Biol. Chem.* 276(52):48733-48739 (2001).

Siess et al., "Lysophosphatidic Acid and Sphingosine 1-Phosphate: Two Lipid Villains Provoking Cardiovascular Diseases?" *IUBMB Life* 49(3):161-171 (2000).

Smith et al., "Hypoxia, calcium fluxes, and inotropic state: Studies in cultured heart cells," *Am. Heart J.* 103(4 Part 2):716-723 (1982).

Smith et al., "Purified Fumonisin $B_1$ Decreases Cardiovascular Function but does not Alter Pulmonary Capillary Permeability in Swine," *Toxicol. Sci.* 56(1):240-249 (2000).

Spence, "Sphingomyelinases," *Adv. Lipid Res.* 26:3-23 (1993).

Spence et al., "A new Zn2+-stimulated sphingomyelinase in fetal bovine serum," *J. Biol. Chem.* 264(10):5358-5363 (1989).

Spiegel et al., "Sphingolipid metabolism and cell growth regulation," *FASEB J.* 10(12):1388-1397 (1996).

Spiegel et al., "Review: Roles of Sphingosine-1-phosphate in Cell Growth, Differentiation, and Death," *Biochemistry* (Mosc). 63(1):69-83 (1998).

Spiegel et al., "Functions of a new family of sphingosine-1-phosphate receptors," *Biochim. Biophys. Acta* 1484(2-3):107-116 (2000).

Sucheck et al., "Combinatorial synthesis of aminoglycoside libraries," *Curr. Opin. Drug Disc. Develop.* 4(4):462-470 (2001).

Sugita at al, "Ceramidase and ceramide synthesis in human kidney and cerebellum. Description of a new alkaline ceramidase," *Biochim. Biophys. Acta* 398(1):125-131 (1975).

Sugiyama et al., "Sphingosine 1-phosphate induces sinus tachycardia and coronary vasoconstriction in the canine heart," *Cardiovasc. Res.* 46(1):119-125 (2000).

Sumnicht et al., "Lipid Composition of Transverse Tubular Membranes from Normal and Dystrophic Skeletal Muscle," *Arch. Biochem. Biophys.* 215(2):628-637 (1982).

Szulc et al., "A facile regioselective synthesis of sphingosine 1-phosphate and ceramide 1-phosphate," *Tetrahedron Lett.* 41(41):7821-7824 (2000).

Tamura et al., "Mass Production of Sphingomyelinase of *Bacillus cereus* by a Protein-Hyperproducing Strain, *Bacillus brevis* 47, and Its Purification," *J. Biochem.* (Tokyo) 112(4):488-491 (1992).

Tanaka et al., "Structural Elucidation of Scyphostatin, an Inhibitor of Membrane-Bound Neutral Sphingomyelinase," *J. Am. Chem. Soc.* 199(33):7871-7872 (1997).

Tani et al., "Purification and Characterization of a Neutral Ceramidase from Mouse Liver: A single Protein Catalyzes the Reversible Reaction in Which Ceramide is Both Hydrolyzed and Synthesized," *J. Biol. Chem.* 275(5):3462-3468 (2000).

Tazabekova et al., "Synthesis of sphingomyelin phosphonate analogues and preparation of an affinity sorbent for the sphingomyelinase purification," *Bioorg. Khim.* 13(5):648-653 (1987).

Tomita et al.., "Secondary structure of sphingomyelinase from *Bacillus cereus*," *J. Biochem.* (Tokyo) 108(5):811-815 (1990).

Tomiuk et al., "Cloned mammalian neutral sphingomyelinase: Functions in sphingolipid signaling?," *Proc. Natl. Acad. Sci. USA* 95(7):3638-3643, (1998).

Torley et al., "A turbidometric assay for phospholipase C and sphingomyelinase," *Anal. Biochem.* 222(2):461-464 (1994).

Tosaka et al., "Sphingosine 1-phosphate contracts canine basilar arteries in vitro and in vivo: possible role in pathogenesis of cerebral vasospasm," *Stroke* 32(12):2913-2919 (2001).

Triola et al., "Synthesis of a Cyclopropene Analogue of Ceramide, a Potent Inhibitor of Dihydroceramide Desaturase," *Angew. Chem. Int. Ed.* 40(10):1960-1962 (2001).

Tsunoda et al., "Early Fumonisin B1 Toxicity in Relation to Disrupted Sphingolipid Metabolism in Male BALB/c Mice," *J. Biochem. Mol. Toxicol.* 12(5):281-289 (1998).

Uchida et al., "Alutenusin, a Specific Neutral Sphingomyelinase Inhibitor, Produced by Penicillium sp. FO-7436," *J. Antibiot.* (Tokyo) 52(6):572-574 (1999).

Urdal, "The Biochemistry of Tumor Associated Gangliotriosylceramide and the Use of This Glycolipid as a Target for Antibody Dependent, Avidin Mediated Drug Killing of Tumor Cells," *Dissertation Abstracts Int.* 41(11B):4062-4063 (1980).

Usta et al., "Structural Requirements of Ceramide and Sphingosine Based Inhibitors of Mitochondria Ceramidase," *Biochemistry* 40(32):9657-9668 (2000).

Van Brocklyn et al., "Sphingosine 1-phosphate-induced cell rounding and neurite retraction are mediated by the G protein-coupled receptor H218," *J. Biol. Chem.* 274(8):4626-4632 (1999).

Van Veldhoven et al., "Sphingosine-Phosphate Lyase," *Adv. Lipid Res.* 26:69-98 (1993).

Van Veldhoven, "Shingosine-1-phosphate Lyase," *Methods Enzymol.* 311:244-254 (1999).

Van Veldhoven et al., "Human sphingosine-1-phosphate lyase: cDNA cloning, functional expression studies and mapping to chromosome 10q22(1)," *Biochim. Biophys. Acta* 1487(2-3):128-134 (2000).

Visentin et al., "Validation of an anti-sphingosine-1-phosphate antibody as a potential therapeutic in reducing growth, invasion, and angiogenesis in multiple tumor lineages," *Cancer Cell.* 9(3):225-238 (2006).

Vivekananda et al., "Sphingomyelin metabolites inhibit sphingomyelin synthase and CTP:phosphocholine cytidylyltransferase," *Am. J. Physiol. Lung Cell. Mol. Physiol.* 228(1):L98-L107 (2001).

Walev et al., "Selective killing of hunian monocytes and cytokine release provoked by sphingomyelinase (beta-toxin) of *Staphylococcus aureus*," *Infect. Immun.* 64(8):2974-2979 (1996).

Wang et al., "A Single Amino Acid Determines Lysophospholipid Specificity of the S1 P1 (EDG1) and LPA1 (EDG2) Phospholipid Growth Factor Receptors," *J. Biol. Chem.* 276(52):49213-49220 (2001).

Wang et al., "Fumonisins and other inhibitors of de novo sphingolipid biosynthesis," *Adv. Lipid Res.* 26:215-234 (1993).

Webster's Dictionary, p. 1135 (1990).

Winter et al., "Making antibodies by phage display technology," *Annu. Rev. Immunol.* 12:433-455 (1994).

Wright et al., "Genetically engineered antibodies: progress and prospects," *Crit. Rev. Immunol.* 12(3-4):125-168 (1992).

Xia et al., "Tumor necrosis factor-alpha induces adhesion molecule expression through the sphingosine kinase pathway," *Proc. Natl. Acad. Sci.* (USA) 95(24):14196-14201 (1988).

Xia et al., "High density lipoproteins (HDL) interrupt the sphingosine kinase signaling pathway. A possible mechanism for protection against atherosclerosis by HDL," *J. Biol. Chem.* 274(46):33143-33147 (1999).

Xu et al., "Involvement of de novo ceramide biosynthesis in tumor necrosis factor-alpha/cycloheximide-induced cerebral endothelial cell death," *J. Biol. Chem.* 273(26):16521-16526 (1998).

Xu et al., "Sphingosylphosphorylcholine is a ligand for ovarian cancer G-protein-coupled receptor 1," *Nat. Cell Biol.* 2(5):261-267 (2000).

Yada et al., "Purification and biochemical characterization of membrane-bound epidermal ceramidases from guinea pig skin," *J. Biol. Chem.* 270(21):12677-12684 (1995).

Yamada et al., "Nucleotide sequence and expression in *Escherichia coli* of the gene coding for sphingomyelinase of *Bacillus cereus*," *Eur. J. Biochem.* 175(2):213-220 (1988).

Yamaji et al., "Lysenin, a novel sphingomyelin-specific binding protein," *J. Biol. Chem.* 273(9):5300-5306 (1998).

Yamanaka et al., "Acid Sphingomyelinase of Human Brain: Purification to Homogeneity," *J. Neurochem.* 38(6):1753-1764 (1982).

Yamazaki et al., "Edg-6 as a Putative Sphingosine 1-Phosphate Receptor Coupling to Ca2+ Signaling Pathway," *Biochem. Biophys. Res. Commun.* 268(2):583-589 (2000).

Yatomi et al., "Sphiongosine-1-Phosphate: A Platelet-Activating Sphingolipid Released from Agonist Stimulated Human Platelets," *Blood* 86(1):193-202 (1995).

Yatomi et al., "Sphingosine 1-phosphate, a bioactive sphingolipid abundantly stored in platelets, is a normal constituent of human plasma and serum," *J. Biochem.* 121(5):969-973 (1997).

Yatomi et al., "Sphingosine 1-phosphate induces platelet activation through an extracellular action and shares a platelet surface receptor with lysophosphatidic acid," *J. Biol. Chem.* 272(8):5291-5297 (1997).

Yellon et al., "Ischaemic preconditioning limits infarct size in the rat heart," *Cardiovasc. Res.* 26(10):983-987 (1992).

Yoshimura et al., "Inhibition of Neutral Sphingomyelinase Activation and Ceramide Formation by Glutathione in Hypoxic PC12 Cell Death," *J. Neurochem.* 73(2):675-683 (1999).

Yu et al., "Picotal role for acidic sphingomyelinase in cerebral ischemia-induced ceramide and cytokine production, and neuronal apoptosis," *J. Mol. Neurosci.* 15(2):85-97 (2000).

Zager et al., "Decreased expression of mitochondrial-derived $H_2O_2$ and hydroxyl radical in cytoresistant proximal tubules," *Kidney Int.* 52(4):942-952 (1997).

Zechner et al., "MKK6 inhibits myocardial cell apoptosis via a p38 MAP kinase-dependent pathway," *J. Biol. Chem.* 273(14):8232-8239 (1998).

Zelinski et al., "Phosphatidylcholine biosynthesis in isolated hamster heart," *J. Biol. Chem.* 255(23):11423-11428 (1980).

Zhang et al., "Comparative analysis of three murine G-protein coupled receptors activated by sphingosine-1-phosphate," *Gene* 227(1):89-99 (1999).

Zhang et al., "Human Acid Ceramidase Gene: Novel Mutations in Farber Disease," *Mol. Genet. Metab.* 70(4):301-309 (2000).

Zhou et al., "Identification of the First Mammalian Sphingosine Phosphate Lyase Gene and its Functional Expression in Yeast," *Biochem. Biophys. Res. Comm.* 242(3):502-507 (1998).

Zweerink et al., "Characterization of a Novel, Potent, and Specific Inhibitor of Serine Palmitoyltransferase," *J. Biol. Chem.* 267(35):25032-25038 (1992).

* cited by examiner

METHODS FOR DECREASING IMMUNE RESPONSE AND TREATING IMMUNE CONDITIONS

RELATED APPLICATIONS

This application claims priority to, the benefit of, and incorporates by reference for all purposes the following patent-related documents, each in its entirety: U.S. provisional patent application Ser. No. 60/810,185, filed 31 May, 2006, U.S. provisional patent application Ser. No. 60/835,569, filed 12 Aug., 2006, and U.S. patent application Ser. No. 11/588,973, filed 27 Oct., 2006, of which this application is a continuation-in-part.

TECHNICAL FIELD

The present invention relates to methods of decreasing an immune response using agents that bind bioactive lipid molecules and thus decrease the effective concentration of these bioactive lipid molecules. These bioactive lipids play a role in human and/or animal disease as signaling molecules. One class of bioactive signaling lipids considered in accordance with the invention is the lysolipids. Examples of signaling lysolipids are sphingosine-1-phosphate (S1P) and the various lysophosphatidic acids (LPAs). Antibodies and other agents that bind signaling lipids, and derivatives and variants thereof, thereby decreasing the effective concentration of these lipids, can be used to decrease an immune response, and in the treatment and/or prevention of diseases and conditions characterized by an excessive, aberrant or undesired immune response, through the delivery of pharmaceutical compositions that contain such antibodies, alone or in combination with other therapeutic agents and/or treatments. Autoimmune disorders, allograft rejection and graft-versus-host disease are examples of diseases and conditions which may be treated according to the methods of the present invention. Disorders characterized by inappropriate or aberrant lymphocyte infiltration are also considered to be diseases characterized by an excessive, aberrant or undesired immune response and therefore may be treated according to the methods of the present invention.

BACKGROUND OF THE INVENTION

I. Introduction

The following description includes information that may be useful in understanding the present invention. It is not an admission that any such information is prior art, or relevant, to the presently claimed inventions, or that any publication specifically or implicitly referenced is prior art or even particularly relevant to the presently claimed invention.

II. Background

The present invention relates to methods of decreasing or attenuating aberrant, excessive or undesired immune responses, including autoimmune responses. These processes, separately or together, are involved in many diseases and conditions. These diseases or conditions may be systemic or may be relatively localized, for example to the red blood cells, blood vessels, connective tissues, nervous system, major organs, endocrine glands such as the thyroid or pancreas, muscles, joints or skin.

A. Diseases and Conditions Characterized by an Aberrant, Excessive or Undesired Immune Response The immune system protects the body from potentially harmful substances such as microorganisms, toxins, cancer cells, and foreign blood or cells from another person or species. These antigens are destroyed by the immune response, which includes production of antibodies and sensitized lymphocytes, which are specialized white blood cells that recognize and destroy particular antigens.

1. Autoimmune Diseases and Conditions

Autoimmune disorders develop when the immune system destroys normal body tissues, which it normally would ignore. Normally, the immune system is capable of differentiating self from non-self tissue. Some lymphocytes become sensitized against self tissue cells, but this response is usually controlled or suppressed by other lymphocytes. Autoimmune disorders occur when the normal control process is disrupted. Normally, most T cells that recognize self-antigens are eliminated in the thymus, their site of origin, and never enter general circulation. The normal T cells circulate through the lymph nodes and the blood without ever responding to self-antigens. However, it is believed that patients with autoimmune disorders bear T cells that can become activated by self-antigens. Once activated, the T cell divides to produce many effector cells which attack the activating antigen. When the antigen is a self-antigen rather than a foreign antigen, serious and potentially deadly consequences result. Autoimmune responses may also occur if normal body tissue is altered so that it is no longer recognized as self.

Autoimmune disorders may result in destruction of one or more types of body tissues, abnormal growth of an organ, or changes in organ function. The disorder may affect only one organ or tissue type or may affect multiple organs and tissues, depending on the identity of the activating antigen. Organs and tissues commonly affected by autoimmune disorders include blood components such as red blood cells, blood vessels, connective tissues, nervous system, major organs, endocrine glands such as the thyroid or pancreas, muscles, joints, and skin. A person may experience multiple autoimmune disorders at the same time.

Some nonlimiting examples of confirmed or suspected autoimmune diseases and conditions include Type 1 diabetes mellitus, psoriasis, autoimmune glomerulonephritis, autoimmune hemolytic anemia, acute disseminated encephalomyelitis, Addison's disease, alopecia universalis, ankylosing spondylitis, antiphospholipid antibody syndrome, autoimmune oophoritis, autoimmune orchitis, autoimmune polyendocrine failure, Behcet disease, Berger's disease, Buergers disease, bullous pemphigus, celiac sprue, Chagas' disease, Graves disease, Goodpastures syndrome, Guillain-Barre syndrome, Hashimato's thyroiditis, chronic active hepatitis, chronic fatigue syndrome, chronic progressive hepatitis, idiopathic thrombocytopenia purpura, Jobs syndrome, psoriatic arthritis, rheumatoid arthritis, Kawasaki's disease, multiple sclerosis, myasthenia gravis, pemphigoid, pemphigus, pemphigus erythematosus, pemphigus foliaceus, pemphigus vulgaris, polymyalgia rheumatica, pulmonary fibrosis, Reiters syndrome, Reidel's thyroiditis, rheumatic fever, sarcoidosis, Sezary syndrome; scleroderma, ulcerative colitis, autoimmune hemolytic anemia, Feltys syndrome, systemic lupus erythematosus, discoid lupus erythematosus, autoimmune polyarteritis nodosa, Caplans syndrome, Crohn's disease, dysautonomia, endometriosis, hydraadenitis suppurativa, interstitial cystitis, Lyme disease, postural orthostatic tachycardia syndrome, opsoclonus myoclonus syndrome, psoriasis, Sjogren's syndrome, CREST syndrome, viral myocarditis, Wegener's granulomatosis and Wiscott-Aldrich syndrome. Some of these disorders have been confirmed to be autoimmune disorders by the presence of autoantibodies.

2. Other Conditions Characterized by an Aberrant, Excessive or Undesired Immune Response Methods of the present invention are also believed to be useful in treating conditions or diseases, other than autoimmune conditions, in which it is desirable to decrease or attenuate the immune response. Such conditions may be characterized by an immune response which is excessive, aberrant or undesired. Non-limiting examples include allograft rejection and graft-versus-host disease. Allografting is transplantation of an organ or tissue (e.g., kidney, heart, lung, cornea, skin, bone marrow, pancreas or other tissues or organs) into a genetically non-identical member of the same species. Thus, most human organ and tissue transplants are allografts (with the majority of the remainder being transplants from an identical twin). Allograft rejection occurs when the transplant recipient's immune system recognizes the allograft as foreign and begins to destroy it. This may eventually destroy the transplanted organ and may result in the need for a second transplant. Thus, while not necessarily unexpected, allograft rejection is an example of an immune response that is undesired.

Graft-versus-host disease (GVHD) is a complication of bone marrow transplantation and stem cell transplant. Following a bone marrow or stem cell allograft, the transplanted donor cells, e.g., T cells, may attack the patient's (the host's) body. GVHD may be chronic or acute, and may be life-threatening if uncontrolled. Thus, GVHD is an example of an undesired and/or aberrant immune response.

Lymphocyte infiltration occurs in many diseases and conditions including cancers, vascular injury, spinal cord injury, allergy and asthma. Schottenfeld and Beebe-Dimmer (2006) CA 56: 69. Zhu et al. (2002) Arteriosclerosis, Thrombosis Vasc Biol. 22: 450; (2002) Jones et al. (2002) J. Neurosci. 22: 2690; Gaga et al., (1991) J Immunol. 147:816-22; Boushey H A and J V Fahy (1995) Environ Health Perspect. 103 Suppl 6:229-233. Disorders characterized by inappropriate or aberrant lymphocyte infiltration are also considered to be diseases characterized by an excessive, aberrant or undesired immune response and therefore may be treated according to the methods of the present invention.

In certain hematological cancers, such as multiple myeloma, a malignancy of B-cells and plasma cells, treatment often involves both anti-cancer (e.g., cytotoxic) agents and immunosuppressants such as dexamethasone to reduce the aberrant immune response, (i.e., B-cell proliferation). A monoclonal antibody that binds S1P with high affinity and specificity has been shown to slow tumor progression and associated angiogenesis in several animal models of human cancer. Visentin et al., (2006) Cancer Cell 9: 225-238. The applicants believe that the anti-S1P antibody could be effective as an anti-cancer agent by virtue not only of its anti-tumorigenic activity, but also because it may be immunosuppressant. It is believed to be particularly useful for treatment of multiple myeloma and other hematological malignancies characterized by an aberrant or unwanted involvement, infiltration or proliferation of lymphocytes and their products.

B. Bioactive Signaling Lipids

Lipids and their derivatives are now recognized as important targets for medical research, not as just simple structural elements in cell membranes or as a source of energy for β-oxidation, glycolysis or other metabolic processes. In particular, certain bioactive lipids function as signaling mediators important in animal and human disease. Although most of the lipids of the plasma membrane play an exclusively structural role, a small proportion of them are involved in relaying extracellular stimuli into cells. These lipids are referred to as "bioactive lipids" or, alternatively, "bioactive signaling lipids." "Lipid signaling" refers to any of a number of cellular signal transduction pathways that use cell membrane lipids as second messengers, as well as referring to direct interaction of a lipid signaling molecule with its own specific receptor. Lipid signaling pathways are activated by a variety of extracellular stimuli, ranging from growth factors to inflammatory cytokines, and regulate cell fate decisions such as apoptosis, differentiation and proliferation. Research into bioactive lipid signaling is an area of intense scientific investigation as more and more bioactive lipids are identified and their actions characterized.

Examples of bioactive lipids include the eicosanoids (including the cannabinoids, leukotrienes, prostaglandins, lipoxins, epoxyeicosatrienoic acids, and isoeicosanoids), non-eicosanoid cannabinoid mediators, phospholipids and their derivatives such as phosphatidic acid (PA) and phosphatidylglycerol (PG), platelet activating factor (PAF) and cardiolipins as well as lysophospholipids such as lysophosphatidyl choline (LPC) and various lysophosphatidic acids (LPA). Bioactive signaling lipids also include the sphingolipids such as sphingomyelin, ceramide, ceramide-1-phosphate, sphingosine, sphingosylphosphoryl choline, sphinganine, sphinganine-1-phosphate (Dihydro-S1P) and sphingosine-1-phosphate. Sphingolipids and their derivatives represent a group of extracellular and intracellular signaling molecules with pleiotropic effects on important cellular processes. Other examples of bioactive signaling lipids include phosphatidylserine (PS), phosphatidylinositol (PI), phosphatidylethanolamine (PEA), diacylglyceride (DG), sulfatides, gangliosides, and cerebrosides.

1. Lysolipids

Lysophospholipids (LPLs), also known as lysolipids, are low molecular weight (typically less than about 500 dalton) lipids that contain a single hydrocarbon backbone and a polar head group containing a phosphate group. Some lysolipids are bioactive signaling lipids. Two particular examples of medically important bioactive lysolipids are LPA (glycerol backbone) and S1P (sphingoid backbone). The structures of selected LPAs, S1P, and dihydro S1P are presented below.

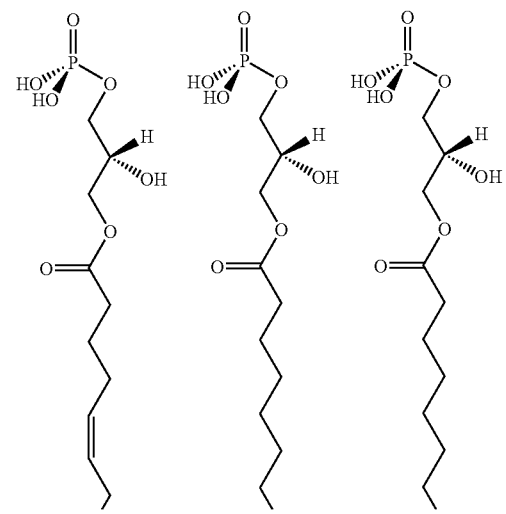

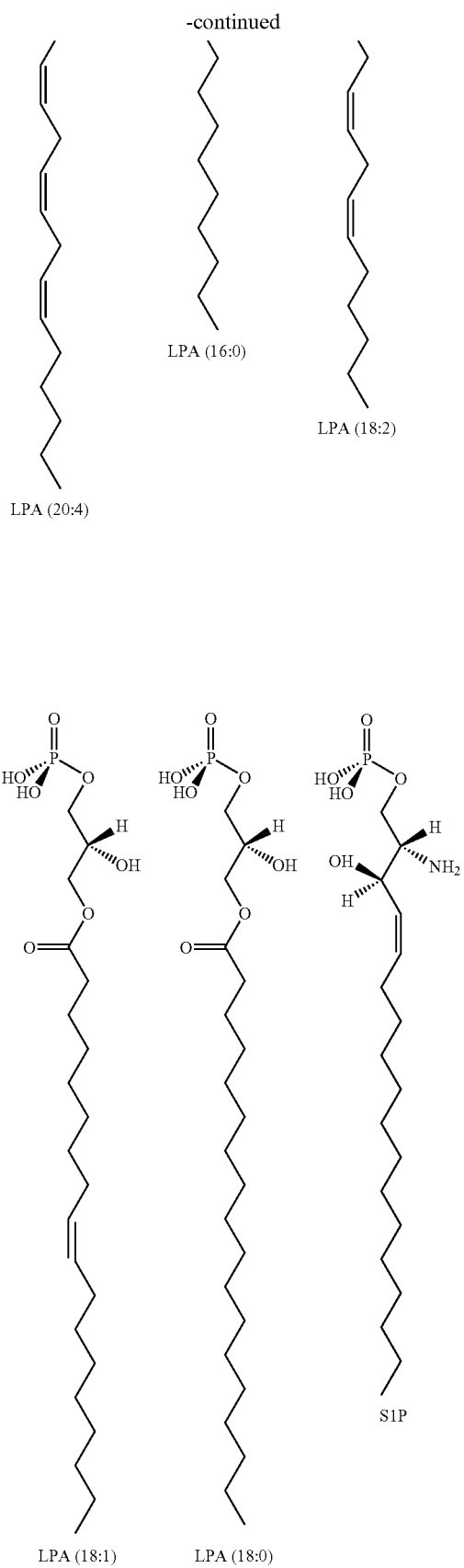
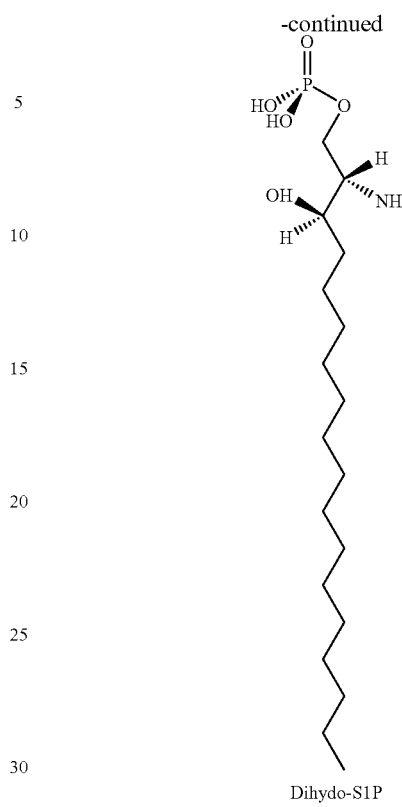

LPA is not a single molecular entity but a collection of endogenous structural variants with fatty acids of varied lengths and degrees of saturation. Fujiwara et al. (2005), J Biol Chem, 280: 35038-35050. The structural backbone of the LPAs is derived from glycerol-based phospholipids such as phosphatidylcholine (PC) or phosphatidic acid (PA). In the case of lysosphingolipids such as S1P, the fatty acid of the ceramide backbone is missing. The structural backbone of S1P, dihydro S1P (DHS1P), and sphingosylphosphorylcholine (SPC) is based on sphingosine, which is derived from sphingomyelin.

LPA and S1P regulate various cellular signaling pathways by binding to the same class of multiple transmembrane domain G protein-coupled (GPCR) receptors. Chun J, Rosen H (2006), Current Pharm Des, 12: 161-171 and Moolenaar W H (1999), Experimental Cell Research, 253: 230-238. The S1P receptors are designated as S1P1, S1P2, S1P3, S1P4 and S1P5 (formerly EDG-1, EDG-5/AGR16, EDG-3, EDG-6 and EDG-8) and the LPA receptors designated as LPA1, LPA2, LPA3 (formerly, EDG-2, EDG-4, and EDG-7). A fourth LPA receptor of this family has been identified for LPA (LPA4), and other putative receptors for these lysophospholipids have also been reported.

LPA and S1P have been shown to play a role in the immune response through modulation of immune-related cells such as T- and B-lymphocytes. These lipids promote T-cell migration to sites of immune response and regulate proliferation of T cells as well as secretion of various cytokines. Chun J and Rosen H, (2006) Curr Pharm Des. 12:161-171; Huang et al., (2002) Biophys Biochim Acta 1582:161-167; Rosen H and E J Goetzl (2005) Nat Rev Immunol (2005) 5:560-70. In particular, S1P is thought to control egress of lymphocytes into the peripheral circulation. Thus agents which bind LPA and S1P are believed to be useful in methods for decreasing an undesired, excessive or aberrant immune response, and for treating diseases and conditions, including certain hematological cancers and autoimmune disorders that are associated with an undesired, excessive or aberrant involvement of lymphocytes and or an aberrant immune response.

a. Sphingosine-1-Phosphate

S1P is a mediator of cell proliferation and protects from apoptosis through the activation of survival pathways. Maceyka et al. (2002), Biochim Biophys Acta, 1585: 192-201; Spiegel S. et al. (2003), Nat Revs Molec Cell Biol, 4: 397-407. It has been proposed that the balance between ceramide/sphingosine (CER/SPH) levels and S1P provides a rheostat mechanism that decides whether a cell is directed into the death pathway or is protected from apoptosis. The key regulatory enzyme of the rheostat mechanism is sphingosine kinase (SPHK) whose role is to convert the death-promoting bioactive signaling lipids (CER/SPH) into the growth-promoting S1P. S1P has two fates: S1P can be degraded by S1P lyase, an enzyme that cleaves S1P to phosphoethanolamine and hexadecanal, or, less common, hydrolyzed by S1P phosphatase to SPH.

S1P is abundantly generated and stored in platelets, which contain high levels of SPHK and lacks the enzymes for S1P degradation. When platelets are activated, S1P is secreted. In addition, other cell types, for example, mast cells, are also believed to be capable of secreting S1P. Once secreted, S1P is thought to be bound at high concentrations on carrier proteins such as serum albumin and lipoproteins. S1P is found in high concentrations in plasma, with concentrations in the range of 0.5-5 uM having been reported. Though primarily extracellular, intracellular actions of S1P have also been suggested (see, e.g., Spiegel S, Kolesnick R (2002), Leukemia, 16: 1596-602; Suomalainen et al (2005), Am J Pathol, 166: 773-81).

Widespread expression of the cell surface S1P receptors allows S1P to influence a diverse spectrum of cellular responses, including proliferation, adhesion, contraction, motility, morphogenesis, differentiation, and survival. This spectrum of response appears to depend upon the overlapping or distinct expression patterns of the S1P receptors within the cell and tissue systems. In addition, crosstalk between S1P and growth factor signaling pathways, including platelet-derived growth factor (PDGF), vascular endothelial growth factor (VEGF), transforming growth factor beta (TGFb) and basic fibroblastic growth factor (bFGF), have recently been demonstrated (see, e.g., Baudhuin, et al. (2004), FASEB J, 18: 341-3). Because regulation of various cellular processes involving S1P has particular impact on neuronal signaling, vascular tone, wound healing, immune cell trafficking, reproduction, and cardiovascular function, among others, it is believed that alterations of endogenous levels of S1P within these systems can have detrimental effects, eliciting several pathophysiologic conditions, including cancer, heart failure, ocular disease and infectious and autoimmune diseases. We propose that a potentially effective strategy for treating autoimmune disorders is to reduce the biologically available extracellular levels of S1P. The applicants have developed a murine monoclonal antibody that is specific for S1P. This represents the first successfully created monoclonal antibody against a bioactive signaling sphingolipid target. The antibody acts as a molecular sponge to selectively absorb S1P from the extracellular fluid, lowering the effective concentration of S1P. It selectively binds and neutralizes S1P with picomolar affinity in biologic matrices. Visentin et al., (2006) Cancer Cell 9:225-238. Interestingly, S1P is conserved across species, unlike most proteinaceous drug targets. Human S1P is identical to murine and monkey S1P, for example.

As used herein, "sphingosine-1-phosphate" or S1P refers to sphingosine-1-phosphate [sphingene-1-phosphate; D-erythro-sphingosine-1-phosphate; sphing-4-enine-1-phosphate; (E,2S,3R)-2-amino-3-hydroxy-octadec-4-enoxy] phosphonic acid; CAS 26993-30-6] and its variants, S1P and DHS1P (dihydro sphingosine-1-phosphate [sphinganine-1-phosphate; [(2S,3R)-2-amino-3-hydroxy-octadecoxy]phosphonic acid; D-Erythro-dihydro-D-sphingosine-1-phosphate; CAS 19794-97-9] and sphingosylphosphorylcholine. Variants of S1P and LPA, as used herein, include analogs and derivatives of S1P and LPA, respectively, which function similarly, or might be expected to function similarly, to the parent molecule.

Inhibition of S1P signaling yields useful immunosuppression and amelioration of autoimmune disorders:

FTY720 (FTY; Fingolimod; 2-amino-2-(2-[4-octylphenyl]ethyl)-1,3-propanediol hydrochloride), a small molecule sphingosine analog, is a novel immunosuppressive drug that acts by altering lymphocyte trafficking, resulting in peripheral blood lymphopenia and increased lymphocyte counts in lymph nodes. FTY mediates its immune-modulating effects by binding to some of the S1P receptors expressed on lymphocytes. Bohler T et al. (2005), Transplantation, 79: 492-5.

It is believed that FTY acts by an interaction with the FTY receptors, S1P1, S1P3, S1P4 and S1P5 (but not S1P2). It is believed that initially FTY activates S1P receptors and acts as a S1P agonist. Then, FTY causes an abnormal internalization of these receptors, inactivating them by removing them from the plasma membrane. Thus while it may act initially as an agonist of S1P receptors, its long-term effects are of a functional antagonist. Massberg, S and U. von Andrian (2006) New Engl. J. Med. 355:1088-1091. The drug is administered orally and a single oral dose reduced peripheral lymphocyte counts by 30-70%. FTY reduced T-cell subset, CD4(+) cells more than CD8(+) cells. Bohler et al. (2004), Nephrol Dial Transplant, 19: 702-13. FTY treated mice showed a significant prolongation of orthotopic corneal-graft survival when administered orally. Zhang et al. (2003), Transplantation, 76: 1511-3. FTY oral treatment also significantly delayed rejection and decreased its severity in a rat-to-mouse model of corneal xenotransplantation. Sedlakova et al. (2005), Transplantation, 79, 297-303. Given the known pathogenesis of allograft rejection combined with these data suggesting that modulating the effects of the S1P signaling can improve graft survival, it is believed that agents, including antibodies that bind to, and thereby decrease the effective concentration of, bioactive lipids will also be useful in treatment of allograft rejection and other conditions characterized by an aberrant, undesired or excessive immune response.

S1P1 is involved in lymphocyte trafficking and is required for egress of lymphocytes from the thymus and secondary lymphoid organs (spleen, lymph nodes and mucosal associated lymphatic tissues such as adenoids, tonsils, appendix and Peyer's patches), which are the sites of initiation of the immune response. Lymphocytes circulate from the blood to the lymph nodes and into the lymph. Egress of lymphocytes (back to circulation) from the lymph is via the thoracic duct. Lymphocytes also recirculate via the spleen. The S1P1 inhibitor FTY causes rapid lymphopenia (reduction of lymphocytes in the blood) which is striking (10-100 fold loss in several hours) and is accompanied by a reduction of lymphocytes in lymph. An increase in lymphocytes in secondary lymphoid organs and the thymus can be seen. Thus, FTY's immune suppressive effects are believed to be due to blockage of S1P1-mediated lymphocyte egress from these organs into the circulation which would deliver the lymphocytes to the site of immune response. For review see Cyster, J., (2005) Ann. Rev.

Immunol. 23:127-159. This blockage of lymphocyte egress can also be referred to as lymphocyte sequestration and is believed to account for FTY's efficacy in animal models of transplant and autoimmune disorders.

Agents and antibodies that bind to S1P and prevent ligand interaction with its complement of receptors could have a similar effect to FTY but by a different mechanism. Without being limited to a particular theory, the applicants believe that agents like anti-S1P antibodies could act by preventing S1P binding to its complement of receptors on lymphocytes and other cells involved in lymphocyte trafficking. Silencing the receptors with an anti-S1P mAb would have a similar effect to FTY's ability to down-regulate receptor presence on the surface membrane of a cell. Further, it is believed that by lowering the effective concentration of S1P, the anti-S1P mAb could act to reduce the S1P gradient between lymphatic tissue and blood. This gradient might be critical for lymphocyte egress and may act in concert with S1P activation of receptors on lymphocyte surfaces.

The marginal zone of the spleen lies between the non-lymphoid red pulp and the lymphoid white pulp of the spleen. As a result, B lymphocyte cells in the marginal zone are continuously exposed to blood (and with it, antigens). The factors that direct B cells to the marginal zone are not well understood. Treatment with FTY causes displacement of B cells from the marginal zone to lymphoid follicles, leading to the conclusion that S1P1 promotes localization of marginal zone B cells to the splenic marginal zone. Cinamon et al., (2004) Nature Immunol. 5:713-720. Thus in addition to its role in lymphocyte egress, S1P signaling also plays a role in lymphoid tissue compartmentalization.

As can be seen in Example 1 hereinbelow, the anti-S1P mAb developed by Lpath, Inc. causes lymphopenia in mice. It can be argued that by acting as a molecular sponge to reduce the effective concentration of S1P, the antibody may be depriving the S1P receptors of their ligand and reduce the S1P gradient between lymphoid tissue and the peripheral circulation. In so doing, lymphocyte egress from lymphatics and spleen may be retarded or reduced.

Multiple sclerosis (MS) is an autoimmune disease in which an immune response directed at oligodendrocytes result in focal damage to the myelin sheaths in the central nervous system (CNS). This results in severe, generally progressive, neurological impairment and disability. A small, placebo-controlled clinical trial of FTY720 has been carried out in patients with the relapsing form of MS. FTY or placebo was given orally once per day for six months and patients who received the FTY showed rapid reduction in disease activity, as measured by a significant reduction in relapse rate. A reduction in number of gadolinium-enhanced CNS lesions measured by MRI was also demonstrated. In a switching study, patients who started on placebo showed improvement when switched to FTY. Kappos et al., (2006) N. Engl. J. Med. 355:1124-1140, and review by Massberg S and von Andrian, U. (2006) N. Engl. J. Med. 355: 1088-1091.

FTY (FTY or FTY-P) has been shown to attenuate the development of dextran sulfate sodium (DSS)-induced colitis and CD4+CD62L+ T cell transfer colitis. FTY was effective in preventing body weight loss in both models, and the disease activity index and histological colitis score were significantly lower in FTY-treated mice than in the non-treated mice. In both colitis models, FTY prevented the infiltration of CD4+ T cells into the inflamed colonic lamina propria and for that reason the authors suggest FTY as a possible clinical treatment for inflammatory bowel disease (IBD). Deguchi et al., (2006) Oncol Rep. 16:699-703.

FTY is believed to interfere with S1P signaling by binding to S1P receptors. It is believed that similar effects will be obtained using agents such as Lpath's anti-S1P mAb, which bind directly to S1P and thereby decrease the effective concentration of S1P. This is also referred to as neutralizing S1P. Examples of such agents are immune-derived moieties (e.g., antibodies and antibody fragments), small molecules, aptamers, S1P receptor fragments and the like. Thus it is believed that such agents will be effective against autoimmune diseases and other diseases characterized by an aberrant, excessive or undesired immune response.

U.S. Pat. No. 6,098,631 (Holoshitz et al.) discloses methods and compositions for treating and diagnosing autoimmune diseases using compounds that inhibit proliferation and induce apoptosis, including compounds that are inhibitors of the sphingomyelin signal transduction pathway.

b. Lysophosphatic Acids (LPA)

LPAs have long been known as precursors of phospholipid biosynthesis in both eukaryotic and prokaryotic cells, but LPAs have emerged only recently as signaling molecules that are rapidly produced and released by activated cells, notably platelets, to influence target cells by acting on specific cell-surface receptor (see, e.g., Moolenaar et al. (2004), BioEssays, 26: 870-881 and van Leewen et al. (2003), Biochem Soc Trans, 31: 1209-1212). Besides being synthesized and processed to more complex phospholipids in the endoplasmic reticulum, LPA can be generated through the hydrolysis of pre-existing phospholipids following cell activation; for example, the sn-2 position is commonly missing a fatty acid residue due to de-acylation, leaving only the sn-3 hydroxyl esterified to a fatty acid. Moreover, a key enzyme in the production of LPA, autotaxin (lysoPLD/NPP2), may be the product of an oncogene, as many tumor types up-regulate autotoxin. Brindley (2004), J Cell Biochem, 92: 900-12. The concentrations of LPA in human plasma and serum have been reported, including determinations made using sensitive and specific LC/MS procedures' Baker et al. (2001), Anal Biochem, 292: 287-295. For example, in freshly prepared human serum allowed to sit at 25° C. for one hour, LPA concentrations have been estimated to be approximately 1.2 mM, with the LPA analogs 16:0, 18:1, 18:2, and 20:4 being the predominant species. Similarly, in freshly prepared human plasma allowed to sit at 25° C. for one hour, LPA concentrations have been estimated to be approximately 0.7 mM, with 18:1 and 18:2 LPA being the predominant species.

LPAs influence a wide range of biological responses, including induction of cell proliferation, stimulation of cell migration and neurite retraction, gap junction closure, and even slime mold chemotaxis. Goetzl et al. (2002), Scient World J, 2: 324-338. The body of knowledge about the biology of LPA continues to grow as more and more cellular systems are tested for LPA responsiveness. For example:

Wound healing: It is now known that, in addition to stimulating cell growth and proliferation, LPA promote cellular tension and cell-surface fibronectin binding, which are important events in wound repair and regeneration. Moolenaar et al. (2004), BioEssays, 26: 870-881.

Apoptosis: Recently, anti-apoptotic activity has also been ascribed to LPA, and it has recently been reported that peroxisome proliferation receptor gamma is a receptor/target for LPA. Simon et al. (2005), J Biol Chem, 280: 14656-14662.

Blood vessel maturation: Autotaxin, a secreted lysophospholipase D responsible for producing LPAs, is essential for blood vessel formation during development. van Meeteren et al. (2006), Mol Cell Biol, 26: 5015-22. In addition, unsaturated LPAs were identified as major contributors to the induction of vascular smooth muscle cell dedifferentiation. Hayashi et al. (2001), Circ Res, 89: 251-8.

Edema and vascular permeability: LPA induces plasma exudation and histamine release in mice. Hashimoto et al. (2006), J Pharmacol Sci, 100: 82-7.

Inflammation: LPA acts as inflammatory mediator in human corneal epithelial cells. Zhang et al (2006), Am J Physiol, June 7. LPA participates in corneal wound healing [Liliom K et al (1998), Am. J. Physiol, 274: C1065-C1074] and stimulates the release of ROS in lens tissue [Rao et al. (2004), Molecular Visions, 10: 112-121]. LPA can also re-activate HSV-1 in rabbit cornea. Martin et al. (1999), Molec Vis, 5: 36-42.

Fibrosis and scar formation: LPA inhibits TGF-mediated stimulation of type I collagen mRNA stability via an ERK-dependent pathway in dermal fibroblasts. Sato et al. (2004), Matrix Biol, 23: 353-61. Moreover, LPA have some direct fibrogenic effects by stimulating collagen gene expression and proliferation of fibroblasts. Chen, et al. (2006) FEBS Lett. 580:4737-45.

Immune response: LPA, like S1P, has been shown to play a role in the immune response through modulation of immune-related cells. These lipids promote T-cell migration to sites of immune response and regulate proliferation of T cells as well as secretion of various cytokines. Chun J and Rosen H, (2006) Curr. Pharm Des. 12:161-171; Huang et al., (2002) Biophys. Biochim. Acta 1582:161-167; Rosen H and E J Goetzl (2005) Nat Rev Immunol. (2005) 5:560-70. Thus agents that reduce the effective concentration of LPA, such as Lpath's anti-LPA mAb, are believed to be useful in methods for decreasing an undesired, excessive or aberrant immune response, and for treating diseases and conditions, including autoimmune disorders that are associated with an undesired, excessive or aberrant immune response.

Recently, the applicants have developed several monoclonal antibodies against LPAs. Like the anti-S1P antibody, the anti-LPA antibodies can neutralize various LPAs and mitigate their biologic and pharmacologic action. Anti-LPA antibodies are, therefore, believed to be useful in prevention and/or treatment of immune-related diseases and conditions.

III. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

An "immune-derived moiety" refers to any polyclonal or monoclonal antibody or antibody fragment, variant, or derivative.

An "anti-S1P antibody" or an "immune-derived moiety reactive against S1P" refers to any antibody or antibody-derived molecule that binds S1P.

An "anti-LPA antibody" or an "immune-derived moiety reactive against LPA" refers to any antibody or antibody-derived molecule that binds to all or one or more of the LPAs.

A "bioactive lipid" refers to a lipid signaling molecule. In general, a bioactive lipid does not reside in a biological membrane when it exerts its signaling effects, which is to say that while such a lipid species may exist at some point in a biological membrane (for example, a cell membrane, a membrane of a cell organelle, etc.), when associated with a biological membrane it is not a bioactive lipid but is instead a "structural lipid" molecule. Bioactive lipids are distinguished from structural lipids (e.g., membrane-bound phospholipids) in that they mediate extracellular and/or intracellular signaling and thus are involved in controlling the function of many types of cells by modulating differentiation, migration, proliferation, secretion, survival, and other processes. In vivo, bioactive lipids can be found in extracellular fluids, where they can be complexed with other molecules, for example serum proteins such as albumin and lipoproteins, or in "free" form, i.e., not complexed with another molecule species. As extracellular mediators, some bioactive lipids alter cell signaling by activating membrane-bound ion channels or G-protein coupled receptors that, in turn, activate complex signaling systems that result in changes in cell function or survival. As intracellular mediators, bioactive lipids can exert their actions by directly interacting with intracellular components such as enzymes and ion channels. Representative examples of bioactive lipids include LPA and S1P.

The term "therapeutic agent" means an agent for modulating immune responses, particularly undesired, excessive or aberrant immune responses, including autoimmune responses.

The term "combination therapy" refers to a therapeutic regimen that involves the provision of at least two distinct therapies to achieve an indicated therapeutic effect. For example, a combination therapy may involve the administration of two or more chemically distinct active ingredients, for example, an anti-LPA antibody and an anti-S1P antibody. Alternatively, a combination therapy may involve the administration of an immune-derived moiety reactive against a bioactive lipid and the administration of one or more other chemotherapeutic agents. Combination therapy may, alternatively, involve administration of an anti-lipid antibody together with the delivery of another treatment, such as radiation therapy and/or surgery. Further, a combination therapy may involve administration of an anti-lipid antibody together with one or more other biological agents (e.g., anti-VEGF, TGF, PDGF, or bFGF agent), chemotherapeutic agents and another treatment such as radiation and/or surgery. In the context of combination therapy using two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician. Similarly, when one or more anti-lipid antibody species, for example, an anti-LPA antibody, alone or in conjunction with one or more chemotherapeutic agents are combined with, for example, radiation and/or surgery, the drug(s) may be delivered before or after surgery or radiation treatment.

"Monotherapy" refers to a treatment regimen based on the delivery of one therapeutically effective compound, whether administered as a single dose or several doses over time.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to patentable embodiments, specifically exclude the unpatentable embodiment(s). Also, the claims appended hereto are to be interpreted both to provide the broadest reasonable scope, as well as to preserve their validity. Furthermore, the claims are to be interpreted in a way that (1) preserves their validity and (2) provides the broadest reasonable interpretation under the circumstances, if one or more of the statutory requirements for patentability are amended or if the standards change for assessing whether a particular statutory requirement for patentability is satisfied from the time this application is filed or issues as a patent to a time the validity of one or more of the appended claims is questioned.

The term "pharmaceutically acceptable salt" refers to salts which retain the biological effectiveness and properties of the agents and compounds of this invention and which are not biologically or otherwise undesirable. In many cases, the agents and compounds of this invention are capable of forming acid and/or base salts by virtue of the presence of charged groups, for example, charged amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts, see Berge et al. (1977) J. Pharm. Sci., 66, 1-19.

The terms "separated", "purified", "isolated", and the like mean that one or more components of a sample contained in a sample-holding vessel are or have been physically removed from, or diluted in the presence of, one or more other sample components present in the vessel. Sample components that may be removed or diluted during a separating or purifying step include, chemical reaction products, unreacted chemicals, proteins, carbohydrates, lipids, and unbound molecules.

The term "species" is used herein in various contexts, e.g., a particular species of chemotherapeutic agent. In each context, the term refers to a population of molecules, chemically indistinguishable from each other, of the sort referred in the particular context.

"Specifically associate" and "specific association" and the like refer to a specific, non-random interaction between two molecules, which interaction depends on the presence of structural, hydrophobic/hydrophilic, and/or electrostatic features that allow appropriate chemical or molecular interactions between the molecules.

Herein, "stable" refers to an interaction between two molecules (e.g., binding of an anti-LPA or anti-S1P antibody to its target bioactive lipid) that is sufficiently strong such that the interaction of the molecules can be maintained for the desired purpose or manipulation.

A "subject" or "patient" refers to an animal in which treatment can be effected by molecules of the invention. The animal may have, be at risk for, or be believed to have or be at risk for a disease or condition that can be treated by compositions and/or methods of the present invention. Animals that can be treated in accordance with the invention include vertebrates, with mammals such as bovine, canine, equine, feline, ovine, porcine, and primate (including humans and non-human primates) animals being particularly preferred examples.

A "therapeutically effective amount" (or "effective amount") refers to an amount of an active ingredient, e.g., an agent according to the invention, sufficient to effect treatment when administered to a subject or patient. Accordingly, what constitutes a therapeutically effective amount of a composition according to the invention may be readily determined by one of ordinary skill in the art. In the context of therapy for autoimmune or other immune-related disorders, a therapeutically effective amount is one that produces an objectively measured change in one or more parameters associated with an immune response. Nonlimiting examples of such parameters include: number of circulating T cells or lymphocytes, sequestration (e.g., accumulation) of T cells in the lymphoid organ(s), and level of lymphocyte activation.

Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy (i.e., a therapeutic regimen that employs only one chemical entity as the active ingredient).

The term "treatment" or "treating" of a disease or disorder includes preventing or protecting against the disease or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between preventing and suppressing a disease or disorder since the ultimate inductive event or events may be unknown or latent. Accordingly, the term "prophylaxis" will be understood to constitute a type of treatment that encompasses both preventing and suppressing. The term treatment thus includes prophylaxis.

The term "therapeutic regimen" means any treatment of a disease or disorder using chemotherapeutic drugs, radiation therapy, surgery, gene therapy, DNA vaccines and therapy, antisense-based therapies including siRNA therapy, anti-angiogenic therapy, immunotherapy, bone marrow transplants, aptamers and other biologics such as antibodies and antibody variants, receptor decoys and other protein-based therapeutics.

SUMMARY OF THE INVENTION

In accordance with the present invention, methods are provided for decreasing an immune response in an animal, including a human, comprising administering to the animal an agent that binds a bioactive lipid and reduces the effective concentration of the bioactive lipid. The immune response is generally an aberrant, excessive or undesired immune response, and may be an autoimmune response.

Also provided are methods of treating diseases or conditions characterized by an aberrant, excessive or undesired immune response, comprising administering an agent that binds a bioactive lipid and reduces the effective concentration of said bioactive lipid. The disease or condition may be an autoimmune disease or condition or an undesired tissue rejection reaction. Disorders characterized by inappropriate or aberrant lymphocyte infiltration are also considered to be diseases characterized by an excessive, aberrant or undesired immune response and therefore may be treated according to the methods of the present invention.

In some embodiments of these methods, the bioactive lipid may be a sphingolipid or sphingolipid metabolite or a lysolipid or lysolipid metabolite, including S1P, LPA or a variant thereof. In some embodiments the agent that binds the bioactive lipid is an antibody, such as a monoclonal antibody, which may be a humanized monoclonal antibody. The agent may be an antibody fragment or another type of agent as described hereinbelow.

These and other aspects and embodiments of the invention are discussed in greater detail in the sections that follow.

DETAILED DESCRIPTION OF THE INVENTION

One way to control the amount of undesirable bioactive signaling lipids is by providing a composition that binds one or more of these lipids. The present invention describes methods for decreasing an immune response and for treating conditions associated with an aberrant, unwanted or excessive immune response. These methods comprise administering an agent that binds to a bioactive signaling lipid and decreases the effective concentration of the bioactive lipid. Antibodies and other compounds that bind to bioactive signaling lipids may be used as therapeutic sponges that reduce the effective level of lipid. When a compound is stated to be free, the compound is not in any way restricted from reaching the site or sites where it exerts its undesirable effects. Typically, a free compound is present in the cardiovascular system or lymphatics, which either is or contains the site(s) of action of the free compound, or from which a compound can freely migrate to its site(s) of action. A free compound may also be available to be acted upon by any enzyme that converts the compound into an undesirable compound.

I. Agents Useful in the Invention

A. Immune-Derived Moieties

Several antibodies have recently been approved for therapeutic use in humans by the Federal Drug Administration. Kling (1999) Mod. Drug Disc. 2:33 45. In one aspect of lipid-based therapy, antibodies that bind bioactive signaling lipids can be delivered to a patient, e.g., incorporated into pharmaceutical compositions, medical devices, and the like, for use in therapy. Such methods may work by, e.g., modulating the effective concentration of a target bioactive lipid in tissues or bodily fluids, or by removing target lipid from blood in vivo or ex vivo.

The term "immune-derived moiety", which includes antibodies (Ab) or immunoglobulins (Ig), refers to any form of a peptide, polypeptide derived from, modeled after or encoded by, an immunoglobulin gene, or a fragment of such peptide or polypeptide that is capable of binding an antigen or epitope [see, eg, Immunobiology, 5th Edition, Janeway, Travers, Walport, Shlomchiked. (editors), Garland Publishing (2001)]. In the present invention, the antigen is a bioactive lipid molecule. Antibody molecules or immunoglobulins are large glycoprotein molecules with a molecular weight of approximately 150 kDa, usually composed of two different kinds of polypeptide chain. One polypeptide chain, termed the "heavy" chain (H) is approximately 50 kDa. The other polypeptide, termed the "light" chain (L), is approximately 25 kDa. Each immunoglobulin molecule usually consists of two heavy chains and two light chains. The two heavy chains are linked to each other by disulfide bonds, the number of which varies between the heavy chains of different immunoglobulin isotypes. Each light chain is linked to a heavy chain by one covalent disulfide bond. In any given naturally occurring antibody molecule, the two heavy chains and the two light chains are identical, harboring two identical antigen-binding sites, and are thus said to be divalent, i.e., having the capacity to bind simultaneously to two identical molecules.

The light chains of antibody molecules from any vertebrate species can be assigned to one of two clearly distinct types, kappa (κ) and lambda (λ), based on the amino acid sequences of their constant domains. The ratio of the two types of light chain varies from species to species. As a way of example, the average κ to λ ratio is 20:1 in mice, whereas in humans it is 2:1 and in cattle it is 1:20.

The heavy chains of antibody molecules from any vertebrate species can be assigned to one of five clearly distinct types, called isotypes, based on the amino acid sequences of their constant domains. Some isotypes have several subtypes. The five major classes of immunoglobulin are immunoglobulin M (IgM), immunoglobulin D (IgD), immunoglobulin G (IgG), immunoglobulin A (IgA), and immunoglobulin E (IgE). IgG is the most abundant isotype and has several subclasses (IgG1, 2, 3, and 4 in humans). The Fc fragment and hinge regions differ in antibodies of different isotypes, thus determining their functional properties. However, the overall organization of the domains is similar in all isotypes.

The term "variable region" refers to the N-terminal portion of the antibody molecule or a fragment thereof. In general, each of the four chains has a variable (V) region in its amino terminal portion, which contributes to the antigen-binding site, and a constant (C) region, which determines the isotype. The light chains are bound to the heavy chains by many noncovalent interactions and by disulfide bonds and the V regions of the heavy and light chains pair in each arm of antibody molecule to generate two identical antigen-binding sites. Some amino acid residues are believed to form an interface between the light- and heavy-chain variable domains [see Kabat et al. (1991), Sequences of Proteins of Immunological Interest, Fifth Edition, National Institute of Health, Bethesda, Md. and Clothia et al. (1985), J. Mol. Biol, vol 186: 651].

Of note, variability is not uniformly distributed throughout the variable domains of antibodies, but is concentrated in three segments called "complementarity-determining regions" (CDRs) or "hypervariable regions" both in the light-chain and the heavy-chain variable domains. The more highly conserved portions of variable domains are called the "framework region" (FR). The variable domains of native heavy and light chains each comprise four FR regions connected by three CDRs. The CDRs in each chain are held together in close proximity by the FR regions and, with the CDRs from the other chains, form the antigen-binding site of antibodies [see Kabat et al. (1991), Sequences of Proteins of Immunological Interest, Fifth Edition, National Institute of Health, Bethesda, Md.]. Collectively, the 6 CDRs contribute to the binding properties of the antibody molecule for the antigen. However, even a single variable domain (or half of an Fv, comprising only three CDRs specific for an antigen) has the ability to recognize and bind antigen [see Pluckthun (1994), in The Pharmacology of Monoclonal Antibodies, vol. 113, Rosenburg and Moore eds., Springer-Verlag, New York, pp. 269-315].

The term "constant domain" refers to the C-terminal region of an antibody heavy or light chain. Generally, the constant domains are not directly involved in the binding properties of an antibody molecule to an antigen, but exhibit various effector functions, such as participation of the antibody in antibody-dependent cellular toxicity. Here, effector functions refer to the different physiological effects of antibodies (e.g., opsonization, cell lysis, mast cell, basophil and eosinophil degranulation, and other processes) mediated by the recruitment of immune cells by the molecular interaction between the Fc domain and proteins of the immune system. The isotype of the heavy chain determines the functional properties of the antibody. Their distinctive functional properties are conferred by the carboxy-terminal portions of the heavy chains, where they are not associated with light chains.

As used herein, "antibody fragment" refers to a portion of an intact antibody that includes the antigen binding site or variable regions of an intact antibody, wherein the portion can be free of the constant heavy chain domains (e.g., CH2, CH3, and CH4) of the Fc region of the intact antibody. Alternatively, portions of the constant heavy chain domains (e.g., CH2, CH3, and CH4) can be included in the antibody fragment. Examples of antibody fragments are those that retain antigen-binding and include Fab, Fab, F(ab)2, Fd, and Fv fragments; diabodies; triabodies; single-chain antibody molecules (sc-Fv); minibodies, nanobodies, and multispecific antibodies formed from antibody fragments. By way of example, a Fab fragment also contains the constant domain of a light chain and the first constant domain (CH1) of a heavy chain.

The term "variant" refers to an amino acid sequence which differs from the native amino acid sequence of an antibody by at least one amino acid residue or modification. A "native" or "parent" or "wild-type" amino acid sequence refers to the amino acid sequence of an antibody found in nature. Variants of the antibody molecule include, but are not limited to, changes within a variable region or a constant region of a light chain and/or a heavy chain, including the hypervariable or CDR region, the Fc region, the Fab region, the CH1 domain, the CH2 domain, the CH3 domain, and the hinge region.

The term "specific" refers to the selective binding of an antibody to its target epitope. Antibody molecules can be tested for specificity of binding by comparing binding of the antibody to the desired antigen to binding of the antibody to unrelated antigen or analog antigen or antigen mixture under a given set of conditions. Preferably, an antibody according to the invention will lack significant binding to unrelated antigens, or even analogs of the target antigen. Here, the term "antigen" refers to a molecule that is recognized and bound by an antibody molecule or immune-derived moiety that binds to the antigen. The specific portion of an antigen that is bound by an antibody is termed the "epitope". A "hapten" refers to a small molecule that can, under most circumstances, elicit an immune response (i.e., act as an antigen) only when attached to a carrier molecule, for example, a protein, polyethylene glycol (PEG), colloidal gold, silicone beads, and the like. The carrier may be one that also does not elicit an immune response by itself.

The term "antibody" is used in the broadest sense, and encompasses monoclonal, polyclonal, multispecific (e.g., bispecific, wherein each arm of the antibody is reactive with a different epitope or the same or different antigen), minibody, heteroconjugate, diabody, triabody, chimeric, and synthetic antibodies, as well as antibody fragments that specifically bind an antigen with a desired binding property and/or biological activity.

The term "monoclonal antibody" (mAb) refers to an antibody, or population of like antibodies, obtained from a population of substantially homogeneous antibodies, and is not to be construed as requiring production of the antibody by any particular method. For example, monoclonal antibodies can be made by the hybridoma method first described by Kohler and Milstein [(1975), Nature, 256: 495-497], or by recombinant DNA methods.

The term "chimeric antibody" (or "chimeric immunoglobulin") refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. Cabilly et al. (1984), infra; Morrison et al., Proc. Natl. Acad. Sci. U.S.A. 81:6851.

The term "humanized antibody" refers to forms of antibodies that contain sequences from non-human (eg, murine) antibodies as well as human antibodies. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins. For the most part, humanized antibodies are human immunoglobulins (recipient antibody) in which residues from a complementary-determining region (CDR) of the recipient are replaced by residues from a CDR of a non-human species (donor antibody) such as mouse, rat, camel, bovine, goat, or rabbit having the desired properties. Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1; Queen et al. (1989) Proc. Natl Acad. Sci. USA, vol 86:10029-10033).

The term "bispecific antibody" can refer to an antibody, or a monoclonal antibody, having binding properties for at least two different epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. Alternatively, bispecific antibodies can be prepared using chemical linkage. Bispecific antibodies include bispecific antibody fragments.

The term "heteroconjugate antibody" can refer to two covalently joined antibodies. Such antibodies can be prepared using known methods in synthetic protein chemistry, including using crosslinking agents. As used herein, the term "conjugate" refers to molecules formed by the covalent attachment of one or more antibody fragment(s) or binding moieties to one or more polymer molecule(s).

The term "biologically active" refers to an antibody or antibody fragment that is capable of binding the desired epitope and in some way exerting a biologic effect. Biological effects include, but are not limited to, the modulation of a growth signal, the modulation of an anti-apoptotic signal, the modulation of an apoptotic signal, the modulation of the effector function cascade, and modulation of other ligand interactions.

The term "recombinant DNA" refers to nucleic acids and gene products expressed therefrom that have been engineered, created, or modified by man. Recombinant polypeptides or proteins are polypeptides or proteins produced by recombinant DNA techniques, for example, from cells transformed by an exogenous DNA construct encoding the desired polypeptide or protein. Synthetic polypeptides or proteins are those prepared by chemical synthesis.

The term "expression cassette" refers to a nucleotide molecule capable of affecting expression of a structural gene (i.e., a protein coding sequence, such as an antibody) in a host compatible with such sequences. Expression cassettes include at least a promoter operably linked with the polypeptide-coding sequence, and, optionally, with other sequences, e.g., transcription termination signals. Additional regulatory elements necessary or helpful in effecting expression may also be used, e.g., enhancers. Thus, expression cassettes include plasmids, expression vectors, recombinant viruses, any form of recombinant naked DNA vector, and the like.

1. Antibody to S1P

Visentin et al. describe a murine monoclonal antibody that binds S1P with extremely high affinity and specificity. This antibody was shown to slow tumor progression and associated angiogenesis in several animal models of human cancer. Cancer Cell (2006) 9: 225-238.

A humanized monoclonal antibody (LT1009) has been derived from the murine anti-S1P antibody (LT1002). As compared to the murine anti-S1P antibody from which it was derived, the humanized form exhibits an S1P binding affinity in the picomolar range, as well as superior stability and in vivo efficacy. Construction, synthesis, purification, and testing of this antibody is described in U.S. patent application Ser. No. 60/854,971, which is commonly owned with the instant invention and hereby incorporated by reference in its entirety for all purposes. It will be understood that, in general, a humanized monoclonal antibody is preferable to a murine antibody or other nonhuman-derived antibody for administration to a human subject.

2. Antibody to LPA

A monoclonal antibody against LPA has been developed. Construction, synthesis, purification, and testing of this antibody are described in U.S. patent application Ser. No. 60/835,569. which is commonly owned with the instant invention and hereby incorporated by reference in its entirety for all purposes.

3. Methods of Preparing Antibodies and Antibody Variants

The antibodies and antibody fragments of the invention may be produced by any suitable method, for example, in vivo (in the case of polyclonal and monospecific antibodies), in cell culture (as is typically the case for monoclonal antibodies, wherein hybridoma cells expressing the desired antibody are cultured under appropriate conditions), in in vitro translation reactions, and in recombinant DNA expression systems (Johnson et al., Methods Enz. 203:88-98, 1991). Antibodies and antibody variants can be produced from a variety of animal cells, preferably from mammalian cells, with murine and human cells being particularly preferred. Antibodies that include non-naturally occurring antibody and T-cell receptor variants that retain only the desired antigen targeting capability conferred by an antigen binding site(s) of an antibody can be produced by known cell culture techniques and recombinant DNA expression systems (see, e.g., Johnson et al., Methods in Enzymol. 203:88-98, 1991; Molloy et al., Mol. Immunol. 32:73-81, 1998; Schodin et al., J. Immunol. Methods 200:69-77, 1997). Recombinant DNA expression systems are typically used in the production of antibody variants such as, e.g., bispecific antibodies and sFv molecules. Preferred recombinant DNA expression systems include those that utilize host cells and expression constructs that have been engineered to produce high levels of a particular protein. Preferred host cells and expression constructs include *Escherichia coli*; harboring expression constructs derived from plasmids or viruses (*bacteriophage*); yeast such as *Sacharomyces cerevisieae* or *Fichia pastoras* harboring episomal or chromosomally integrated expression constructs; insect cells and viruses such as Sf 9 cells and baculovirus; and mammalian cells harboring episomal or chromosomally integrated (e.g., retroviral) expression constructs (for a review, see Verma et al., J. Immunol. Methods 216:165-181, 1998). Antibodies can also be produced in plants (U.S. Pat. No. 6,046,037; Ma et al., Science 268:716-719, 1995) or by phage display technology (Winter et al., Annu. Rev. Immunol. 12:433-455, 1994).

XenoMouse strains are genetically engineered mice in which the murine IgH and Igk loci have been functionally replaced by their Ig counterparts on yeast artificial YAC transgenes. These human Ig transgenes can carry the majority of the human variable repertoire and can undergo class switching from IgM to IgG isotypes. The immune system of the XenoMouse recognizes administered human antigens as foreign and produces a strong humoral response. The use of XenoMouse in conjunction with well-established hybridoma techniques results in fully human IgG mAbs with sub-nanomolar affinities for human antigens. See U.S. Pat. No. 5,770,429, entitled "Transgenic non-human animals capable of producing heterologous antibodies"; U.S. Pat. No. 6,162,963, entitled "Generation of Xenogenetic antibodies"; U.S. Pat. No. 6,150,584, entitled "Human antibodies derived from immunized XenoMice"; U.S. Pat. No. 6,114,598, entitled "Generation of xenogeneic antibodies"; and U.S. Pat. No. 6,075,181, entitled "Human antibodies derived from immunized Xenomice"; for reviews, see Green, (1999) J. Immunol. Methods 231:11-23; Wells, Chem Biol (2000) 7:R185-6; and Davis et al., (1999) Cancer Metastasis Rev; 18:421-5)

B. Receptor Fragments and Ion Channel Fragments

Soluble polypeptides derived from membrane bound, typically hydrophobic, bioactive lipid receptors that retain the receptors' ability to bind lipids may also be used to bind bioactive lipids and lipid metabolites. For example, In the case of Edg (S1P and LPA) receptors, in some instances, particular amino acid residues may be involved in the specificity of sphingolipid binding, i.e., the amino acids that determine which sphingolipid is bound by a specific receptor. Parrill et al.,(2000) J. Biol. Chem. 275:39379-39384; Wang et al., (2001) J. Biol. Chem. 276:49213-49220. Such information may be used to provide soluble receptor fragments comprising receptor residues of interest, i.e., the stretches of amino acids that bind the sphingolipid. Soluble receptor fragments derived from the naturally soluble TNFalpha receptor have been prepared and at least one of these, ENBREL (Etanercept) is in development as a therapeutic agent for arthritis. In addition, modification of such residues may permit the skilled artisan to tailor the binding specificities and/or affinity of soluble receptor fragments.

Soluble receptor fragments of particular interest include fragments of Edg-1, Edg-3, Edg-5, Edg-6 and Edg-8, all of which bind the undesirable sphingolipid sphingosine-1-phosphate (S-1-P). The Edg-1, Edg-3, Edg-5 receptors are of particular interest.

Soluble receptor fragments may be prepared in various ways including but not limited to proteolytic digestion of cells or cellular membrane preparations comprising the receptor [Bartfeld et al., (1979) Biochem Biophys Res Commun. 89:512-9; Borhani et al., (1991) J Mol. Biol. 218:685-9], recombinant DNA technologies [Marlovits et al., (1998(J Mol Recognit. 11:49-51; Huang et al., (1992) J Mol Endocrinol. 8:137-44), or by in vitro synthesis of oligopeptides.

Other agents that may be used to bind bioactive lipids and lipid metabolites include fragments of ion channels that bear one or more S1P binding sites, e.g., TRP channels. Channel fragments that retain the S1P binding site(s) are useful agents for use in the methods of the instant invention.

C. Nucleic Acids

Traditionally, techniques for detecting and purifying target molecules have used polypeptides, such as antibodies, that specifically bind such targets. While nucleic acids have long been known to specifically bind other nucleic acids (e.g., ones having complementary sequences), aptamers (i.e., nucleic acids that bind non-nucleic target molecules) have been disclosed. See, e.g., Blackwell et al., Science (1990) 250:1104-1110; Blackwell et al., Science (1990) 250:1149-1152; Tuerk et al., Science (1990) 249:505-510; Joyce, (1989) Gene 82:83-87; and U.S. Pat. No. 5,840,867 entitled "Aptamer analogs specific for biomolecules".

As applied to aptamers, the term "binding" specifically excludes the Watson-Crick-type binding interactions (i.e., A:T and G:C base-pairing) traditionally associated with the DNA double helix. The term "aptamer" thus refers to a nucleic acid or a nucleic acid derivative that specifically binds to a target molecule, wherein the target molecule is either (i) not a nucleic acid, or (ii) a nucleic acid or structural element thereof that is bound through mechanisms other than duplex- or triplex-type base pairing. Such a molecule is called a non-nucleic molecule herein.

Structures of Nucleic Acids

"Nucleic acids", as used herein, refers to nucleic acids that are isolated from a natural source; prepared in vitro, using techniques such as PCR amplification or chemical synthesis; prepared in vivo, e.g., via recombinant DNA technology; or by any appropriate method. Nucleic acids may be of any shape (linear, circular, etc.) or topology (single-stranded, double-stranded, supercoiled, etc.). The term "nucleic acids" also includes without limitation nucleic acid derivatives such as peptide nucleic acids (PNAs) and polypeptide-nucleic acid conjugates; nucleic acids having at least one chemically modified sugar residue, backbone, internucleotide linkage, base, nucleoside, or nucleotide analog; as well as nucleic acids having chemically modified 5' and/or 3' ends; and nucleic acids having two or more of such modifications. Not all linkages in a nucleic acid need to be identical.

Nucleic acids that are aptamers are often, but need not be, prepared as oligonucleotides. Oligonucleotides include without limitation RNA, DNA and mixed RNA-DNA molecules having sequences of lengths that have minimum lengths of 2, 4, 6, 8, 10, 11, 12, 13, 14, 15, 17, 18, 19, 20, 21, 22, 23, 24 or 25 nucleotides, and maximum lengths of about 100, 75, 50, 40, 25, 20 or 15 or more nucleotides, irrespectively. In general, a minimum of 6 nucleotides, preferably 10 nucleotides, more preferably 14 to 20 nucleotides, is necessary to effect specific binding.

In general, the oligonucleotides may be single-stranded (ss) or double-stranded (ds) DNA or RNA, or conjugates (e.g., RNA molecules having 5' and 3' DNA clamps) or hybrids (e.g., RNA:DNA paired molecules), or derivatives (chemically modified forms thereof). However, single-stranded DNA is preferred, as DNA is often less labile than RNA. Similarly, chemical modifications that enhance an aptamer's specificity or stability are preferred.

Chemical Modifications of Nucleic Acids

Chemical modifications that may be incorporated into aptamers and other nucleic acids include, with neither limitation nor exclusivity, base modifications, sugar modifications, and backbone modifications.

Base modifications: The base residues in aptamers may be other than naturally occurring bases (e.g., A, G, C, T, U, 5MC, and the like). Derivatives of purines and pyrimidines are known in the art; an exemplary but not exhaustive list includes aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine (5MC), N6-methyladenine, 7-methylguanine, 5-methylaminomethyluracil, 5-methoxyaminomethyl-2-thiouracil, beta-D-mannosylqueosine, 5-methoxyuracil, 2-methylthio-N-6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. In addition to nucleic acids that incorporate one or more of such base derivatives, nucleic acids having nucleotide residues that are devoid of a purine or a pyrimidine base may also be included in aptamers.

Sugar modifications: The sugar residues in aptamers may be other than conventional ribose and deoxyribose residues. By way of non-limiting example, substitution at the 2'-position of the furanose residue enhances nuclease stability. An exemplary, but not exhaustive list, of modified sugar residues includes 2' substituted sugars such as 2'-O-methyl-, 2'-O-alkyl, 2'-O-allyl, 2'-S-alkyl, 2'-S-allyl, 2'-fluoro-, 2'-halo, or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside, ethyl riboside or propylriboside.

Backbone modifications: Chemically modified backbones include, by way of non-limiting example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Chemically modified backbones that do not contain a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages, including without limitation morpholino linkages; siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; and amide backbones.

Preparation and Identification of Aptamers

In general, techniques for identifying aptamers involve incubating a preselected non-nucleic target molecule with mixtures (2 to 50 members), pools (50 to 5,000 members) or libraries (50 or more members) of different nucleic acids that are potential aptamers under conditions that allow complexes of target molecules and aptamers to form. By "different nucleic acids" it is meant that the nucleotide sequence of each potential aptamer may be different from that of any other member, that is, the sequences of the potential aptamers are random with respect to each other. Randomness can be introduced in a variety of manners such as, e.g., mutagenesis, which can be carried out in vivo by exposing cells harboring a nucleic acid with mutagenic agents, in vitro by chemical treatment of a nucleic acid, or in vitro by biochemical replication (e.g., PCR) that is deliberately allowed to proceed under conditions that reduce fidelity of replication process; randomized chemical synthesis, i.e., by synthesizing a plurality of nucleic acids having a preselected sequence that, with regards to at least one position in the sequence, is random. By "random at a position in a preselected sequence" it is meant that a position in a sequence that is normally synthesized as, e.g., as close to 100% A as possible (e.g., 5'-C-T-T-A-G-T-3') is allowed to be randomly synthesized at that position (5'-C-T-T-N-G-T-3', wherein N indicates a randomized position where, for example, the synthesizing reaction contains 25% each of A,T,C and G; or x % A, w % T, y % C and z % G, wherein x+w+y+z=100. In later stages of the process, the sequences are increasingly less randomized and consensus sequences may appear; in any event, it is preferred to ultimately obtain an aptamer having a unique nucleotide sequence.

Aptamers and pools of aptamers are prepared, identified, characterized and/or purified by any appropriate technique, including those utilizing in vitro synthesis, recombinant DNA techniques, PCR amplification, and the like. After their formation, target:aptamer complexes are then separated from the uncomplexed members of the nucleic acid mixture, and the nucleic acids that can be prepared from the complexes are candidate aptamers (at early stages of the technique, the aptamers generally being a population of a multiplicity of nucleotide sequences having varying degrees of specificity for the target). The resulting aptamer (mixture or pool) is then substituted for the starting aptamer (library or pool) in repeated iterations of this series of steps. When a limited number (e.g., a pool or mixture, preferably a mixture with less than 10 members, most preferably 1) of nucleic acids having satisfactory specificity is obtained, the aptamer is sequenced and characterized. Pure preparations of a given aptamer are generated by any appropriate technique (e.g., PCR amplification, in vitro chemical synthesis, and the like).

For example, Tuerk and Gold [Science (1990) 249:505-510] disclose the use of a procedure termed systematic evolution of ligands by exponential enrichment (SELEX). In this method, pools of nucleic acid molecules that are randomized at specific positions are subjected to selection for binding to a nucleic acid-binding protein (see, e.g., PCT International Publication No. WO 91/19813 and U.S. Pat. No. 5,270,163). The oligonucleotides so obtained are sequenced and otherwise characterized. Kinzler et al. used a similar technique to identify synthetic double-stranded DNA molecules that are specifically bound by DNA-binding polypeptides. Nucleic Acids Res. (1989) 17:3645-3653. Ellington et al. disclose the production of a large number of random sequence RNA molecules and the selection and identification of those that bind specifically to specific dyes such as Cibacron blue. Nature (1990) 346: 818-822.

Another technique for identifying nucleic acids that bind non-nucleic target molecules is the oligonucleotide combinatorial technique disclosed by Ecker, D. J. et al. [Nuc. Acids Res. 21, 1853 (1993)] known as synthetic unrandomization of randomized fragments (SURF), which is based on repetitive synthesis and screening of increasingly simplified sets of oligonucleotide analogue libraries, pools and mixtures [Tuerk, C. and Gold, L. Science 249, 505 (1990)]. The starting library consists of oligonucleotide analogues of defined length with one position in each pool containing a known analogue and the remaining positions containing equimolar mixtures of all other analogues. With each round of synthesis and selection, the identity of at least one position of the oligomer is determined until the sequences of optimized nucleic acid ligand aptamers are discovered.

Once a particular candidate aptamer has been identified through a SURF, SELEX or any other technique, its nucleotide sequence can be determined (as is known in the art), and its three-dimensional molecular structure can be examined by nuclear magnetic resonance (NMR). These techniques are explained in relation to the determination of the three-dimensional structure of a nucleic acid ligand that binds thrombin in Padmanabhan, K. et al., J. Biol. Chem. 24, 17651 (1993); Wang, K. Y. et al., Biochemistry 32, 1899 (1993); and Macaya, R. F. et al., Proc. Natl. Acad. Sci. USA 90, 3745 (1993). Selected aptamers may be resynthesized using one or more modified bases, sugars or backbone linkages. Aptamers consist essentially of the minimum sequence of nucleic acid needed to confer binding specificity, but may be extended on the 5' end, the 3' end, or both, or may be otherwise derivatized or conjugated.

D. Small Molecules

The term "small molecule" includes any chemical or other moiety, other than polypeptides and nucleic acids, that can act to affect biological processes. Small molecules can include any number of therapeutic agents presently known and used, or can be small molecules synthesized in a library of such molecules for the purpose of screening for biological function(s). Small molecules are distinguished from macromolecules by size. The small molecules of this invention usually have molecular weight less than about 5,000 daltons (Da), preferably less than about 2,500 Da, more preferably less than 1,000 Da, most preferably less than about 500 Da.

Small molecules include without limitation organic compounds, peptidomimetics and conjugates thereof. As used herein, the term "organic compound" refers to any carbon-based compound other than macromolecules such nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles and phenols. An organic compound as used herein also includes nitrated organic compounds and halogenated (e.g., chlorinated) organic compounds. Methods for preparing peptidomimetics are described below. Collections of small molecules, and small molecules identified according to the invention are characterized by techniques such as accelerator mass spectrometry (AMS; see Turteltaub et al., (2000) Curr Pharm Des 6:991-1007, and Enjalbal et al., (2000) Mass Spectrom Rev 19:139-61.

Preferred small molecules are relatively easier and less expensively manufactured, formulated or otherwise prepared. Preferred small molecules are stable under a variety of storage conditions. Preferred small molecules may be placed in tight association with macromolecules to form molecules that are biologically active and that have improved pharmaceutical properties. Improved pharmaceutical properties include changes in circulation time, distribution, metabolism, modification, excretion, secretion, elimination, and stability that are favorable to the desired biological activity. Improved pharmaceutical properties include changes in the toxicological and efficacy characteristics of the chemical entity.

E. Peptidomimetics

In general, a "polypeptide mimetic" ("peptidomimetic") is a molecule that mimics the biological activity of a polypeptide, but that is not peptidic in chemical nature. While, in certain embodiments, a peptidomimetic is a molecule that contains no peptide bonds (that is, amide bonds between amino acids), the term peptidomimetic may include molecules that are not completely peptidic in character, such as pseudo-peptides, semi-peptides and peptoids. Examples of some peptidomimetics by the broader definition (e.g., where part of a polypeptide is replaced by a structure lacking peptide bonds) are described below. Whether completely or partially non-peptide in character, peptidomimetics according to this invention may provide a spatial arrangement of reactive chemical moieties that closely resembles the three-dimensional arrangement of active groups in a polypeptide. As a result of this similar active-site geometry, the peptidomimetic may exhibit biological effects that are similar to the biological activity of a polypeptide.

There are several potential advantages for using a mimetic of a given polypeptide rather than the polypeptide itself. For example, polypeptides may exhibit two undesirable attributes, i.e., poor bioavailability and short duration of action. Peptidomimetics are often small enough to be both orally active and to have a long duration of action. There are also problems associated with stability, storage and immunoreactivity for polypeptides that may be obviated with peptidomimetics.

Candidate, lead and other polypeptides having a desired biological activity can be used in the development of peptidomimetics with similar biological activities. Techniques of developing peptidomimetics from polypeptides are known. Peptide bonds can be replaced by non-peptide bonds that allow the peptidomimetic to adopt a similar structure, and therefore biological activity, to the original polypeptide. Further modifications can also be made by replacing chemical groups of the amino acids with other chemical groups of similar structure, shape or reactivity. The development of peptidomimetics can be aided by determining the tertiary structure of the original polypeptide, either free or bound to a ligand, by NMR spectroscopy, crystallography and/or computer-aided molecular modeling. These techniques aid in the development of novel compositions of higher potency and/or greater bioavailability and/or greater stability than the original polypeptide. Dean (1994), BioEssays, 16: 683-687; Cohen and Shatzmiller (1993), J Mol Graph, 11: 166-173; Wiley and Rich (1993), Med Res Rev, 13: 327-384; Moore (1994), Trends Pharmacol Sci, 15: 124-129; Hruby (1993), Biopolymers, 33: 1073-1082; Bugg et al. (1993), Sci Am, 269: 92-98, all incorporated herein by reference.

Specific examples of peptidomimetics are disclosed in U.S. Pat. No. 7,169,390 which is commonly assigned with the instant application and incorporated herein in its entirety. These examples are illustrative and not limiting in terms of the other or additional modifications.

F. Polypeptides and Polypeptide Derivatives

Examples of polypeptides and derivatives thereof are disclosed in U.S. Pat. No. 7,169,390 which is commonly assigned with the instant application and incorporated herein in its entirety. These examples are illustrative and not limiting in terms of the other or additional modifications.

II. Applications

The invention is drawn to methods for treating or preventing autoimmune diseases and conditions, using one or more therapeutic agents that alter the activity or concentration of one or more bioactive lipids, or precursors or metabolites thereof. The therapeutic methods and compositions of the invention act by changing the "effective concentration", i.e., the absolute, relative, effective and/or available concentration and/or activities, of bioactive lipids. Lowering the effective concentration of a bioactive lipid may be said to neutralize the target lipid or its undesired effects, including downstream effects.

Without wishing to be bound by any particular theory, it is believed that bioactive signaling lipids, including S1P and/or LPA, and/or their metabolites or downstream effectors, may cause or contribute to the development of various diseases and disorders characterized by an aberrant, unwanted or excessive immune response. As such, the compositions and methods can be used to treat these immune-related diseases and disorders, particularly by decreasing the effective in vivo concentration of a particular target lipid, for example, S1P or LPA. In particular, it is believed that the compositions and methods of the invention are useful in treating autoimmune diseases, which by definition are characterized, at least in part, by an aberrant, excessive or unwanted immune response. Here, "unwanted" refers to an immune response that is undesired due to its involvement in a disease process, for example, an autoimmune response, or to an otherwise normal immune response which contributes to disease when present in excess, as in the case of transplant rejection or diseases characterized by inappropriate lymphocyte infiltration.

Examples of several classes of immune response-related diseases that may be treated in accordance with the invention are described below. It will be appreciated that many disease and conditions are characterized, at least in part, by multiple pathological processes and that the classifications provided herein are for descriptive convenience and do not limit the invention.

A. Reducing the Effective Concentration of Bioactive Lipids for the Treatment of Multiple Sclerosis As discussed hereinabove, the sphingosine analog FTY720 has been shown to be effective in reducing relapses and CNS lesions in patients with multiple sclerosis, an autoimmune disorder. Because FTY is an S1P receptor antagonist, and therefore blocks S1P signaling, it is believed that agents that bind bioactive signaling lipids, such as lysolipids S1P and LPA, and reduce their effective concentration, will also demonstrate efficacy in treatment of MS and other autoimmune diseases and conditions. This can be demonstrated using animal models, including the acute experimental autoimmune encephalomyelitis (EAE) model, which is widely used as a standard animal model MS. In the rat EAE model, FTY provided nearly complete protection against the onset of EAE disease, and was accompanied by a reduction in infiltration of T cells into the spinal cord. Normally in EAE, myelin basic protein-specific T lymphocytes attack the myelinated tissue in the CNS. Inflammatory lesions in the CNS were also absent in FTY-treated animals, but present in control animals. Fujino et al., (2003) Pharm and Exp Therap. 305:70-77.

B. Reducing the Effective Concentration of Bioactive Lipids for the Treatment of Arthritis Rheumatoid arthritis (RA) is an autoimmune disease that causes pain and disability due to joint inflammation and degradation. In two animal models of rheumatoid arthritis, FTY was compared to the anti-rheumatic compounds mizoribine and prednisolone in rat adjuvant-induced arthritis (AA) and collagen-induced arthritis (CIA) models. Efficacy of FTY720 at some doses was almost equal or higher as compared with mizoribine and prednisolone in both AA and CIA models. FTY, but not the other compounds, significantly decreased circulating lymphocyte levels in treated animals. FTY also demonstrated no abnormal side effects, leading the authors to conclude that it has a higher safety margin than the other two compounds, both of which demonstrated adverse effects. Matsuura, M. et al., (2000), Int. J. Immunopharmacol., 22:323-331. Because FTY is an S1P receptor antagonist, and therefore blocks S1P signaling, it is believed that agents that bind bioactive signaling lipids, such as lysolipids S1P and LPA, and reduce their effective concentration, will also demonstrate efficacy in treatment of RA and other autoimmune diseases and conditions.

C. Reducing the Effective Concentration of Bioactive Lipids for the Treatment of Diabetes Type I diabetes is an autoimmune disorder in which the immune system damages and/or destroys the beta cells in the Islets of Langerhans of the pancreas, eliminating insulin production. Based on the efficacy of FTY720 in other autoimmune conditions and in prevention of allograft rejection, this compounds effect on development of autoimmune diabetes in nonobese diabetic (NOD) mice has been examined. Animals were given FTY orally starting from 4 weeks of age. Daily FTY doses prevented development of diabetes in almost all treated mice, whereas most untreated NOD mice became diabetic by 35 weeks of age. Withdrawal of FTY at 35 weeks of age led to development of diabetes within 2 weeks in five mice, whereas the remaining mice maintained diabetes-free conditions for up to 44 weeks of age. No side effect of the drug was seen throughout the treatment period. FTY720 also prevented cyclophosphamide-induced diabetes in NOD mice. This led the authors to conclude that FTY is a safe and effective treatment and that it may be useful for long term treatment of prediabetic individuals. Maki T. et al. (2002) Transplantation, 74:1684-6. Continuous oral FTY720 treatment in overtly diabetic NOD mice has also been shown to lead to complete reversal of diabetes. Maki, T. et al., (2005) Transplantation, 79:1051-5. Because FTY is an S1P receptor antagonist, and therefore blocks S1P signaling, it is believed that agents that bind bioactive signaling lipids, such as lysolipids S1P and LPA, and reduce their effective concentration, will also demonstrate efficacy in treatment of Type 1 diabetes and other autoimmune diseases and conditions.

D. Reducing the Effective Concentration of Bioactive Lipids for the Treatment of Scleroderma Scleroderma is an autoimmune disease that causes scarring or thickening of the skin, and sometimes involves other areas of the body, including the lungs, heart, and/or kidneys. Scleroderma is characterized by the formation of scar tissue (fibrosis) in the skin and organs of the body, which can lead to thickening and firmness of involved areas, with consequent reduction in function. Today, about 300,000 Americans have scleroderma, according to the Scleroderma Foundation. One-third or less of those affected have widespread disease, while the remaining two-thirds primarily have skin symptoms. When the disease affects the lungs and causing scarring, breathing can become restricted because the lungs can no longer expand as they should. To measure breathing capability, doctors use a device that assesses forced vital capacity (FVC). In people with an FVC of less than 50 percent of the expected reading, the 10-year mortality rate from scleroderma-related lung disease is about 42 percent. One reason the mortality rate is so high is that no effective treatment is currently available.

As described in the examples of this application, existing evidence indicates that S1P and LPA are pro-fibrotic growth factors that can contribute to fibroblast activation, proliferation, and the resulting increased fibroblast activity associated with maladaptive scarring and remodeling. Moreover, potential roles for S1P and LPA in activity of skin and other types of fibroblasts have been demonstrated. For example, it has been shown that LPA stimulates the migration of murine skin fibroblasts [Hama, et al., (2004) J Biol Chem 279:17634-9], and human skin fibroblasts express several S1P receptor subtypes [Zhang, et al., (1999) Blood 93:2984-90]. In addition to the many direct effects of S1P on fibroblast activity, S1P also may have many potential indirect effects on fibroblast activity. For example, S1P may facilitate the action of other well-known pro-fibrotic factors, such as TGF-β and platelet derived growth factor (PDGF). TGF-β is one of the most widely studied and recognized contributors to fibrosis. Desmouliere, et al., (1993) J Cell Biol 122: 103-111. TGF-β upregulates SphK1 expression and activity leading to increased expression of tissue inhibitors of metalloproteinases 1 (TIMP-1), a protein that inhibits ECM degradation. Yamanaka, et al., (2004) J Biol Chem 279: 53994-54001. Increased expression of TIMP-1 is linked to interstitial fibrosis and diastolic dysfunction in heart failure patients. Heymans, et al., (2005) Am J Pathol 166: 15-25. Conversely, S1P stimulates expression and release of TGF-β Norata, et al., (2005) Circulation 111: 2805-2811. There is also distinct evidence of crosstalk between S1P and PDGF. S1P directly stimulates expression of PDGF. Usui, et al., (2004) J Biol Chem 279: 12300-12311. In addition, the S1P1 receptor and the PDGF receptor bind one another and their association is necessary for PDGF activation of downstream signaling which contributes to proliferation and migration of various cell types. Long, et al., (2004) Prostaglandins Other Lipid Mediat 80: 74-80; Baudhuin et al., (2004) Faseb J 18: 341-343. As such, the effects of TGF-β and PDGF on fibrosis may be due in part to crosstalk with the S1P signaling pathway. As such, the compositions and methods of the invention can be used to treat scieroderma, particularly by decreasing the effective in vivo concentration of a particular target lipid, for example, S1P and/or LPA.

Systemic scleroderma is thought to be exacerbated by stimulatory autoantibodies against PDGF receptors [Baroni, et al., (2006) N Engl J Med. 354:2667-76], and PDGF receptors are up-regulated in scleroderma fibroblasts in response to TGF-β. Yamakage, et al., (1992) J Exp Med. 175:1227-34. Because of the substantial cross-talk among the S1P, PDGF and TGF-β signaling systems, blocking S1P bioactivity with an anti-S1P agent (e.g., an anti-S1P mAb) could indirectly mitigate the pro-sclerotic effects of PDGF and TGF-β. Moreover, treatment with such an anti-S1P agent could benefit scleroderma patients by mitigating the direct effects of S1P, including fibrosis, on skin and other forms of fibroblasts that contribute to disease progression. Thus it is believed that agents that bind bioactive signaling lipids, such as lysolipids S1P and LPA, and reduce their effective concentration, will also demonstrate efficacy in treatment of scleroderma and other autoimmune diseases and conditions, particularly those with a fibrotic component. This gives these agents a distinct advantage over therapeutic agents that modulate either fibrosis or an immune response alone. "Inflammatory scarring" is a name given to a combination of inflammation and fibrosis, originally in the context of chronic renal disease. For discussion see Peters et al., (2004), Kidney Intl. 66: 1434-1443. It is believed that agents that decrease the effective concentration of bioactive signaling lipids, will be particularly effective in conditions characterized by both a scarring and an autoimmune and/or inflammatory component.

E. Reducing the Effective Concentration of Bioactive Lipids for the Prevention and Treatment of Allograft Rejection In animal models of corneal transplants, FTY720-treated mice showed a significant prolongation of orthotopic corneal-graft survival when administered orally. Zhang et al. (2003), Transplantation, vol 76: 1511-3. FTY oral treatment also significantly delayed rejection and decreased its severity in a rat-to-mouse model of corneal xenotransplantation. Sedlakova et al. (2005), Transplantation, vol 79, 297-303. Given the known pathogenesis of allograft rejection combined with these data suggesting that modulating the effects of the S1P signaling can improve graft survival, it is believed that agents that bind to, and thereby decrease the effective concentration of, bioactive lipids will also be useful in treatment of allograft rejection, graft-versus-host disease and other conditions characterized by an aberrant, undesired or excessive immune response.

FTY720 has been shown to prevent graft rejection and facilitate long-term graft acceptance in animal models (rat, dog) of heart, small bowel, kidney and liver allografts. In a human clinical trial of FTY in stable renal transplant patients, FTY was well tolerated and caused the expected reversible lymphopenia. Budde, K. et al., (2002) J. Am. Soc. Nephrol. 13:1073-1083. In an initial Phase 2a clinical trial to evaluate the efficacy and safety of FTY in de novo renal transplantation, in combination with mycophenolate mofetil (MMF), FTY was found to be as effective as MMF in combination with cyclosporine for the prevention of acute rejection after renal transplantation, and was well tolerated. Tedesco-Silva H. et al., (2005) Transplantation, 79:1553-60.

Because FTY is an S1P receptor antagonist, and therefore blocks S1P signaling, it is believed that agents that bind bioactive signaling lipids, such as lysolipids S1P and LPA, and reduce their effective concentration, will also demonstrate efficacy in treatment of allograft rejection, graft-versus-host disease and other conditions characterized, at least in part, by an aberrant, excessive or unwanted immune response.

F. Reducing the Effective Concentration of Bioactive Lipids for the Prevention and Treatment of Glomerulonephritis Immune diseases of the glomerulus, such as glomerulonephritis, are among the major causes of end-stage renal disease. These diseases share a progressive course characterized by fibrosis and inflammation of the tubulointerstitial compartment. "Inflammatory scarring" is a name given to a combination of inflammation and fibrosis, originally in the context of chronic renal disease. For discussion see Peters et al., (2004), Kidney Intl. 66: 1434-1443. It is believed that agents that decrease the effective concentration of bioactive signaling lipids, will be particularly effective in conditions characterized by both a scarring and an immune and/or inflammatory component.

In a rat model of glomerulonephritis, FTY720 treatment reduced circulating lymphocyte counts as well as renal lymphocyte infiltration. The course of disease progression was slowed significantly. Peters et al., supra. Because FTY is an S1P receptor antagonist, and therefore blocks S1P signaling, it is believed that agents that bind bioactive signaling lipids, such as lysolipids S1P and LPA, and reduce their effective concentration, will also demonstrate efficacy in treatment of glomerulonephritis, other immune-based kidney diseases and other conditions characterized, at least in part, by an aberrant, excessive or unwanted immune response.

III. Methods of Administration

The treatment for diseases and conditions such as the examples given above can be administered by various routes employing different formulations and devices. Suitable pharmaceutically acceptable diluents, carriers, and excipients are well known in the art.

One skilled in the art will appreciate that the amounts to be administered for any particular treatment protocol can readily be determined. Suitable amounts might be expected to fall within the range of 10 µg/dose to 10 g/dose, preferably within 10 mg/dose to 1 g/dose.

Drug substances may be administered by techniques known in the art, including but not limited to systemic, subcutaneous, intradermal, mucosal, including by inhalation, and topical administration. The mucosa refers to the epithelial tissue that lines the internal cavities of the body. For example, the mucosa comprises the alimentary canal, including the mouth, esophagus, stomach, intestines, and anus; the respiratory tract, including the nasal passages, trachea, bronchi, and lungs; and the genitalia. For the purpose of this specification, the mucosa will also include the external surface of the eye, i.e. the cornea and conjunctiva. Local administration (as opposed to systemic administration) may be advantageous because this approach can limit potential systemic side effects, but still allow therapeutic effect.

Pharmaceutical compositions used in the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations used in the present invention may be prepared according to conventional techniques well known in the pharmaceutical industry. Such techniques include the step of bringing into association the active ingredients with the pharmaceutical carrier(s) or excipient(s). Preferred carriers include those that are pharmaceutically acceptable, particularly when the composition is intended for therapeutic use in humans. For non-human therapeutic applications (e.g., in the treatment of companion animals, livestock, fish, or poultry), veterinarily acceptable carriers may be employed. In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment the pharmaceutical compositions may be formulated and used as foams. Pharmaceutical foams include formulations such as, but not limited to, emulsions, microemulsions, creams, jellies and liposomes.

While basically similar in nature these formulations vary in the components and the consistency of the final product. The know-how on the preparation of such compositions and formulations is generally known to those skilled in the pharmaceutical and formulation arts and may be applied to the formulation of the compositions of the present invention.

Various excipients might also be added to the formulated antibody to improve performance of the therapy, make the therapy more convenient or to clearly ensure that the formulated antibody is used only for its intended, approved purpose. Examples of excipients include chemicals to control pH, antimicrobial agents, preservatives to prevent loss of antibody potency, dyes, e.g., to identify the formulation for particular route of administration only, solubilizing agents to increase the concentration of antibody in the formulation, penetration enhancers and the use of agents to adjust isotonicity and/or viscosity. Inhibitors of, e.g., proteases, could be added to prolong the half life of the antibody.

The antibody might also be chemically modified to yield a pro-drug that is administered in one of the formulations or devices previously described above. The active form of the antibody is then released by action of an endogenous enzyme. Possible ocular enzymes to be considered in this application are the various cytochrome p450s, aldehyde reductases, ketone reductases, esterases or N-acetyl-β-glucosamidases.

Other chemical modifications to the antibody could increase its molecular weight, and as a result, increase the residence time of the antibody in the eye. An example of such a chemical modification is pegylation [Harris and Chess (2003), Nat Rev Drug Discov; 2: 214-21], a process that can be general or specific for a functional group such as disulfide [Shaunak et al. (2006), Nat Chem Biol; 2:312-3] or a thiol [Doherty et al. (2005), Bioconjug Chem; 16: 1291-8].

EXAMPLES

The invention will be further described by reference to the following detailed examples. These Examples are in no way to be considered to limit the scope of the invention.

Example 1

Effect of Agents that Decrease the Effective Concentration of Bioactive Lipids on Lymphopenia As is summarized in Tables 1 and 2, a 28-day toxicology study with murine monoclonal antibody LT1002 (SPHIN-GOMAB) was performed at doses of 0, 30, 75 and 200 mg/kg. As is shown in data tables 1-7 below, there was a dose-related decline of lymphocytes at all dose levels and of basophils at the highest dose. This decline was reflected in an increase in % neutrophils, % monocytes and % reticulocytes and a parallel decrease in % lymphocytes. This decrease in circulating neutrophils parallels the effect seen with FTY720, a small molecule sphingosine analog, which is a novel immunosuppressive drug that acts by altering lymphocyte trafficking, resulting in peripheral blood lymphopenia.

TABLE 1

28-Day General Toxicology Study Design
28-Day General Toxicology Study

| | |
|---|---|
| Test Article | LT1002 |
| Species | C57Bl mouse |
| Number of Animals | 10/sex/group |
| Dose | 0, 30, 75 & 200 mg/kg |
| Route of Administration | iv Bolus by tail vein injection* |
| Duration | 28 consecutive daily administrations |
| GLP | Yes |
| Study Endpoints | Clinical observations, body & organ weights, food consumption, necropsy of 48 tissues, bone marrow smears, clinical chemistries, hematology, coagulation panels & dose formulation analyses |

*Dosing ip, instead of dosing iv, initiated on day 14 because of tail vein damage post multiple iv injections of test article

TABLE 2

Summary of Findings

| Parameter | Dose Group | Effect | Significance (p-value) |
|---|---|---|---|
| WBC | 30 | Reduced | 0.007 |
| | 75 | Reduced | 0.043 |
| | 200 | Reduced | 0.013 |
| HGB | 30 | Reduced | 0.037 |
| MCV | 200 | Increased | 0.040 |
| Lymph | 30 | Reduced | 0.001 |
| | 75 | Reduced | 0.003 |
| | 200 | Reduced | 0.002 |

TABLE 2-continued

Summary of Findings

| Parameter | Dose Group | Effect | Significance (p-value) |
|---|---|---|---|
| BASO | 30 | Reduced | 0.047 |
| NEUT (%) | 30 | Increased | 0.004 |
| | 75 | Increased | 0.001 |
| | 200 | Increased | 0.000 |
| LYMPH (%) | 30 | Reduced | 0.001 |
| | 75 | Reduced | 0.000 |
| | 200 | Reduced | 0.000 |
| MONO (%) | 30 | Increased | 0.010 |
| | 75 | Increased | 0.000 |
| | 200 | Increased | 0.000 |
| RETIC (%) | 75 | Increased | 0.042 |
| GLOB | 30 | Increased | 0.027 |
| | 75 | Increased | 0.007 |
| | 200 | Increased | 0.000 |
| A/G Ratio | 30 | Reduced | 0.012 |
| | 75 | Reduced | 0.007 |
| | 200 | Reduced | 0.000 |
| Ca | 75 | Increased | 0.045 |
| | 200 | Increased | 0.000 |
| Spleen (% of body weight) | 200 | Reduced | 0.020 |

Example 2

28-Day Toxicology Study In Mice With Anti-S1P Monoclonal Antibody—Effect on Spleen A 28-day study of LT1002 in mice performed by LAB Preclinical (Study 1005-2615), in which forty organs and the site of injection (tail), were evaluated for gross pathology in all Control and High Dose Level (Group 4; 200 mg/kg/day) animals. LT1002 is the murine version of LT1009, Lpath's anti-S1P monoclonal antibody.

Organs evaluated included adrenals, aorta (thoracic), brain (cerebral cortex, midbrain, cerebellum and medulla), cecum, colon, epididymides, esophagus, eyes, femur with marrow, gallbladder, heart, kidneys, liver (2 lobes), lungs with bronchi, lymph nodes (mandibular and mesenteric), mammary glands (inguinal), optic nerves, ovaries, pancreas, pituitary, prostate, rectum, salivary glands (mandibular), sciatic nerve, seminal vesicles, skeletal muscle (thigh), ski/subcutis (inguinal), small intestines (duodenum, ileum and jejunum), spinal cord (cervical, lumbar and thoracic) spleen, sternum with marrow, stomach, testes, thymus, thyroids with parathyroids, tongue, trachea, urinary bladder, uterus (horns, body and cervix) and vagina.

The following preliminary histopathological changes were noted by the LAB pathologist for Group 4 (200 mg/kg/day) animals. "Mild to moderate decreased size of the follicular marginal zone of the splenic white pulp was noted in 6/10 male and 5/10 female mice from Group 4. Although this finding did not suggest splenic lymphoid toxicity, it could not be excluded as a LT1002-related change. Decreased size of the splenic follicular marginal zone was characterized by variable narrowing of the lymphoid mantle (i.e., marginal zone), cuffing the lymphoid follicles of the white pulp.

Mild to marked increased extramedullary hematopoiesis of the splenic red pulp in 3/10 males and 5/10 females from Group 4 and mild increased extramedullary hematopoiesis of the splenic red pulp in one male and one female from Group 3 (75 mg/kg/day) (the only spleens examined in Group 3 mice) were considered potentially LT1002-related, but of no toxicological significance."

Histopathological examination of the spleen of all mice from Groups 2 (30 mg/kg/day) and Group 3 (75 mg/kg/day), and a full histopathologic assessment of all pre-terminal mice are underway. LAB reports no other findings from the histopathologic evaluation of tissues from the Group 4 (200 mg/kg/day) animals. As per protocol, no tissues from animals in other dose groups besides the 200 mg/kg/day and saline treated animals were studied except for tissue in animals exhibiting macroscopic abnormalities (i.e. local irritation at the site of injection).

FTY720—a small molecule super agonist/functional antagonist of at least one, or more, of the GPCR receptors for S1P—is in late clinical development for the treatment of relapsing, remitting multiple sclerosis. FTY720 is thought to act in animals and man by altering lymphocyte trafficking/homing patterns. FTY also provides protection in animal models of human cancer. The long-term effects of FTY720 include systemic lymphopenia and decreased T-cell responses after 2 weeks oral administration of 1 mg/kg/day to normal female C57BL or C3H mice: lymphocytes in peripheral blood, peripheral lymph nodes, mesenteric lymph nodes, Peyer's patches, and spleen were all decreased. The long-term effects of FTY720 in mice also include a reduction in spleen weights by 65% after 2 weeks oral administration of 1 mg/kg/day to normal female C57BL or C3H mice.

In the present study, decreased spleen weights observed in LAB study 1005-2615 in animals treated with 200 mg/kg/day LT1002 is consistent with the same finding reported with daily administration of FTY720. Because FTY720 and LT1002 affect the same set of cell receptors, albeit by different mechanisms, and because the two compounds possess overlapping pharmacologic profiles, the reduction in spleen weights and spleen morphology in the present study with LT1002 was not unexpected.

Example 3

Effect of Agents that Decrease the Effective Concentration of Bioactive Lipids on Lymphocyte Trafficking The S1P signaling inhibitor FTY720 is believed to act in an immunosuppressive manner by altering lymphocyte trafficking/homing patterns and acceleration of lymphocyte homing. Chiba et al., (1998) J. Immunol. 160: 5037. The effect of anti-S1P antibody on lymphocyte trafficking is also examined, essentially as in published methods. Schwab et al., (2005) Science 309: 1735-1739.

Mice are treated with murine S1P monoclonal antibody or an isotype matched control monoclonal antibody. Treatments consist of intravenous injection of antibody diluted into 200-300 μL of normal saline. Animals are sacrificed at varying times after antibody administration. Lymphocyte counts are performed in lymph nodes, spleen, thymus, blood and lymph. Antibody inhibition of S1P causes a decrease in circulating lymphocytes (i.e., lymphopenia) and a corresponding increase in lymphocytes in lymphoid organs similar to that seen after FTY treatment is expected.

Example 4

Efficacy of Agents that Decrease the Effective Concentration of Bioactive Lipids in an Immune Challenge Study $^{51}$Chromium-Release CTL Assays Primary ex vivo cytotoxic lymphocyte (CTL) assays are performed using $^{51}$Cr-labeled MC-57 cells incubated in the presence or absence of the immunodominant peptide) as targets, as described in Murali-Krishna, K., et al., (1998) Immunity 8(2): 177-87. Results are determined by applying the following equation and multiplying by 100%:

(Experimental lysis−spontaneous lysis)/(Maximal lysis−spontaneous lysis).

Intracellular Cytokine Staining (ICCS)

Splenocytes ($4 \times 10^6$) are incubated for 12 hr in 250 μL of RPMI-1640 containing 10% FBS and Golgi Stop (Pharmingen, San Diego, Calif.) in the presence of 2 μg/mL of the immunodominant H-$2^b$ restricted CD8+ T cell epitope peptide. Negative controls are incubated without peptide. Following stimulation, cells are stained for CD8 and intracellular IFN-γ as specified by the manufacturer (Pharmingen). Following staining, cells are analyzed by flow cytometry using a FACScan or FACSCalibur and the data analyzed for expression of CD8 and IFN-γ using CellQuest™ software (Becton Dickinson Immunocytometry Systems, San Jose, Calif.). Percent of peptide-specific activation of CD8+ T cells is calculated by dividing the number of CD8+ T cells expressing IFN-γ by the total number of CD8+ T cells. As a positive control for the induction of T cells to produce IFN-γ, an equivalent number of splenocytes from naïve control animals are incubated for 6 hr in the presence of 20 ng/mL phorbol-12-myristate-13-acetate (PMA, Calbiochem, La Jolla, Calif.) and 3 μM ionomycin (Calbiochem) prior to staining.

Example 5

Efficacy of Agents that Decrease the Effective Concentration of Bioactive Lipids in a Murine Experimental Allergic Encephalomyelitis (EAE) Model of MS EAE is an experimental autoimmune disease of the central nervous system (CNS) (Zamvil et al, (1990) Ann. Rev. Immunol., 8:579 and is a disease model for the human autoimmune condition, multiple sclerosis (MS) [Alvord et al, Experimental Allergic Model for Multiple Sclerosis, NY 511 (1984)]. It is readily induced in mammalian species [for example, SJL/J mice are a susceptible strain of mice (H-$2^S$)] by immunizations of myelin basic protein purified from the CNS (e.g., an emulsion of guinea pig or bovine spinal column) or an encephalitogenic proteolipid (PLP). Animals develop an acute paralytic disease and an acute cellular infiltrate is identifiable within the CNS. Thus in addition to serving as a standard model for MS, this model has also been used to determine T-cell infiltration into the CNS. T-lymphocytes are rarely found in the normal CNS, but during MS, HIV induced encephalomyelitis or other CNS inflammatory conditions these cells are present. Symptoms observed include muscle weakness, paralysis, and lack of coordination. The standard evaluation of disease severity in the EAE model measures clinical behavior on a 0-6 scale: 0) normal; 1) flaccid tail; 2) abnormal gait, hind leg weakness; 3) partial paralysis, severe ataxia; 4) minimal hind leg movement after painful stimulus; 5) no hind leg movement; 6) moribund state with little or no movement. Means are compared between groups to determine the effect of treatment on clinical scores and body weight gain. Statistical significance of clinical scores and weight are resolved using biostatistical analysis.

Example 6

Efficacy of Agents that Decrease the Effective Concentration of Bioactive Lipids in a Collagen-Induced Arthritis (CIA) Model of Rheumatoid Arthritis

Collagen-induced arthritis (CIA) is an animal model for the human autoimmune disease rheumatoid arthritis (RA). Trenthorn et al, (1977) J. Exp. Med., 146:857. This disease can be induced in many species by the administration of heterologous type II collagen [Courtenay et al, (1980) Nature, 283:665; Cathcart et al, (1986) Lab. Invest., 54:26], and this is an accepted model for study of the disease.

Collagen-induced arthritis (CIA) in the mouse is induced by immunization of susceptible mice strains with native type II collagen. Macroscopically evident arthritis occurs between days 28-35 after immunization and persists for several months until the joints ankylose. CIA shares several histopathologic features with RA including mononuclear cell infiltration and synovial cell hyperplasia with bone and cartilage destruction. In both RA and CIA, disease susceptibility is restricted by MHC class II alleles and autoreactive T cells are prominent in the joint. Because of these similarities, CIA is a widely used experimental model for RA. Typically, CIA is induced on day 1 in 6-7 week-old male mice by intradermal tail base injection of bovine or chicken collagen II (CII) supplemented with 2.0 mg/ml M. tuberculosis emulsified in complete Freund's adjuvant (CFA). On day 21, mice receive an intradermal tail base injection of CII in incomplete Freund's adjuvant. Clinical severity of disease is evaluated every 4 days. Each paw is scored for inflammation on a scale of 0-4: 0, normal; 1, erythema and mild swelling confined to ankle, or tarsals, or individual digits; 2, moderate erythema and swelling of tarsals and ankle; 3, severe erythema and mild swelling of ankle, tarsals and digits; 4, severe erythema and severe swelling of ankle, tarsals and digits. Total daily scores for each mouse is obtained by adding scores from all four paws. On day 60 mice are euthanized and forepaws are weighed. For histology, paws are fixed with 10% formalin, decalcified in Decal (Fisher), embedded in paraffin, and 5 μm sections are stained with hematoxylin/eosin.

Collagen-induced arthritis and djuvant-induced arthritis (AA) are widely used animal models for the evaluation of new anti-arthritic drugs. The disease development of these models is also accepted for T-cell-dependent counterparts of human rheumatoid arthritis. For example, anti-CD4 antibody suppresses the disease development of AA and CIA, indicating that CD4+-positive T cells play a major part in the induction of AA and CIA.

Another accepted mouse model for arthritis is the TNF transgene model. Transgenic mice expressing a modified human TNF-α transgene spontaneously develop a chronic polyarthritis providing further evidence for the direct involvement of TNF in the pathogenesis of human RA. Mice carrying a human TNF transgene with a modified 3' region from a human globin gene show deregulated human TNF expression resulting in low level expression of TNF in the joints and a variety of other organs. In contrast, mice carrying a wild type human TNF transgene showed appropriately regulated TNF expression. Mice with deregulated TNF expression developed a chronic symmetric polyarthritis with histologic features similar to human RA. This process does not require a specific genetic background in the target mice. Other well accepted animal models for RA are reviewed in Kannan, K. et al., (2005), Pathophysiology 12:167-181.

The efficacy of anti-S1P monoclonal antibody is evaluated in the CIA animal model of rheumatoid arthritis. Age 6-8 week old male DBA1/J mice are purchased from Jackson Laboratory (Bar Harbor, Me.). They are fed with high-fat content mouse chow (Purina mouse chow 5015) and given deionized water, ad libitum.

Animals are randomized to treatment groups (10 mice/group) based on body weight. Animals receive vehicle (saline), anti-S1P monoclonal antibody or positive control (dexamethasone) beginning on Day 21. Dosing is p.o. except for dexamethasone which is given s.c. Three dose groups (low, medium and high) of antibody are used. All test articles are tested for the presence of endotoxin because LPS contamination can have a stimulating effect on the disease progression and may interfere with the evaluation of drug efficacy. Severity scores/paw volumes are measured three times per week beginning on Day 21 and continuing until Day 42.

To induce arthritis, chick type II collagen in Complete Freund's adjuvant (CFA) (mixed 1:1) is administered to all animals by intradermal route at the tail on Day 1 and boosted with type II collagen in Incomplete Freund's adjuvant (IFA) on Day 21. Beginning on Day 21 and continuing through Day 42, clinical severity score and paw volumes are measured on two hind paws three times per week. Paw thickness is measured using a calibrated caliper. Body weights are monitored weekly. General cage side observations are monitored at least once per day. At necropsy, both hind paws are collected and preserved in 10% buffered formalin. Hind paws collected at the necropsy are subject to microradiography using a Faxitron machine.

Paw/ankle are decalcified in formic acid until radiotranslucent. Four micron sections are prepared and stained with Safarin O and tartrate resistant acid phosphatase. The histology sections are qualitatively assessed for their extent of inflammation, articular cartilage damage, bone resorption and destruction, and synovial tissue changes.

Example 7

Efficacy of Agents that Decrease the Effective Concentration of Bioactive Lipids in a Mouse Model of Type 1 Diabetes

It has been shown that treatment of nonobese diabetic (NOD) mice with FTY720 prevents the onset of diabetes. Continuous oral FTY720 treatment in overtly diabetic NOD mice can also result in reversal of diabetes. See Maki et al., supra. It is believed that agents, such as anti-S1P monoclonal antibody, that decrease the effective concentration of bioactive lipids will have a similar effect on diabetes. This will be tested in standard NOD mouse models using standard methods.

Example 8

Efficacy of Agents that Decrease the Effective Concentration of Bioactive Lipids in a Murine Scleroderma Model

Scleroderma, a debilitating acquired connective tissue disease, is characterized by fibrosis, particularly of the skin and lungs. A murine sclerodermatous graft-vs-host disease (Scl GVHD) model for scleroderma has been developed for the study of basic immunologic mechanisms that drive fibrosing diseases and GVHD itself. This model reproduces important features of scleroderma including skin thickening, lung fibrosis, and up-regulation of cutaneous collagen mRNA, which is preceded by monocyte infiltration and the up-regulation of cutaneous TGF-1 mRNA. McCormick, L. L. (1999) J. Immunol. 163: 5693-5699. Briefly, recipient mice are lethally irradiated and then injected with allogeneic donor spleen and bone marrow cell suspension. Sclerodermatous thickening of skin is detectable by day 21 post-BMT by image analysis of routine histopathological sections. Other animal models for scleroderma are discussed in a review by Varga: Lakos G, Takagawa S, Varga J. (2004) Methods Mol Med. 102:377-93.

Anti-S1P antibody or other agents that bind and reduce the effective concentration of bioactive lipid are administered by tail vein injection on day 1 and again on day 6 post-bone marrow transplant. Mice are sacrificed at day 21 and skin and other tissues are collected, measured for thickening, and analyzed for collagen and immune cells.

Example 9

Efficacy of Agents that Decrease the Effective Concentration of Bioactive Lipids in Animal Allograft Models Cardiac Allografts:

To determine the therapeutic effects of anti S1P antibody and other agents that decrease the effective concentration of bioactive lipids in preventing allograft rejection, these compounds are tested for activity in a murine vascularized heterotopic heart transplant model. Hearts from Balb/c mice are transplanted into the abdominal cavity of C3H mice as primary vascularized grafts essentially as described by Isobe et al., Circulation 1991, 84, 1246-1255. Test compounds are administered by injection into tail vein, or by continuous pump and allograft survival time is monitored by detection of a second heartbeat. Mean survival time of the allograft is expected to increase with anti-S1P antibody or other agents that decrease the effective concentration of bioactive lipids.

Renal Allografts:

A well-established model to study chronic rejection in renal allografts is the F344 to LEW rat model. All LEW recipients of F344 grafts develop acute rejection at approximately day 30 resulting in 50% graft loss. The surviving animals show histopathological and functional characteristics of CR from day 50. Joosten, S. A. et al., (2002) American Journal of Pathology 160:1301-1310. To determine the therapeutic effects of anti S1P monoclonal antibody and other agents that decrease the effective concentration of bioactive lipids in preventing allograft rejection, these compounds are tested for activity in the F344 to LEW rat model, essentially as described by Joosten et al. (supra).

Corneal Allografts:

Corneal transplantation (penetrating keratoplasty (PK)) is the most successful tissue transplantation procedure in humans, yet corneal allograft rejection is still the leading cause of corneal graft failure. [Ing J J et al. (1998), Ophthalmology, vol 105: 1855-1865]. Recently it has been discovered that CD4(+) T cells function as directly as effector cells and not helper cells in the rejection of corneal allografts. [Hegde S et al. (2005), Transplantation, vol 79: 23-31]. Murine studies have shown increased numbers of neutrophils, macrophage and mast cells in the stroma of corneas undergoing rejection. Yamagami S et al. (2005), Mol Vis, vol 11, 632-40.

FTY720 is an immunosuppressive drug that acts by altering lymphocyte trafficking; its immune-modulating effects are mediated by binding to some of the S1P receptors expressed on lymphocytes. [Bohler T et al. (2005), Transplantation, vol 79: 492-5]. FTY treated mice showed a significant prolongation of orthotopic corneal-graft survival when administered orally. [Zhang et al. (2003), Transplantation, 76: 1511-3]. FTY oral treatment also significantly delayed rejection and decreased its severity in a rat-to-mouse model of corneal xenotransplantation [Sedlakova et al. (2005), Transplantation,79: 297-303]. Given the known pathogenesis of allograft rejection combined with the data suggesting that modulating the effects of the S1P signaling can improve corneal graft survival, it is believed that agents, for example, anti-S1P monoclonal antibody or other antibodies, that decrease the effective concentration of bioactive lipids, will also be useful in treatment of immunologic conditions such as allograft rejection, for example by attenuating the immune response, and thus will likely improve corneal graft survival. These agents are administered by injection into the tail vein or administered directly into the eye and are expected to prolong graft survival.

Example 10

Efficacy of Agents that Decrease the Effective Concentration of Bioactive Lipids in Animal Models of Glomerulonephritis Immune diseases of the glomerulus, such as glomerulonephritis, are among the major causes of end-stage renal disease. These diseases share a progressive course characterized by fibrosis and inflammation of the tubulointerstitial compartment. For discussion see Peters et al., (2004), Kidney Intl. 66: 1434-1443. It is believed that agents, such as anti-S1P antibody or other agents that decrease the effective concentration of bioactive signaling lipids, will be particularly effective in conditions characterized by both a scarring and an autoimmune and/or inflammatory component.

In a rat model of glomerulonephritis, FTY720 treatment reduced circulating lymphocyte counts as well as renal lymphocyte infiltration. The course of disease progression was slowed significantly. Peters et al., supra. Because FTY is an S1P receptor antagonist, and therefore blocks S1P signaling, it is believed that agents that bind bioactive signaling lipids, such as lysolipids S1P and LPA, and reduce their effective concentration, will also demonstrate efficacy in treatment of glomerulonephritis, other immune-based kidney diseases and other conditions characterized, at least in part, by an aberrant, excessive or unwanted immune response.

Mouse models for glomerulosclerosis, a model system for glomerulonephritis, exist. Gao et al. (2004) Molec. Cell. Biol. 24: 9899. The effect of anti S1P monoclonal antibody on renal fibrosis and inflammation is tested in a mouse model of glomerulosclerosis essentially according to Gao. Because of its effect on both the immune response and fibrosis, anti-S1P monoclonal antibody and other agents that decrease the effective concentration of bioactive lipids are expected to be particularly effective at slowing renal autoimmune disease progression.

The disclosures of each and every patent, patent application, and publication cited herein are hereby incorporated herein by reference in their entirely.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of decreasing an immune response in an animal, comprising administering to said animal an antibody or antigen binding fragment that binds a sphingolipid or sphingolipid metabolite and neutralizes said sphingolipid or sphingolipid metabolite, whereby the immune response in said animal is decreased.

2. The method of claim 1 wherein the sphingolipid is sphingosine-1-phosphate.

3. The method of claim 1 wherein the antibody is a monoclonal antibody.

4. The method of claim 3 wherein the monoclonal antibody is a humanized monoclonal antibody.

5. The method of claim 1 wherein the animal is a human.

6. The method of claim 1 wherein the immune response is an aberrant, excessive or undesired immune response.

7. The method of claim 6 wherein the aberrant, excessive or undesired immune response is an autoimmune response.

8. A method of treating a disease or condition in an animal, said disease or condition being characterized by an aberrant, excessive or undesired immune response, comprising administering to said animal an antibody or antigen binding fragment that binds a sphingolipid or sphingolipid metabolite and neutralizes said sphingolipid or sphingolipid metabolite, thereby treating the disease or condition characterized by an aberrant, excessive or undesired immune response.

9. The method of claim 8 wherein the sphingolipid is sphingosine-1-phosphate.

10. The method of claim 8 wherein the antibody is a monoclonal antibody.

11. The method of claim 10 wherein the monoclonal antibody is a humanized monoclonal antibody.

12. The method of claim 8 wherein the animal is a human.

13. The method of claim 8 wherein the aberrant, excessive or undesired immune response is an autoimmune response.

* * * * *